(12) United States Patent
Sherts et al.

(10) Patent No.: US 9,066,717 B2
(45) Date of Patent: Jun. 30, 2015

(54) SUTURE PASSER GUIDES AND RELATED KITS AND METHODS

(71) Applicant: CooperSurgical, Inc., Trumbull, CT (US)

(72) Inventors: Charles Sherts, Westport, CT (US); Binh Bao Vu, Lansdale, PA (US); David G. Reed, Langhorne, PA (US); Todd J. Kent, Cherry Hill, NJ (US); Craig Hidalgo, Langhorne, PA (US)

(73) Assignee: CooperSurgical, Inc., Trumbull, CT (US)

( * ) Notice: Subject to any disclaimer, the term of this patent is extended or adjusted under 35 U.S.C. 154(b) by 97 days.

(21) Appl. No.: 13/781,981

(22) Filed: Mar. 1, 2013

(65) Prior Publication Data

US 2013/0310856 A1    Nov. 21, 2013

Related U.S. Application Data

(60) Provisional application No. 61/648,897, filed on May 18, 2012, provisional application No. 61/672,467, filed on Jul. 17, 2012.

(51) Int. Cl.
| | |
|---|---|
| *A61B 17/04* | (2006.01) |
| *A61B 17/00* | (2006.01) |
| *A61B 19/02* | (2006.01) |
| *A61B 17/06* | (2006.01) |

(Continued)

(52) U.S. Cl.
CPC ......... *A61B 17/0482* (2013.01); *A61B 17/0057* (2013.01); *A61B 17/0469* (2013.01); *A61B 17/0485* (2013.01); *A61B 17/06109* (2013.01); *A61B 19/026* (2013.01); *A61B 2017/00637* (2013.01); *A61B 2017/00663* (2013.01); *A61B 2017/06104* (2013.01); *A61B 2017/2927* (2013.01); *A61B 2019/0278* (2013.01); *A61B 2019/462* (2013.01)

(58) Field of Classification Search
USPC .......................................... 606/139, 147, 148
See application file for complete search history.

(56) References Cited

U.S. PATENT DOCUMENTS

| | | | |
|---|---|---|---|
| 3,817,251 A | 6/1974 | Hasson | |
| 4,089,337 A | 5/1978 | Kronner | |

(Continued)

FOREIGN PATENT DOCUMENTS

| | | | |
|---|---|---|---|
| EP | 2 305 129 | 4/2011 | ............. A61B 17/04 |
| EP | 2 412 317 | 2/2012 | ............. A61B 17/04 |

(Continued)

OTHER PUBLICATIONS

International Search Report and the Written Opinion of the International Searching Authority for International Application No. PCT/US2013/028584 dated Jul. 16, 2013 (10 pages).

(Continued)

*Primary Examiner* — Tuan V Nguyen
(74) *Attorney, Agent, or Firm* — Fish & Richardson P.C.

(57) ABSTRACT

This disclosure relates to suture passer guides and related kits and methods. In certain aspects, a suture passer guide includes an elongate member and a suture positioning member that can be radially extended from a distal end region of the elongate member and rotated relative to the elongate member such that the suture positioning member can reposition a suture from a first side area of the elongate member to a second side area of the elongate member.

25 Claims, 41 Drawing Sheets

(51) Int. Cl.
  *A61B 17/29* (2006.01)
  *A61B 19/00* (2006.01)

(56) References Cited

U.S. PATENT DOCUMENTS

| | | | |
|---|---|---|---|
| 4,861,334 A | 8/1989 | Nawaz | |
| 5,002,557 A | 3/1991 | Hasson | |
| 5,197,971 A | 3/1993 | Bonutti | |
| 5,269,772 A | 12/1993 | Wilk | |
| 5,372,583 A | 12/1994 | Roberts et al. | |
| 5,496,335 A | 3/1996 | Thomason et al. | |
| 5,501,692 A | 3/1996 | Riza | |
| 5,507,758 A | 4/1996 | Thomason et al. | |
| 5,716,369 A | 2/1998 | Riza | |
| 5,882,344 A | 3/1999 | Stouder, Jr. | |
| 5,964,773 A * | 10/1999 | Greenstein | 606/148 |
| 5,993,471 A | 11/1999 | Riza et al. | |
| 6,142,931 A | 11/2000 | Kaji | |
| 6,183,485 B1 | 2/2001 | Thomason et al. | |
| 6,197,002 B1 | 3/2001 | Peterson | |
| 6,203,554 B1 | 3/2001 | Roberts | |
| 6,562,052 B2 * | 5/2003 | Nobles et al. | 606/144 |
| 6,783,516 B2 | 8/2004 | O'Heeron et al. | |
| 6,830,578 B2 | 12/2004 | O'Heeron et al. | |
| 7,842,049 B2 * | 11/2010 | Voss | 606/144 |
| 2003/0158572 A1 | 8/2003 | McFarlane | |
| 2004/0087978 A1 | 5/2004 | Velez et al. | |
| 2006/0025749 A1 | 2/2006 | Moenning | |
| 2006/0030868 A1 * | 2/2006 | Bennett | 606/148 |
| 2007/0191772 A1 | 8/2007 | Wojcik | |
| 2007/0198035 A1 * | 8/2007 | Threlkeld | 606/148 |
| 2007/0203507 A1 | 8/2007 | McLaughlin et al. | |
| 2008/0033459 A1 * | 2/2008 | Shafi et al. | 606/144 |
| 2008/0086165 A1 | 4/2008 | Lyon et al. | |
| 2008/0097485 A1 | 4/2008 | Shpaichler et al. | |
| 2010/0280327 A1 | 11/2010 | Nobis et al. | |
| 2011/0021880 A1 | 1/2011 | Okoniewski | |
| 2011/0112557 A1 | 5/2011 | Beeley | |
| 2011/0237901 A1 | 9/2011 | Duke et al. | |
| 2011/0270282 A1 * | 11/2011 | Lemke | 606/148 |
| 2012/0029532 A1 | 2/2012 | Hodgkinson et al. | |
| 2012/0035623 A1 | 2/2012 | Bagaoisan et al. | |
| 2012/0165611 A1 | 6/2012 | Warren et al. | |
| 2012/0238823 A1 | 9/2012 | Hagerty et al. | |
| 2012/0265223 A1 | 10/2012 | Shpaichler et al. | |
| 2014/0163323 A1 | 6/2014 | Mohajer-Shojaee | |

FOREIGN PATENT DOCUMENTS

| | | | |
|---|---|---|---|
| WO | WO 98/22040 | 5/1998 | A61F 2/00 |
| WO | WO 2006/111955 | 10/2006 | |
| WO | WO 2007/000159 | 1/2007 | |
| WO | WO 2009/031991 | 3/2009 | |
| WO | WO 2009/138839 | 11/2009 | |
| WO | WO 2010/000033 | 1/2010 | |
| WO | WO 2010/081096 | 7/2010 | |
| WO | WO 2013/019370 | 2/2013 | A61B 17/04 |

OTHER PUBLICATIONS

U.S. Appl. No. 13/555,660, entitled "Endoscopic Ports and Related Kits and Methods".

CooperSurgical, "Carter-Thomason CloseSure System," pp. 1-6; Oct. 2010.

CooperSurgical; "Marlow Balloon Cannula with Atraumatic Surface Disc," pp. 1-2, Sep. 1997.

Dr. A H Beeley, "The Beeley Trocar Brochure—Port Site Suture System Trocar," *Society of Laparoendoscopic Surgeons*, www.pssstlaparoscopy.com, pp. 2, 2011.

Elashry et al., "Comparative Clinical Study of Port-Closure Techniques Following Laparoscopic Surgery," *Journal of the American College of Surgeons*, vol. 183, pp. 335-344, Oct. 1996.

* cited by examiner

SUTURE PASSER GUIDES AND RELATED KITS AND METHODS

CROSS REFERENCE TO RELATED APPLICATION

This application claims the benefit under 35 U.S.C. §119 (e)(1) of U.S. Provisional Application No. 61/648,897, filed on May 18, 2012, and U.S. Provisional Application No. 61/672,467, filed on Jul. 17, 2012, each of which is incorporated by reference herein.

TECHNICAL FIELD

This disclosure relates to suture passer guides and related kits and methods.

BACKGROUND

Suture passer guides are medical devices that can be inserted through a wound, such as an endoscopic port site wound, and then used to guide a suture passer through tissue adjacent the wound in a desired manner to facilitate repair of the wound. Following an endoscopic surgical procedure, an endoscopic port is removed from an endoscopic port site wound in the patient and a suture passer guide is inserted into the wound. A suture passer is typically loaded with a suture and inserted through a passage within the suture passer guide in order to introduce the suture passer and the loaded suture through tissue adjacent one side of the wound and into the surgical cavity. The suture is then released from the suture passer, and the suture passer is removed from the passage. The suture passer is subsequently reinserted through another passage of the suture passer guide to introduce the suture grasper through tissue adjacent the other side of the wound and into the surgical cavity where the previously placed suture is grasped with the suture passer. The suture passer and the grasped suture are then removed from the passage such that the suture can be tied off to close the fascia, muscle and peritoneum layers of the endoscopic port site wound.

SUMMARY

In one aspect of the invention, a suture passer guide includes an elongate member and a suture positioning member that can be radially extended from a distal end region of the elongate member and rotated relative to the elongate member. The elongate member has a longitudinal axis and defines a first opening and a second opening that are substantially aligned with one another such that a suture passer and a suture grasped by the suture passer can be extended through the first and second openings at an acute angle relative to the longitudinal axis of the elongate member. The suture positioning member can reposition the suture from a first side area of the elongate member to a second side area of the elongate member.

In another aspect of the invention, a method includes inserting a suture passer guide into a wound, using a suture passer to dispose a suture adjacent a suture positioning member that is radially extended from an elongate member of the suture passer guide, and rotating the suture positioning member relative to the elongate member of the suture passer guide to reposition the suture from a first side area of the suture passer guide to a second side area of the suture passer guide.

Embodiments can include one or more of the following features.

In some embodiments, the suture positioning member is configured to rotate about an axis that is substantially parallel to or coincident with the longitudinal axis of the elongate member.

In certain embodiments, the suture positioning member is pivotably connected to a distal support member that is axially fixed to the elongate member.

In some embodiments, the suture passer guide further includes a shaft that extends through the elongate member, the shaft being configured to radially extend or radially retract the suture positioning member when the shaft is moved axially.

In certain embodiments, the suture passer guide further includes a distal base that is axially fixed relative to the shaft, the distal base defining a cavity configured to receive the suture positioning member when the suture positioning member is in a radially retracted position.

In some embodiments, the shaft is further configured to radially expand or radially collapse an expandable member that is secured to the elongate member.

In certain embodiments, the shaft is configured to rotate the suture positioning member relative to the elongate member when the shaft is rotated relative to the elongate member.

In some embodiments, the suture positioning member has a distal end region that is biased to a bent configuration.

In certain embodiments, the suture positioning member can be placed in a first axial position with respect to the elongate member in which the distal end region of the suture positioning member extends from the elongate member and in a second axial position with respect to the elongate member in which the distal end region of the suture positioning member is disposed within the elongate member.

In some embodiments, the distal end region of the suture positioning member assumes the bent configuration when the suture positioning member is in the first axial position and the distal end region of the suture positioning member assumes a substantially straight configuration when the suture positioning member is in the second axial position.

In certain embodiments, the suture positioning member is configured to cause an expandable member secured to the elongate member to radially expand or collapse when the suture positioning member is moved axially.

In some embodiments, the suture positioning member is formed of one or more shape-memory materials.

In certain embodiments, the suture positioning member is formed of nitinol.

In some embodiments, the suture positioning member is in the form of a wire.

In certain embodiments, the suture positioning member is slidable along an axis that is substantially parallel to or coincident with the longitudinal axis of the elongate member.

In some embodiments, the suture positioning member can be placed in a first axial position with respect to the elongate member in which the distal end region of the suture positioning member extends radially from the elongate member and in a second axial position with respect to the elongate member in which the distal end region of the suture positioning member is substantially parallel to or coincident with the longitudinal axis of the elongate member.

In certain embodiments, the suture positioning member can be moved from a radially extended position to a radially retracted position in which the suture positioning member extends along an axis that is substantially parallel to or coincident with the longitudinal axis of the elongate member.

In some embodiments, the suture passer guide further includes a base coupled to the distal end region of the elongate member, the base defining a cavity that receives the suture positioning member when the suture positioning member is in the radially retracted position.

In certain embodiments, the suture positioning member is configured such that at least a portion of the suture positioning member is substantially flush with an outer surface of the base when the suture positioning member is in the radially retracted position.

In some embodiments, the base includes an aperture through which the suture positioning member extends when the suture positioning member is in the radially extended position.

In certain embodiments, the suture positioning member forms an angle of about 90° to about 135° with the outer surface of the base when the suture positioning member is extended.

In some embodiments, the suture positioning member extends a maximum distance of about 0.75 inch to about 1.25 inch from the outer surface of the base, as measured perpendicular to the longitudinal axis, when the suture positioning member is radially extended.

In some embodiments, the base includes a lumen though which the suture positioning member is retractable and extendable.

In certain embodiments, the suture passer guide further includes a plug connected to a distal end region of the suture positioning member, the plug being sized to fit at least partially within the lumen of the base.

In some embodiments, the suture positioning member is in the form of a wire.

In certain embodiments, axial movement of the suture positioning member, the plug, and the base causes an expandable member secured to the elongate member to radially collapse.

In some embodiments, the suture positioning member is configured to rotate about an axis that is substantially perpendicular to the longitudinal axis of the elongate member.

In certain embodiments, the suture passer guide further includes an actuator that is rotatable with respect to the elongate member to rotate the suture positioning member about the axis that is substantially perpendicular to the longitudinal axis of the elongate member.

In some embodiments, the actuator is rotatable about an axis that is substantially perpendicular to the longitudinal axis of the elongate member.

In certain embodiments, the actuator is configured to radially expand or collapse when the actuator is moved axially with respect to the elongate member.

In some embodiments, the suture positioning member is coupled to the elongate member via a hinge.

In certain embodiments, the suture positioning member can be positioned in a first orientation that is substantially perpendicular to the longitudinal axis and in a second orientation that is substantially parallel to the longitudinal axis.

In some embodiments, the suture positioning member defines an aperture sized to receive a suture.

In certain embodiments, the suture positioning member includes two arms that define the aperture.

In some embodiments, a slit is defined between ends of the arms, the slit being configured to allow a suture to pass therethrough.

In certain embodiments, the arms have a width of about 1 mm to about 4 mm.

In some embodiments, a length of the aperture is about 0.5 inch to about 1.2 inches.

In certain embodiments, a width of the aperture is about 0.2 inch to about 0.4 inch.

In some embodiments, the suture positioning member includes two resilient arms configured to releasably retain a suture between the arms.

In certain embodiments, the suture positioning member includes a textured surface configured to contact the suture.

In some embodiments, the textured surface of the suture positioning member includes ridges.

In certain embodiments, the suture positioning member has a width of about 0.0625 inch to about 0.125 inch.

In some embodiments, the suture positioning member has a length of about 1.5 inches to about 2.5 inches.

In certain embodiments, the suture passer guide further includes an actuator having a graspable member extending from a proximal end region of the elongate member, wherein the actuator is configured to rotate the suture positioning member relative to the elongate member when the graspable member of the actuator is moved from a first position to a second position.

In some embodiments, the graspable member of the actuator is configured to rotate relative to the elongate member from the first position to the second position in order to rotate the suture positioning member from the first side area of the elongate member to the second side area of the elongate member.

In certain embodiments, the graspable member of the actuator is configured to rotate about an axis that is substantially perpendicular to the longitudinal axis of the elongate member.

In some embodiments, the graspable member of the actuator is configured to rotate about an axis that is substantially parallel to or coincident with the longitudinal axis of the elongate member.

In certain embodiments, the actuator includes rotational stops configured to limit rotational movement of the actuator relative to the elongate member.

In some embodiments, the elongate member defines cutouts configured to engage the rotational stops of the actuator.

In certain embodiments, the actuator includes frictional members configured to limit rotational movement of the actuator relative to the elongate member.

In some embodiments, the actuator is axially displaceable relative to the elongate member to axially displace the suture positioning member relative to the elongate member.

In certain embodiments, the graspable member of the actuator is axially displaceable relative to the elongate member to axially displace the suture positioning member relative to the elongate member.

In some embodiments, the actuator includes axial stops configured to limit axial movement of the actuator relative to the elongate member.

In certain embodiments, the actuator includes a shaft that extends through a lumen of the elongate member and is coupled to the suture positioning member.

In some embodiments, the graspable member is coupled to the proximal end region of the shaft to allow a user to move the shaft.

In certain embodiments, the shaft is configured to move axially relative to the elongate member.

In some embodiments, axial movement of the shaft causes axial movement of the suture positioning member.

In certain embodiments, the suture passer guide is configured such that axial movement of the suture positioning member causes the suture positioning member to extend radially from the distal end region of the elongate member.

In some embodiments, the shaft is configured to rotate relative to the elongate member.

In certain embodiments, rotational movement of the shaft relative to the elongate member causes rotational movement of the suture positioning member relative to the elongate member.

In some embodiments, a surface of the actuator has an indicator thereon.

In certain embodiments, the indicator indicates a direction in which the suture positioning member will extend radially from the distal end region of the elongate member upon moving the actuator to radially extend the suture positioning member.

In some embodiments, the indicator is in the form of an arrow.

In certain embodiments, the graspable member is coupled to a connecting member that extends through a lumen of the elongate member, and the connecting member is coupled to the suture positioning member in a manner such that when the graspable member of the actuator is placed in the first position, the suture positioning member is rotated to the first side area of the elongate member, and when the graspable member of the actuator is placed in the second position, the suture positioning member is rotated to the second side area of the elongate member.

In some embodiments, the connecting member is secured to a coupling member that is secured to a proximal end of the suture positioning member, and the coupling member is configured to rotate about an axis that is substantially perpendicular to the longitudinal axis of the elongate member and thus cause the suture positioning member to rotate about the axis that is substantially perpendicular to the longitudinal axis of the elongate member when the graspable member of the actuator is moved from the first position to the second position.

In certain embodiments, the connecting member is in the form of a wire.

In some embodiments, a base is secured to the distal end region of the connecting member, and the proximal end region of the suture positioning member engages the slot when the connecting member and the base are moved distally.

In certain embodiments, the suture positioning member is configured to move from a radially extended position to a radially retracted position when the connecting member and the base are moved distally.

In some embodiments, the suture positioning member is configured to move from the radially retracted position to the radially refracted position when the connecting member and the base are moved proximally.

In certain embodiments, the suture positioning member has a range of rotation of about 160° to about 200°.

In some embodiments, the suture positioning member is rotatable to about 80° to about 100° relative to the longitudinal axis of the elongate member.

In certain embodiments, the suture passer guide further includes an expandable member that is secured to the elongate member and that can be moved from a radially expanded position to a radially collapsed position.

In some embodiments, in the radially expanded position, the expandable member extends radially beyond a circumferential surface of the elongate member.

In certain embodiments, in the radially collapsed position, the expandable member is substantially flush with the circumferential surface of the elongate member.

In some embodiments, the suture positioning member forms an angle of about 0° to about 45° with the expandable member when the expandable member is in the radially expanded position and the suture positioning member is radially extended.

In certain embodiments, the suture positioning member is spaced about 0.25 inch to about 0.5 inch from a proximal surface of the expandable member when the expandable member is in the radially expanded position and the suture positioning member is radially extended.

In some embodiments, the suture passer guide further includes an actuator configured to move the expandable member from the radially expanded position to the radially collapsed position.

In certain embodiments, the actuator is further configured to radially extend the suture positioning member.

In some embodiments, the actuator is configured to radially expand the expandable member and radially extend the suture positioning member simultaneously.

In certain embodiments, the actuator is configured to radially collapse the expandable member.

In some embodiments, the actuator is further configured to rotate the suture positioning member from the first side area of the elongate member to the second side area of the elongate member.

In certain embodiments, the suture passer guide of claim further includes a base coupled to the distal end region of the elongate member, wherein the base is configured to radially expand the expandable member when the base is moved from a first position to a second position and to radially collapse the expandable member when the base is moved from the second position to the first position.

In certain embodiments, the suture passer guide further includes a spring coupling the base to the expandable member, the spring biasing the base to a distal position that causes radial expansion of the expandable member.

In some embodiments, the elongate member defines third and fourth openings that are substantially aligned with one another such that the suture passer can be extended through the third and fourth openings at an acute angle relative to the longitudinal axis of the elongate member.

In certain embodiments, the suture passer is passed through the first and second openings, a distal end of the suture passer is disposed in the first side area of the elongate member, and when the suture passer is passed through third and fourth openings, the distal end of the suture passer is disposed in the second side area of the elongate member.

In some embodiments, the elongate member defines a first guide passage that extends from the first opening to the second opening.

In certain embodiments, the elongate member defines a second guide passage that extends from the third opening to the fourth opening.

In some embodiments, an entire length of the first guide passage is laterally offset from the longitudinal axis in a first direction such that the first guide passage does not intersect the longitudinal axis, and an entire length of the second guide passage is laterally offset from the longitudinal axis in a second direction such that the second guide passage does not intersect the longitudinal axis.

In certain embodiments, the first and second guide passages have a diameter that is no more than about 0.020 inch to about 0.040 inch greater than an outer diameter of the suture passer.

In some embodiments, the suture positioning member is rotated about an axis that is substantially parallel to or coincident with a longitudinal axis of the elongate member of the suture passer guide.

In certain embodiments, the suture positioning member is rotated about an axis that is substantially perpendicular to a longitudinal axis of the elongate member of the suture passer guide.

In some embodiments, the method further includes radially extending the suture positioning member from the elongate member of the suture passer guide.

In certain embodiments, radially extending the suture positioning arm and rotating the suture positioning arm includes moving a single actuator.

In some embodiments, radially extending the suture positioning arm includes axially displacing the single actuator relative to the elongate member, and rotating the suture positioning arm includes rotating the single actuator relative to the elongate member.

In certain embodiments, the method further includes using the suture passer to retrieve the suture from the second side area of the suture passer guide.

In some embodiments, the suture passer is extended through first and second openings in the suture passer guide to dispose the suture adjacent the suture positioning member, and the suture passer is extended through third and fourth openings in the suture passer guide to retrieve the suture from the second side area of the suture passer guide.

In certain embodiments, using the suture passer to dispose the suture adjacent the suture positioning member includes passing the suture through an aperture defined by the suture positioning member.

In some embodiments, the wound is an endoscopic port site wound.

In certain embodiments, inserting the suture passer guide into the endoscopic port site wound includes inserting the suture passer guide into a lumen of an endoscopic port disposed within the endoscopic port site wound.

In some embodiments, the method further includes, after inserting the suture passer guide into the endoscopic port site wound, orienting the suture positioning member such that an aperture defined by the suture positioning member can receive the suture prior to passing the suture passer through the aperture.

In certain embodiments, orienting the suture positioning member such that the aperture can receive the suture includes rotating the suture positioning member to a position that is about 45° to about 100° relative to the longitudinal axis of the suture passer guide.

In some embodiments, using the suture passer to dispose the suture adjacent the suture positioning member includes extending a sufficient length of the suture through the aperture so that the suture positioning member pushes a portion of the suture from the first side of the suture passer guide to the second side of the suture passer guide.

In certain embodiments, the suture slides relative to the suture positioning member when the suture positioning member is rotated.

In some embodiments, the method further includes removing the suture passer guide from the wound.

In certain embodiments, as the suture passer guide is removed from the wound, the suture applies a force to a wall of an aperture of the suture positioning member such that movable arms forming the aperture move to allow passage of the suture through the wall of the aperture.

Embodiments can include one or more of the following advantages.

In certain embodiments, surgical procedures utilizing the suture passer guide can be carried out in less time than those that require an endoscopic port to be removed before inserting a suture passer guide. For example, repositioning a first end of the suture within the abdominal cavity for easy retrieval using the suture positioning member can substantially eliminate or reduce the time that would otherwise be required to tilt a suture passer guide for guidance of the distal end of the suture passer to a position within proximity to the first end of the suture or to use the suture passer to probe the abdominal cavity for the first end of the suture. Upon inserting the suture passer guide within the lumen of the endoscopic port and subsequently removing the endoscopic port, the port site wound forms a partial seal with the outer surface of the suture passer guide such that gases within the surgical cavity are substantially prevented from escaping through the wound and the inflation pressure within the surgical cavity is substantially maintained. Thus, inserting the suture passer guide through the lumen of the endoscopic port eliminates the time that would otherwise be required to re-insufflate the surgical cavity following removal of the endoscopic port. Furthermore, inserting the suture passer guide through the endoscopic port removes the need and time required to relocate the port site wound and navigating the suture passer guide through the wound following removal of the endoscopic port, which is required when using a type of suture passer guide that is inserted directly into the port site wound after removing the endoscopic port.

In some embodiments, the suture passer guide can reduce tissue damage to the patient. For example, the suture positioning member can prevent or significantly reduce the need to tilt the suture passer guide within the wound for the suture passer to easily grasp the first end of the suture. As a result, any tissue damage that might otherwise result from tilting a suture passer guide within a wound and using a suture passer to probe a surgical cavity for a suture can be substantially avoided or minimized. In contrast, suture passer guides that do not include rotatable or pivotable suture positioning members may not have the capability to easily position a suture within proximity to a distal opening of a guide passage. As a result, such suture passer guides may need to be tilted within a wound in order to more accurately guide a distal end of a suture passer to a location within grasping proximity of the suture, and a user may need to probe the surgical cavity with the distal end of the suture passer in order to grasp the suture.

In certain embodiments, the suture positioning arm is rotatable about an axis that is substantially parallel to or coincident with the longitudinal axis of the elongate member. This arrangement allows the suture to be deposited at any of various points adjacent the suture positioning arm while permitting the rotational movement of the suture positioning arm to carry the suture from the first side area of the suture passer guide to the second side area of the suture passer guide. The suture positioning member simply pushes or sweeps the suture. It is typically not necessary to manipulate the suture positioning member in a way to grasp the suture. As a result, the suture need not typically be precisely positioned at a specific location within the surgical cavity to enable the suture positioning member to reposition the suture. Such an arrangement can make wound repair procedures easier and faster.

In some embodiments, the suture passer guide includes an actuator that is configured to radially extend and/or radially retract the suture positioning arm relative to the elongate member and to rotate the suture positioning arm relative to the elongate member. In some embodiments, the actuator is also configured to radially expand and/or radially collapse an expandable member of the suture passer guide that can be used to stabilize the suture passer guide within a surgical cavity. Allowing a single actuator to perform these multiple different functions can make use of the suture passer guide for performing wound repairs faster and easier than suture passer guides having multiple different actuation mechanisms for carrying out these functions.

In certain embodiments, the suture passer guide is configured such that actuation of the expandable member and the suture positioning member occur at substantially the same time and due to one axial stroke of the plunger assembly. In addition, the suture passer guide can have a relatively short stroke length (i.e., a distance that the actuator is depressed to actuate either or both of the expandable member and the suture positioning member). The short stroke length and the simultaneous actuation of the expandable member and the suture positioning member can reduce the time needed to repair a wound using the suture passer guide as compared to certain suture passer guides that have longer stroke lengths and/or require sequential actuation of an expandable member and a suture positioning member.

In some embodiments, the expandable member and the suture positioning member are biased to radially expanded or radially extended positions. Alternatively, the suture passer guide can include a mechanism to lock the expandable member and the suture positioning member in their radially expanded or radially extended positions. As a result, the surgeon can perform a procedure without having to manually hold the actuator in a certain position throughout the procedure.

In certain embodiments, the suture positioning member has a geometry (e.g., a curved or axially offset geometry) such that, when the expandable member of the suture passer guide is in the expanded configuration and the suture positioning member is radially extended, the suture positioning member is positioned in close proximity to (e.g., within about 0.25 inch to about 0.5 inch of) an inner lining of a surgical cavity but without interfering with the expandable member. Such an arrangement helps to reduce or minimize the distance that the suture passer must protrude beyond the inner lining in order to dispose the suture in a location within the surgical cavity that allows the suture to be engaged and repositioned by the suture positioning arm.

In some embodiments, the expandable member of the suture passer guide includes multiple collapsible arms that are spaced from one another around the circumference of the expandable member, and certain collapsible arms are circumferentially spaced from one another by about 30° to about 60°. The circumferential gap between certain collapsible arms can be located on a same side of the suture passer guide as that which provides the openings of the guide passages. The size and location of the gap between the adjacent collapsible arms can help to ensure that a sufficient degree of tiltability of the suture passer guide is permitted in the region in which a suture passer exits the suture passer guide during use and can thus increase the ease with which the user can navigate the suture passer within a surgical cavity to grasp a suture.

In certain embodiments, the expandable member of the suture passer guide includes two collapsible arms that are spaced approximately 180° apart (as measured from centers of the collapsible arms) around a circumference of the expandable member and provide circumferential gaps between the two collapsible arms. The circumferential gaps are positioned along the sides of the elongate member that form the openings of the guide passages. As a result, the circumferential gaps are aligned with a direction in which the suture passer guide would typically need to be tilted during use in order to better access an end of the suture to retrieve the suture from the surgical cavity. Such a geometry reduces the force required to tilt the suture passer guide within the wound during use of the suture passer guide as compared to the force that would be required to tilt a suture passer guide including an expandable member having collapsible arms that form smaller circumferential gaps. Accordingly, the suture passer guide can be more easily tilted within the surgical cavity if necessary to allow a distal end of a suture passer to be placed in close proximity to the end of the suture within the surgical cavity of a patient so that the suture passer can be used to grasp the end of the suture.

In some embodiments, the expandable member of the suture passer guide includes collapsible arms that are arranged in groups that are spaced from one another around the circumference of the expandable member. Circumferential gaps between the groups of the collapsible arms are larger than circumferential gaps between adjacent collapsible arms within the groups. The circumferential gaps between the groups of arms can be located on a same side of the suture passer guide as that which provides the openings through which the suture passer is extended during use. The relatively large circumferential gaps between the groups of collapsible arms can improve the ease with which the suture passer guide can be tilted within a wound of a surgical wall. This arrangement can help to ensure that a sufficient degree of tiltability of the suture passer guide is permitted in the region in which a suture passer exits the suture passer guide during use and can thus increase the ease with which the user can navigate the suture passer within a surgical cavity to grasp a suture. This arrangement further reduces the force required to tilt the suture passer guide within the wound during use of the suture passer guide (as compared to the force that would be required to tilt a suture passer guide including an expandable member having collapsible arms that form smaller circumferential gaps that are aligned with the openings). Accordingly, while the suture passer guide is tilted within the wound and in contact with the inner lining of the surgical cavity, a distal end of a suture passer can be placed within adequate proximity to a suture within a surgical cavity of a patient.

In some embodiments, the suture passer guide is configured to be inserted into a surgical cavity through an endoscopic port. Inserting the suture passer guide through the endoscopic port rather than directly into the port site wound may prevent tissue damage that might otherwise result from inserting a suture passer guide directly into the wound. For example, when an endoscopic port is removed from a port site wound and then replaced by a suture passer guide, damage can be caused to the tissue surrounding the wound upon inserting the suture passer guide into the wound. With certain patients, particularly obese patients, it is often times difficult to relocate the original wound through the various layers of tissue within the wall forming the surgical cavity (i.e., the surgical cavity wall). In attempting to do so, the surgeon may inadvertently puncture tissue (e.g., fascia) adjacent the original wound, thereby creating an additional wound or enlarging the original wound. By designing the suture passer guide so that it can be inserted through the endoscopic port, the incidence of such inadvertent punctures can be reduced or eliminated.

In addition, wound repair procedures utilizing the suture passer guides described herein can result in improved placement of the suture as compared to repair procedures in which no such suture passer guide is used to facilitate placement of the suture. As a result, the quality of the repair can be improved as compared to those procedures that utilize no such suture passer guide.

In certain embodiments, positioning the expandable member, in its expanded form, against the lining of the surgical cavity wall (e.g., by applying a proximal force to the suture passer guide) helps to position the suture passer guide in a desired position relative to the surgical cavity wall to allow for a desired or optimal passage of the suture passer through the tissue of the wall. The passage and openings of the suture passer guide can, for example, be positioned in a desired manner relative to the inner surface of the surgical cavity wall such that a desired distance or bite is achieved between the placed suture and the outer surface of the suture passer guide (or the port site wound in which the suture passer guide is situated), along the inner surface of the surgical cavity wall. Positioning the passage and openings of the suture passer guide a known distance from the inner surface of the surgical cavity wall, as opposed to a known distance from the outer surface of the surgical cavity wall as is done in certain suture passer guides currently in use, can lead to more consistent high quality wound repairs. Pulling the expanded expandable member against the lining of the surgical cavity wall can also provide a greater space within the surgical cavity and thus help to ensure that unwanted tissue and organs are not inadvertently pierced with the suture passer.

Positioning the expandable member, in its expanded form, against the inner lining or inner surface of the surgical cavity wall can also help to prevent gases within the surgical cavity from escaping through the wound, thereby aiding in maintaining inflation pressure of the surgical cavity. In certain embodiments, for example, the suture passer guide is equipped with a film or other gas-impermeable material positioned over the expandable member. This arrangement can help to ensure that gases within the surgical cavity do not escape into the port site wound via the expandable member. Thus, the film can prevent loss of inflation pressure within the surgical cavity during use of the suture passer guide.

In certain embodiments, the suture passer guide includes guide passages configured such that approximately the same amount of tissue is grasped by a suture on either side of the port site wound when a suture passer is used in combination with the suture passer guide to place a suture in the surgical cavity wall. In other words, the geometry of the guide passages helps to ensure that the bite of the suture is approximately equally distributed on both sides of the wound. An equal bite distribution can improve the quality of the wound repair and reduce the time required for the wound to heal.

In certain embodiments, the suture passer guide includes guide passages at two different locations along the length of the suture passer guide, enabling the suture passer guide to be used for obtaining a desired suture bite in patients having a variety of different surgical cavity wall thicknesses. Because the same suture passer guide can be used for patients of various different sizes, the number of suture passer guides required to be kept on hand for a surgeon's use can be reduced.

In some embodiments, the suture passer guide includes seals, such as self-sealing plugs, that seal the passages of the suture passer guide. The seals can help to prevent loss of inflation pressure within the surgical cavity during use of the suture passer guide and can thus reduce or eliminate the need to re-insufflate the surgical cavity during a wound closing procedure.

In some embodiments, a suture passer guide includes non-crossing guide passages (i.e., non-intersecting guide passages) that are located on opposites of an internal shaft within an elongate tubular member of the suture passer guide. The non-intersecting guide passages provide several advantages to the structure and use of the suture passer guide, as compared to the structure and use of suture passer guides having guide passages that intersect one another along the longitudinal axis of the elongate member. For example, a suture passer that is being inserted through one of the guide passages will not damage a suture that was previously disposed in another guide passage since the guide passages do not intersect. Similarly, the suture passer will not get stuck at an intersection point of the passages or inadvertently be passed from one guide passage into another at an intersection point.

Other aspects, features, and advantages will be apparent from the description and drawings, and from the claims.

DETAILED DESCRIPTION

Figure 1:
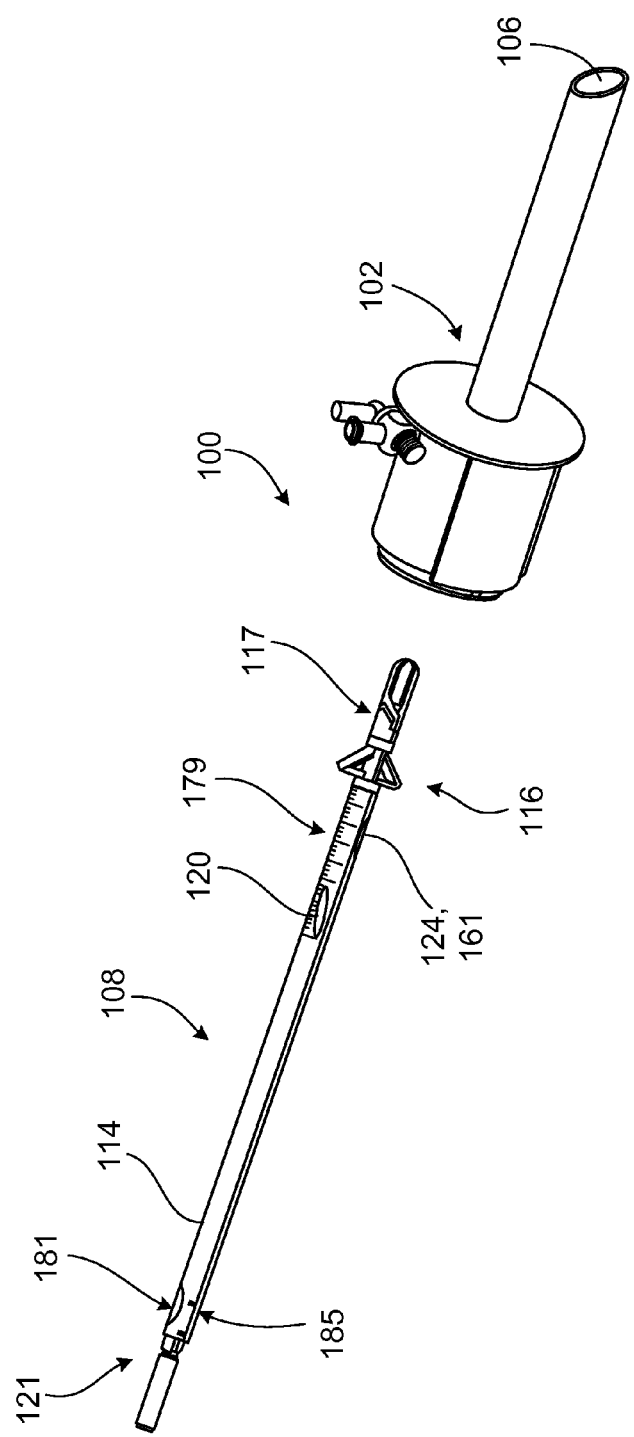
FIG. 1 is a perspective view of an assembly that includes an endoscopic port and a suture passer guide that includes a suture positioning member that is rotatable about an axis that is substantially perpendicular to a longitudinal axis of an elongate tubular member of the suture passer guide to allow a suture to be repositioned from one side area of the elongate tubular member of the suture passer guide to another side area of the elongate tubular member of the suture passer guide. The suture passer guide can be passed through a central lumen of the endoscopic port.

FIG. 1 illustrates a surgical assembly 100 that includes an endoscopic port 102 and a suture passer guide 108 that can be passed through a central lumen 106 of the endoscopic port 102. The suture passer guide 108 includes an expandable member 116 secured to a distal end region of an elongate tubular member 114 and a suture positioning member 117 coupled to a distal end region of the expandable member 117. The expandable member 116 can be expanded within a surgical cavity in order to retain the suture passer guide 108 within the surgical cavity during a procedure to repair an endoscopic port site wound. The suture positioning member 117 is configured to receive a suture and can be rotated relative to the elongate tubular member 114 to position an end of the suture at a desired location within the surgical cavity so that the end of the suture can be easily retrieved by a suture passer during the procedure. The suture passer guide 108 further includes guide passages 136, 138 (shown in FIG. 2) that can be used to guide the suture passer in a desired manner through tissue adjacent the endoscopic port site wound and into the surgical cavity to either deposit a suture into the suture positioning member 117 or to retrieve a suture from the suture positioning member 117.

Following completion of an endoscopic surgical procedure (e.g., a laparoscopic surgical procedure) that utilizes the endoscopic port 102, the suture passer guide 108 is inserted through the central lumen 106 of the endoscopic port 102 such that the expandable member 116 and the suture positioning member 117 of the suture passer guide 108 are positioned within the surgical cavity (e.g., the abdominal cavity) of the patient. The endoscopic port 102 is then removed from the endoscopic port site wound, leaving the suture passer guide 108 positioned within the wound and the expandable member 116 and the suture positioning member 117 of the suture passer guide 108 positioned within the surgical cavity. The suture positioning member 117 is subsequently rotated, and the suture passer, along with the suture, is inserted through selected guide passages of the suture passer guide 108. The suture passer, along with the suture, is then advanced into an aperture 115 of the suture positioning member 117 to position the suture in a desired manner within the tissue of the patient and to allow the suture to be repositioned within the surgical cavity by the suture positioning member 117. The suture passer is then removed, and the suture positioning member 117 is rotated to carry the suture from one side of the elongate tubular member 114 to another. The suture passer is subsequently inserted through the tissue adjacent the other side of the wound to retrieve the suture from the aperture 115 of the suture positioning member 117. The suture positioning member 117 serves to position the suture to be easily retrieved without significant tilting of the suture passer guide 108, which can save time and help to prevent damage to tissue surrounding the wound.

Figure 2:
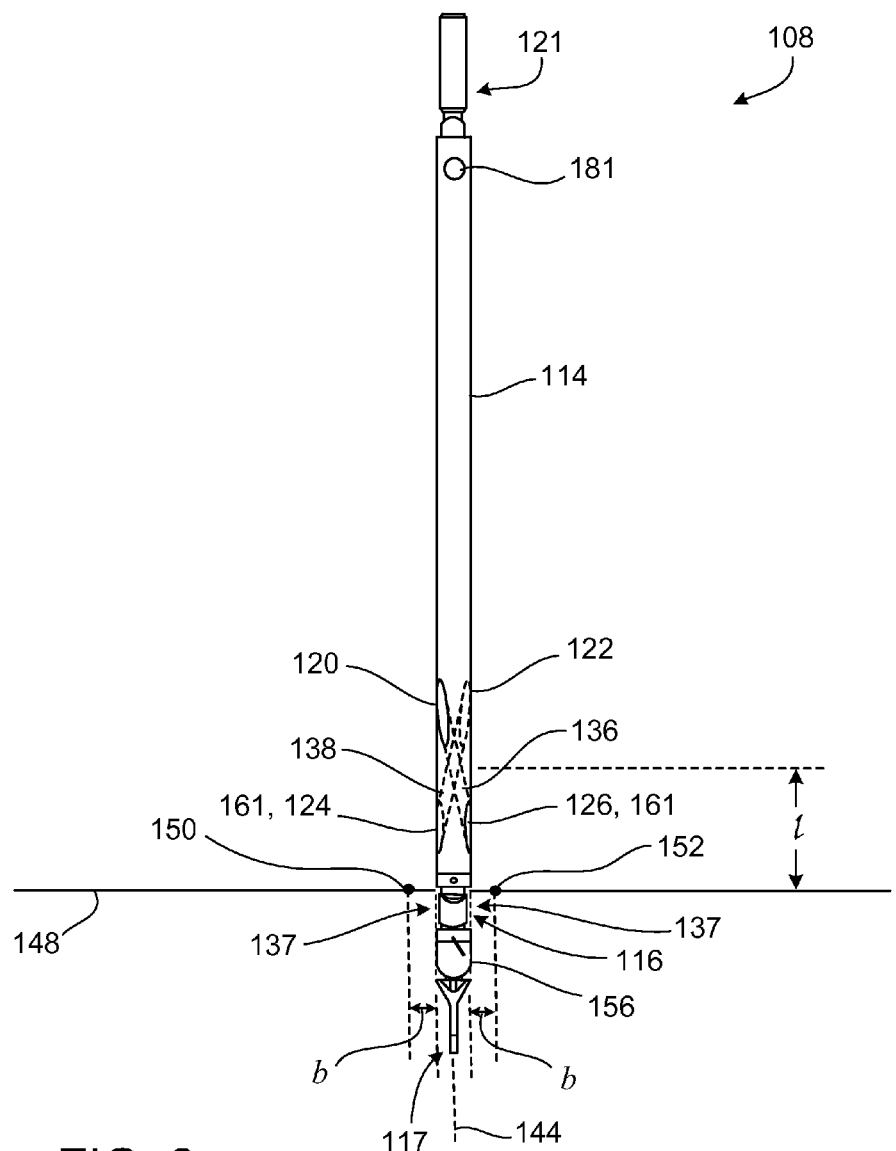
FIG. 2 is a front view of the suture passer guide of FIG. 1.

Referring now to FIG. 2, the elongate tubular member 114 of the suture passer guide 108 includes a sidewall defining four openings 120, 126 and 122, 124 that are aligned to form two guide passages 136, 138, respectively. The first guide passage 136 extends through a solid core of the elongate tubular member 114 from the left proximal opening 120 to the right distal opening 126, and the second guide passage 138 extends through the solid core of the elongate tubular member 114 from the right proximal opening 122 to the left distal opening 124. The guide passages 136, 138 are positioned on opposite sides of an internal shaft 168 (shown in FIG. 3) located within a central lumen of the elongate tubular member 114. Accordingly, the guide passages 136, 138 do not intersect one another. Nor do the guide passages 136, 138 intersect a longitudinal axis 144 of the elongate tubular member 114. Each of the guide passages 136, 138 typically extends at an acute angle relative to the longitudinal axis 144 of the elongate member 114. The left and right proximal openings 120, 122 are circumferentially spaced about 180° apart from each other. Similarly, the left and right distal openings 124, 126 are circumferentially spaced about 180° apart from each other. The left proximal opening 120 and the right distal opening 126 are circumferentially spaced about 150° to about 170° (e.g., about 160°) apart from each other. Similarly, the right proximal opening 122 and the left distal opening 124 are circumferentially spaced about 150° to about 170° (e.g., about 160°) apart from each other. The guide passages 136, 138 are sized to receive a suture passer to be used with the suture passer guide 108. The guide passages 136, 138 typically have a diameter that is about 0.07 inch to about 0.2 inch (e.g., about 0.14 inch) and allows a clearance of about 0.020 inch to about 0.040 inch around an outer diameter of the suture passer.

Still referring to FIG. 2, the distance l at which the guide passages 136, 138 are located (as measured to centroids of the guide passages 136, 138) from the proximal tissue contacting surface of the expanded expandable member 116 and the angles at which the guide passages 136, 138, extend from the proximal openings 120, 122 can be selected based on the desired bite to be provided by the suture. The combination of the distance l and the angles at which the guide passages 136, 138 extend determines the locations at which the suture passer punctures the inner lining of a surgical cavity (represented by line 148) and thus dictates the bite achieved by sutures positioned in the tissue by passing a suture passer loaded with the suture through the guide passages 136, 138. The points at which the suture passer punctures the lining 148 of the surgical cavity are denoted as a left puncture 150 and a right puncture 152, and distances b between the left puncture 150 and the sidewall of the elongate member 114 and between the right puncture 152 and the sidewall of the elongate member 114 represent the respective suture bites to be achieved.

These geometries facilitate passing the suture passer through the surgical cavity wall on each side of the wound at approximately the same angle and thus help to ensure that the suture bite is approximately equally distributed on both sides of the wound. An equal bite distribution can improve the quality of the wound repair and reduce the time required for the wound to heal.

In some embodiments, the guide passages 136, 138 extend through the suture passer guide 108 at angles of about 10° to about 30° (e.g., about 15°) relative to the longitudinal axis 144 of the elongate tubular member 114. Accordingly, the guide passages 136, 138 deliver the suture passer to punctures 150, 152 that are laterally spaced about 0.5 cm to about 2.0 cm (e.g., about 1 cm) from the sidewall of the elongate tubular member 114 (i.e., b≈0.5 to 2.0 (e.g., 1 cm)). When the suture positioning member 117 is rotated to an angle of about 45° to about 90° relative to the central axis 144 of the elongate tubular member 114, the angles at which the guide passages 136, 138 are oriented delivers a suture passer to an aperture defined by the suture positioning member 117, as will be described in more detail with respect to FIGS. 7, 9F, and 9H. In some embodiments, the distance l at which the guide passages 136, 138 are located (as measured to centroids of the guide passages) from the proximal tissue contacting surface of the expanded expandable member 116 is about 1.0 cm to about 6.0 cm (e.g., about 1.5 cm). As will be described below, the expandable member 116 is expanded and pulled against the inner lining 148 of the surgical cavity during use to ensure that the guide passages 136, 138 are located at known distances from the inner lining 148 of the surgical cavity regardless of the overall thickness of the patient's tissue. Because the guide passages 136, 138 are positioned at generally the same distances from the lining 148 of the surgical cavity from patient to patient (i.e., regardless of the varying thickness of tissue from patient to patient), the suture passer exit points (i.e., punctures 150, 152) will be substantially the same regardless of the thickness of the patient's tissue. The guide passages 136, 138 will typically be used for patients having a tissue thickness in a range of about 1.5 cm to about 6.0 cm.

The non-crossing guide passages (i.e., non-intersecting guide passages) 136, 138 provide several advantages to the structure and use of the suture passer guide 108, as compared to the structure and use of alternative suture passer guides having guide passages that intersect one another along a longitudinal axis of an elongate member of the suture passer guides. For example, during use of alternative suture passer guides, as the suture passer is passed through a second guide passage to retrieve an end of a suture that is located within the surgical cavity, care must be taken to prevent the suture passer from damaging the portion of the suture that was previously threaded through the first guide passage and extends through the common center region of the guide passages. The non-intersecting feature of the guide passages 136, 138 allows a user of the suture passer 108 to avoid this potential complication since the suture passer will not come into contact with a suture extending through one guide passage 136, 138 while the suture passer is being passed through the other guide passage 136, 138.

As another example, during use of alternative suture passer guides, as the suture passer is passed through the guide passages, care must be taken to prevent the distal end of the suture passer from becoming lodged within small gaps located between the lumen of the elongate tubular member and the internal shaft. In some instances, such contact between a suture passer and a suture passer guide could damage either or both of the suture passer and the suture passer guide. The integral feature of the non-intersecting guide passages 136, 138 (i.e., the guide passages 136, 138 extending through a solid core of the elongate tubular member 114) prevents such a complication since the non-intersecting guide passages 136, 138 do not have any gaps in their formations through the solid core of the elongate tubular member 114.

As yet another example, intersection regions of intersecting guide passages within the elongate tubular member of alternative suture passer guides have relatively thinned, weakened wall sections resulting from void spaces generated by the intersection regions in the wall sections. The elongate tubular member 114 of the suture passer guide 108 has comparatively thicker, stronger wall sections given that the elongate tubular member 114 does not have such void regions that would be provided by intersecting guide passages. The thicker, stronger wall sections of the elongate tubular member 114 can better withstand forces exerted on the wall sections as the elongate tubular member 114 is assembled (e.g., bonded together from the wall sections) relative to the force that elongate tubular members of alternative suture passer guides can withstand during assembly. Furthermore, due to the thicker, stronger wall sections of the elongate tubular member 114, the elongate tubular member 114 can include additional guide passages without reduced structural integrity as compared to elongate tubular members of alternative suture passer guides. In such embodiments, spacing a larger number of guide passages along the length of the elongate tubular member 114 can allow the suture passer guide 114 to be used to repair surgical walls having a larger range of thicknesses as compared to those that can be repaired using alternative suture passer guides. Additionally, the absence of a guide passage intersection void region within the elongate tubular member 114 allows the guide passages 136, 138 to be oriented at any angle with respect to the longitudinal axis 144 of the elongate tubular member 114. In contrast, the angle at which guide passages of alternative suture passer guides are oriented is limited by a size of the resulting guide passage intersection void region that can be allowed to maintain a desired level of structural integrity of the elongate tubular member.

As another example, the non-intersecting feature of the guide passages 136, 138 of the suture passer guide 108 allows two suture passers to be passed through the suture passer guide 108 simultaneously, while the intersecting feature of guide passages of alternative suture passer guides only allows one suture passer to be passed through the suture passer guide at a time.

Figure 3:
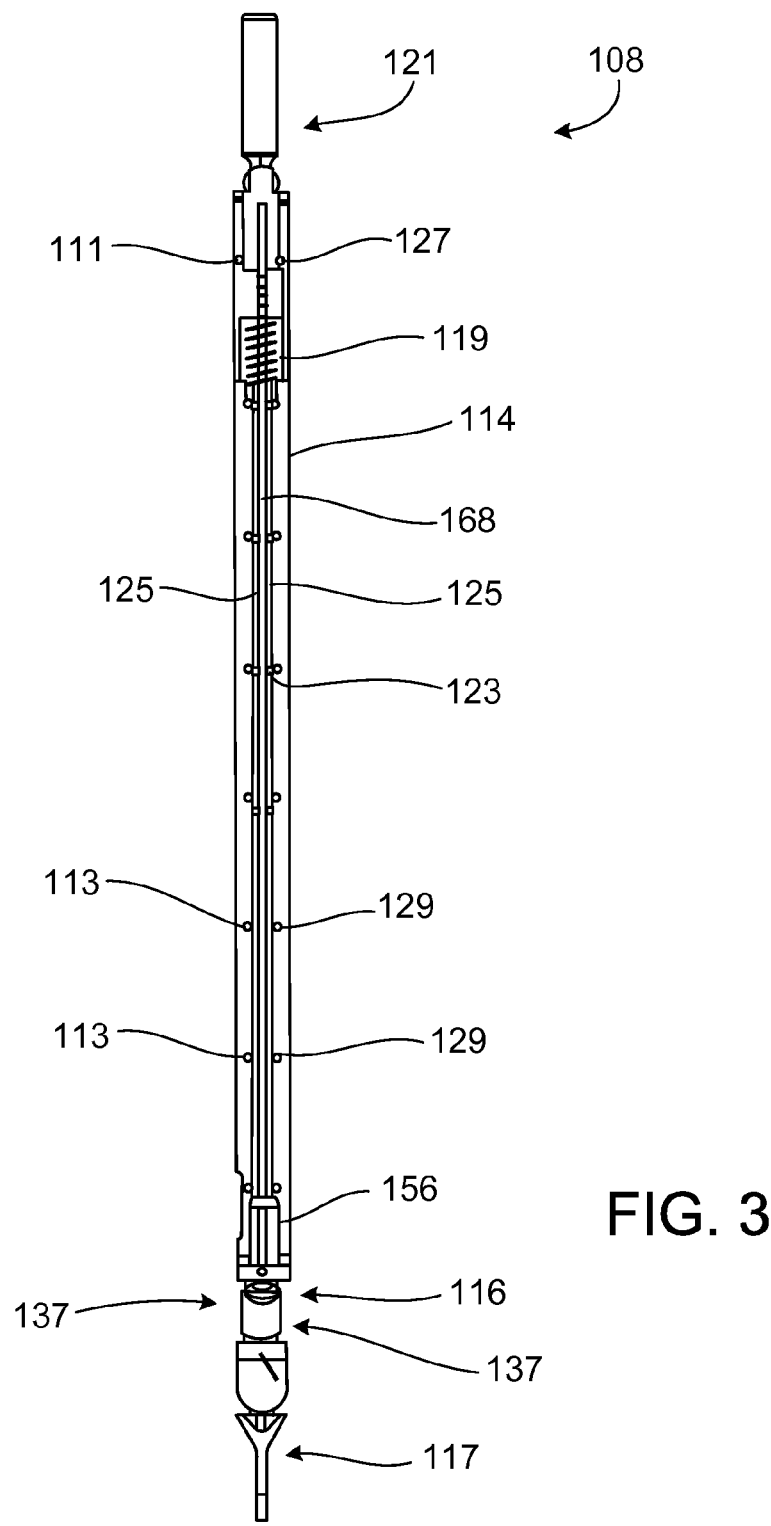
FIG. 3 is a front view of the suture passer guide of FIG. 1, with one half of an elongate tubular member of the suture passer guide removed to show certain internal components of the suture passer guide.

FIG. 3 illustrates a front view of the suture passer guide 108 with one half of the elongate tubular member 114 removed to show certain internal components of the suture passer guide 108. The elongate tubular member 114 defines a central lumen 119 having a variable diameter along a length of the elongate tubular member 114. At the proximal end of the elongate tubular member 114, the central lumen 119 is sized to surround a portion of a plunger assembly 121 secured to a proximal end of the internal shaft 168. Multiple support members 123 are positioned along a portion of the central lumen 119 and are formed to allow passage of the internal shaft 168 and two flexible elongate members 125 that are positioned on opposite sides of the internal shaft 168. At the distal end of the elongate tubular member 114, the central lumen 119 is sized to surround a portion of a distal base 156 that extends through the expandable member 116 and is coupled with the suture positioning member 117. The internal shaft 168 and the flexible elongate members 125 extend from the plunger assembly 121, through the distal base 156, and to the suture positioning member 117 of the suture passer guide 108. The plunger assembly 121, the internal shaft 168, the flexible elongate members 125, and the distal base 156 are components of an actuator or actuator assembly that can be used to radially expand and collapse the expandable member 116 and to radially extend and retract the suture positioning member 117, as will be described in more detail below.

In some embodiments, the flexible elongate members 125 may be a flexible tensional member, such as thread, wire, rope, or cable. In some examples, the flexible elongate members 125 can be formed of one or more materials including nylon, a woven strand material, or stainless steel. The flexible elongate members 125 typically have a diameter of about 0.010 inch to about 0.030 inch.

Several small and large pegs 111, 113 extend from each half of the elongate tubular member 114 and are sized to fit within respective complimentary small and large recesses 127, 129 positioned along the length of the opposite half of the elongate tubular member 114, which is not shown in FIG. 3. The pegs 111, 113 and recesses 127, 129 serve to align two halves of the elongate tubular member 114, which are typically held together with an appropriate adhesive.

Figure 4:
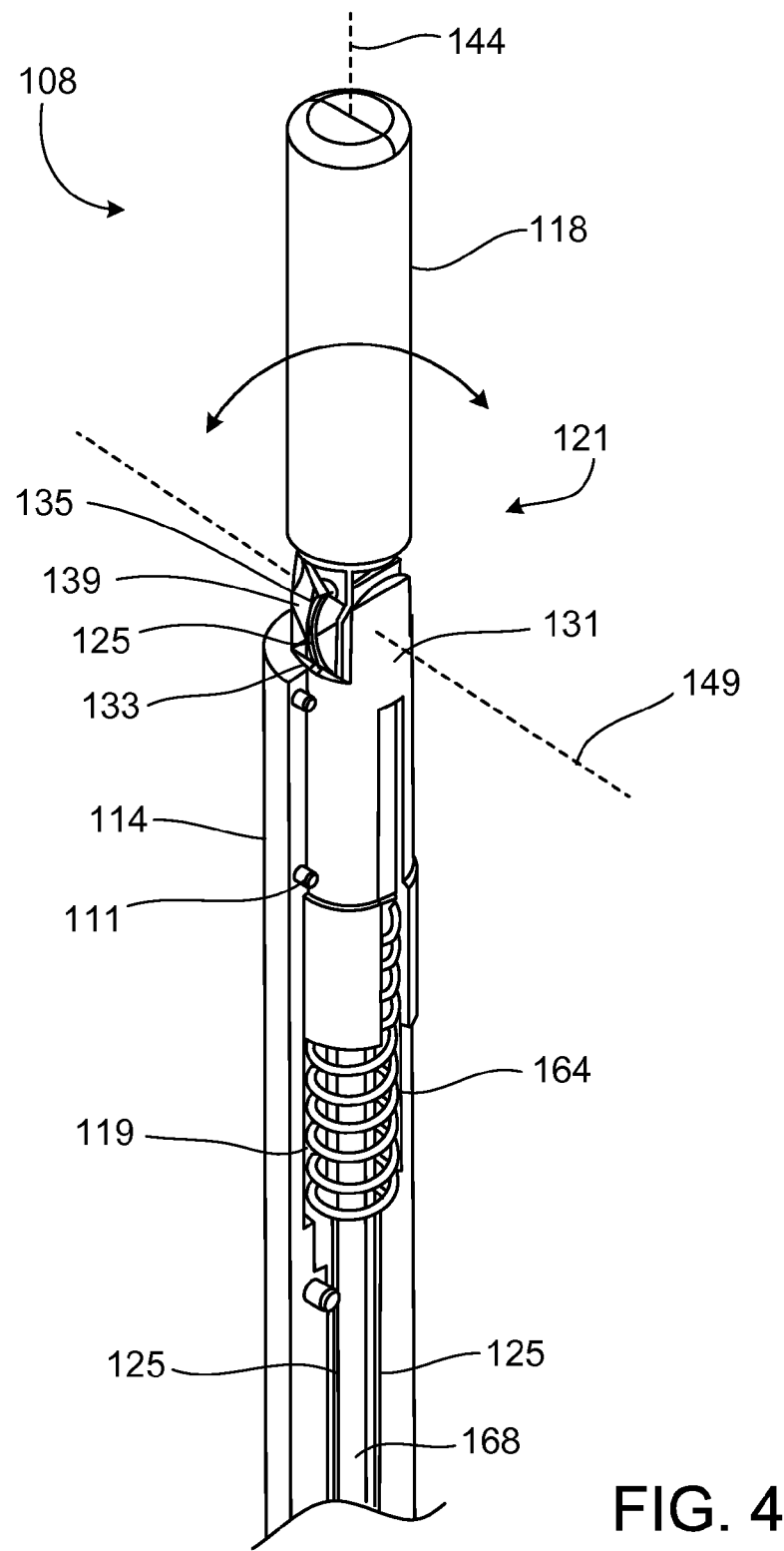
FIG. 4 is an enlarged, perspective view of a proximal end region of the suture passer guide of FIG. 1, with one half of the elongate tubular member removed to show a plunger assembly in a proximal position.

FIG. 4 is an enlarged view of the proximal end region of the suture passer guide 108 with one half of the elongate tubular member 114 removed to expose certain internal components of the plunger assembly 121. The plunger assembly 121 includes a plunging member 131, a button 118 that is pivotably coupled to a proximal end of the plunging member 131, and a spring 164 that is fixed to a distal end of the plunging member 131. The button 118 includes a coupling member 139 that is positioned within a complimentary slot 133 formed by the plunging member 131. A channel 135 extends along a circumferential surface of the coupling member 139 and is sized and positioned to guide the flexible elongate members 125 into the central lumen 119 of the elongate tubular member 114.

The flexible elongate members 125 are typically secured to the channel 135 with a biocompatible adhesive substance, such as a silicone adhesive. In some embodiments, the flexible elongate members 125 may be knotted at their ends. The knotted ends may be secured to the channel 135 with the biocompatible adhesive, may be tied around a narrowed section extending from the channel 135, or may be secured to a v-cut disposed on a surface of the channel 135. In some embodiments, the ends of the flexible elongate members 125 may be pinched between the channel 135 and another member extending from the channel 135 that is adapted to secure the flexible elongate members 125 to the channel 135.

The coupling member 139 of the button 118 can pivot within the complimentary slot 133 about an axis 149 that is substantially perpendicular to the longitudinal axis 144 of the elongate tubular member 114 (where the direction of the pivotal motion is denoted by the arrow shown in FIG. 4). The button 118 is typically rotatable to about 80° to about 100° with respect to the longitudinal axis 144 on either side of the elongate tubular member 114. Thus, the button 118 is typically rotatable through a total angle of about 160° to about 200°. In this manner, the button 118 can be operated to rotate the suture positioning member 117 located at the distal end region of the elongate tubular member 114, as will be discussed in more detail below.

The distal end of the plunging member 131 is further coupled to the internal shaft 168, such that axial movement of the plunging member 131 causes axial movement of the internal shaft 168. In this manner, the thumb button 118 can be operated to expand and collapse the expandable member 116, as will be discussed in more detail below. The spring 164 applies an outward (extension) force to the plunging member 131 and thus biases the plunging member 131 (and accordingly the internal shaft 168) to a proximal position as shown in FIG. 4. While the button 118 is oriented in line with the longitudinal axis 144 of the elongate tubular member 114, the button 118 can be depressed by the user such that the plunging member 131 and the internal shaft 168 move distally within the central lumen 119 of the elongate tubular member 114. Distal movement of the internal shaft 168 causes distal movement of the distal base 156 that is coupled to the distal end of the internal shaft 168. As the plunging member 131 moves distally within the central lumen 119 of the elongate tubular member 114, the plunging member 131 depresses the spring 164 until the diameter of the central lumen 119 narrows to a value less than that of a diameter of the plunging member 131, thus preventing further distal movement of the plunging member 131.

Figure 5:
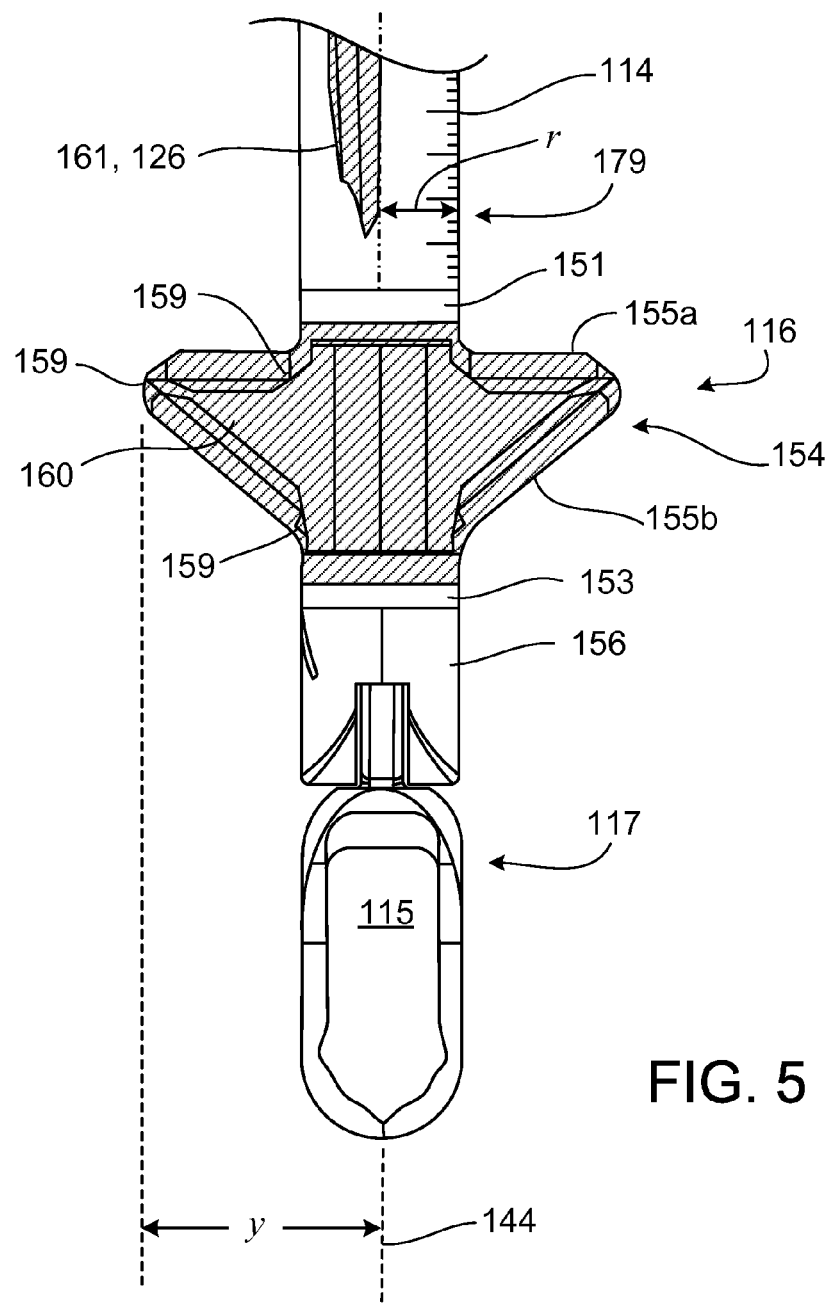
FIG. 5 is an enlarged, side view of the distal end region of the suture passer guide of FIG. 1, showing the suture positioning member in a neutral position and the expandable member in an expanded configuration.
Figure 6:
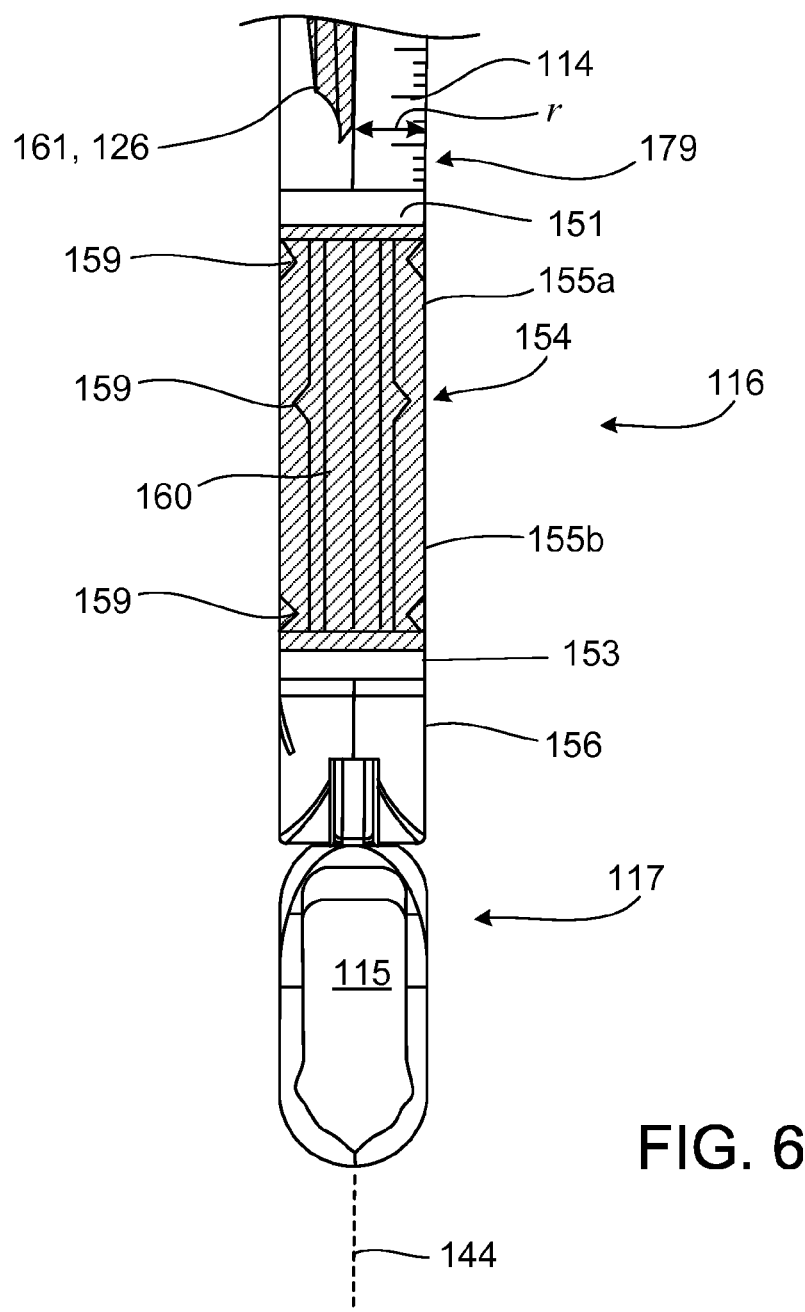
FIG. 6 is an enlarged, side view of the distal end region of the suture passer guide of FIG. 1, showing the suture positioning member in the neutral position and the expandable member in a collapsed configuration.

FIGS. 5 and 6 illustrate the distal end region of the suture passer guide 108 with the expandable member 116 in an expanded configuration and in a collapsed configuration, respectively. The expandable member 116 includes a proximal coupling member 151, a distal coupling member 153, and two collapsible arms 154. The proximal coupling member 151 can be in the form of a ring and is secured to the distal end of the elongate tubular member 114. Similarly, the distal coupling member 153 can be in the form of a ring and is secured to a distal end region of the distal base 156. The proximal and distal coupling members 151, 153 can, for example, be thermally bonded, adhesively bonded, or mechanically secured to the elongate tubular member 114 and to the distal base 156, respectively.

Each collapsible arm 154 includes a proximal segment 155a and a distal segment 155b. Thinned regions of the collapsible arms 154 are formed as living hinges 159, which couple the proximal coupling member 151 to respective proximal segments 155a of the collapsible arms 154, the proximal segments 155a of the collapsible arms 154 to respective distal segments 155b of the collapsible arms 154, and the distal segments 155b to the distal coupling member 153. The two collapsible arms 154 are spaced approximately 180° apart (as measured from centers of the collapsible arms 154) around a circumference of the expandable member 116 and provide circumferential gaps 137 (shown in FIGS. 2 and 3) between the collapsible arms 154.

The circumferential gaps 137 are positioned along the sides of the elongate tubular member 114 that form the openings 120, 126 and 122, 124 of the guide passages 136, 138. As a result, the circumferential gaps 137 are aligned with a direction in which the suture passer guide 108 would typically need to be tilted during use in order to better access an end of the suture to retrieve the suture from the surgical cavity. Such a geometry reduces the force required to tilt the suture passer guide 108 within the wound during use of the suture passer guide 108 as compared to the force that would be required to tilt an alternative suture passer guide including an expandable member having collapsible arms that form smaller circumferential gaps. Accordingly, the suture passer guide 108 can be more easily tilted within the surgical cavity if necessary to allow a distal end of a suture passer to be placed in close proximity to the end of the suture within the surgical cavity of a patient so that the suture passer can be used to grasp the end of the suture. The circumferential gaps extend from one collapsible arm 154 to the other collapsible arm 154 for about 90° to about 150° around the circumference of the expandable member 116, depending on a width of the collapsible arms 154. The collapsible arms 154 typically have a width of about 0.10 inch to about 0.40 inch (e.g., about 0.280 inch).

Still referring to FIGS. 5 and 6, an elastic film 160 surrounds the expandable member 116. A proximal end region of the film 160 is attached to the proximal coupling member 151 of the expandable member 116, and a distal end region of the film 160 is attached to the distal coupling member 153 of the expandable member 116 with an adhesive. The elastic film 160 can be formed of any of various materials that can stretch with the expandable member 116 as the expandable member 116 is expanded. It can also be beneficial to use a resilient material that substantially returns to its original size and shape when the expandable member 116 is collapsed. The elastic film 160 can, for example, be made of silicone and can have a thickness of about 0.005 inch to about to 0.010 inch. The elastic film 160 has a smooth surface that directly contacts the inner lining of the surgical wall during use. Thus, the film 160 can help to reduce the risk of tearing or otherwise damaging the lining during a procedure. In addition, the film 160 can be substantially gas impermeable and can help to ensure that gases, such as carbon dioxide ($CO_2$), within the surgical cavity do not escape from the surgical cavity through openings between the collapsible arms 154 of the expandable member 116. Thus, the elastic film 160 can help to prevent loss of inflation pressure within the surgical cavity (e.g., loss of pneumoperitoneum within an abdominal cavity) during use of the suture passer guide 108.

Referring to FIG. 5, when the internal shaft 168 and the distal base 156 are biased to their proximal positions (as shown in FIGS. 3 and 4), the expandable member 116 is provided in the expanded configuration in which the collapsible arms 154 extend radially a distance y substantially equidistant from the longitudinal axis 144 of the elongate tubular member 114 and greater than an outer radius r of the elongate tubular member 114.

The expanded configuration enables the expanded expandable member 116 of the suture passer guide 108 to be positioned against the inner lining of the surgical wall without the suture passer guide 108 sliding up through the port site wound. Because the internal shaft 168 is biased to a proximal position by the spring 164, the expandable member 116 is biased to the expanded configuration. As a result, with the button 118 released, the expandable member 116 can automatically expand as it exits the endoscopic port 102 and is passed into the surgical cavity during a procedure. The external surfaces of the collapsible arms 154 are substantially smooth to reduce the likelihood of the collapsible arms 154 tearing or otherwise damaging the inner lining of the surgical wall when the proximal arm segments 155a of the expanded expandable member 116 are brought into contact with the inner lining of the surgical wall.

As shown in FIG. 6, when the internal shaft 168 and the distal base 156 are moved a sufficient distance distally with respect to the elongate tubular member 114 (i.e., upon the user depressing the button 118 with sufficient force to overcome the proximal resistance provided by the spring 164), the expandable member 116 is caused to assume its collapsed configuration. In the collapsed configuration, the collapsible arms 154 are substantially flush with the sidewall of the elongate tubular member 114, such that the collapsible arms 154 do not extend substantially past the outer radius r of the elongate tubular member 114. In this manner, the expandable member 116 can fit within the central lumen 106 of the endoscopic port 102 to pass the suture passer guide 108 through the endoscopic port 102.

Figure 7:
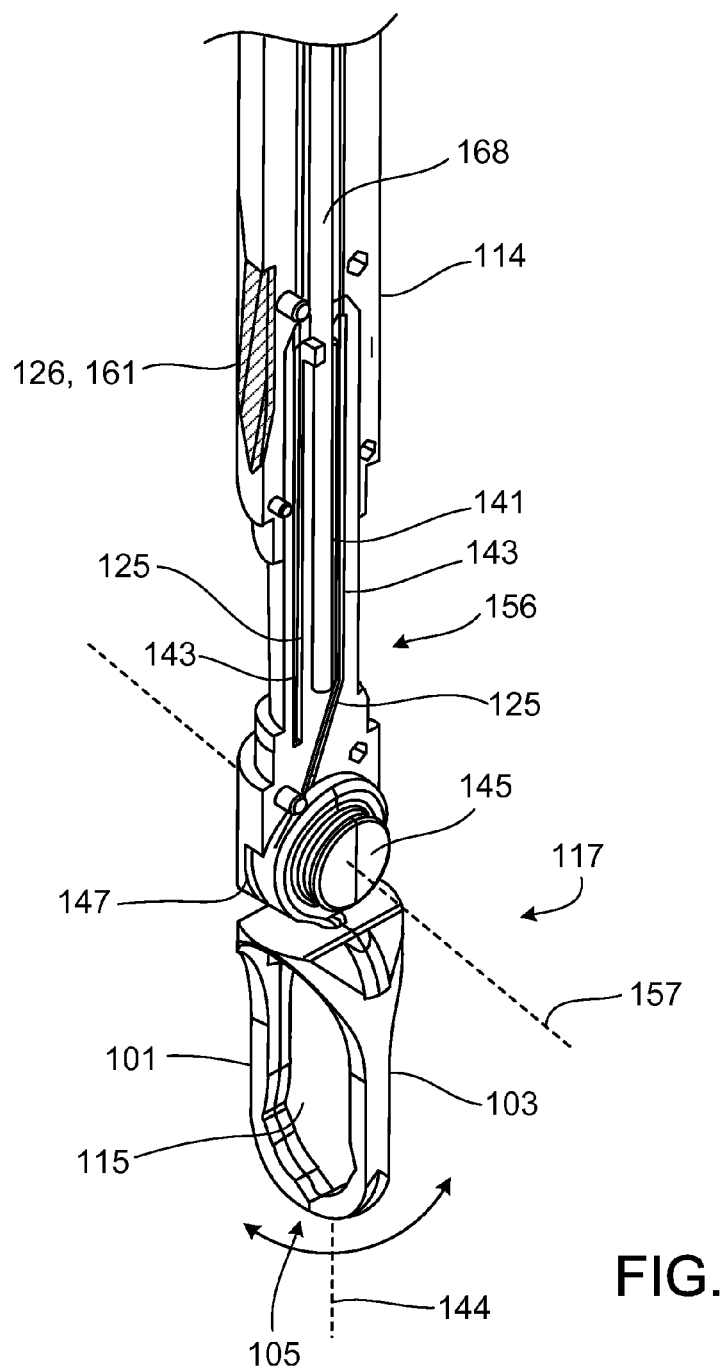
FIG. 7 is an enlarged, perspective view of the distal end region of the suture passer guide of FIG. 1, with one half of the elongate tubular member and one half of a distal base of the suture passer guide removed to show the connection between the suture positioning member and the distal base.

FIG. 7 illustrates an enlarged perspective view of the distal end region of the suture passer guide 108, with the collapsible arms 154 of the expandable member 116, one half of the elongate tubular member 114, and one half of the distal base 156 removed to show the distal base 156 coupled to the suture positioning member 117 and to the elongate tubular member 114. The suture positioning member 117 includes two flexible arms 101, 103 that define the aperture 115. The flexible arms 101, 103 are connected to a coupling member 145 that extends from a proximal end of the suture positioning member 117. The flexible arms 101, 103 contact one another at a proximal tip 105 of the aperture 115 and are configured to flex open at the proximal tip 105 upon being forced open by a suture passing through a slot formed between the flexible arms 101, 103 at the proximal tip 105. The flexible arms 101, 103 typically have a width of about 1 mm to about 4 mm (e.g., about 1.5 mm).

Still referring to FIG. 7, the distal base 156 includes a central channel 141 sized to receive the distal end of the internal shaft 168 and two guide channels 143 located within opposite sides of the distal base 156. The guide channels 143 are sized to receive the respective flexible elongate members 125 and extend to the coupling member 145. The flexible elongate members 125 are disposed within the channels 143 and are secured to the coupling member 145. Typically, the flexible elongate members 125 are secured to the coupling member 145 with a biocompatible adhesive substance, such as a silicone adhesive. In some embodiments, the flexible elongate members 125 may be knotted at their ends. The knotted ends may be secured to the coupling member 145 with the biocompatible adhesive, may be tied around a narrowed section extending from coupling member 145, or may be secured to a v-cut disposed on a surface of the coupling member 145. In some embodiments, the ends of the flexible elongate members 125 may be pinched between the coupling member 145 and another member extending from the coupling member 145 that is adapted to secure the flexible elongate members 125 to the coupling member 145. The distal base 156 further defines a slot 147 formed to allow pivotal motion of the coupling member 145.

As the button 118 (shown in FIG. 4) is rotated to the left side of the elongate tubular member 114, the flexible elongate member 125 extending from a right side of the coupling member 139 (shown in FIG. 4) to a left side of the coupling member 145 is moved proximally, and the flexible elongate member 125 extending from a left side of the coupling member 139 to a right side of the coupling member 145 is moved distally. In this manner, the flexible elongate members 125 cause the suture positioning member 117 to rotate to the left side of the elongate tubular member 114 (as indicated by the arrow in FIG. 7) and about an axis 157 that is substantially perpendicular to the longitudinal axis 144 of the elongate tubular member 114. As the button 118 is rotated to the right side of the elongate tubular member 114, the flexible elongate member 125 extending from the left side of the coupling member 139 to the right side of the coupling member 145 is shifted proximally, and the flexible elongate member 125 extending from the right side of the coupling member 139 to the left side of the coupling member 145 is shifted distally. In this manner, the flexible elongate members 125 cause the suture positioning member 117 to rotate to the right side of the elongate tubular member 114 (as indicated by the arrow in FIG. 7) and about the axis 157. The suture positioning member 117 is typically rotatable to about 80° to about 100° with respect to either side of the elongate tubular member 114, and thus, the suture positioning member 117 is typically rotatable through an entire angle of about 160° to about 200°.

As noted above, the suture positioning member 117 defines an aperture 115 sized to receive a suture passer and a suture so that the suture passer can deliver an end of the suture through the aperture 115 while the suture positioning member 117 is rotated to one side of the elongate tubular member 114 and can subsequently reposition the end of the suture on the other side of the elongate tubular member 114. The aperture 115 typically has a length of about 0.50 inch to about 1.2 inches (e.g., about 0.90 inch) and a width of about 0.2 inch to about 0.4 inch (e.g., about 0.26 inch).

As shown in FIGS. 1, 2, and 5-7, the suture passer guide 108 also includes self-sealing elastic plugs 161 disposed within the distal openings 124, 126. When the suture passer is passed through one of the guide passages 136, 138 and exits the distal opening 124, 126 that is associated with that guide passage and is plugged with the elastic plug 161, the suture passer punctures the elastic plug 161. As the suture passer is inserted through the elastic plug 161, the elastic plug 161 forms a seal around the outer surface of the suture passer. Following the removal of the suture passer from the elastic plug 161, the elastic plug 161 seals the hole in which the suture passer was disposed. The inclusion of the elastic plugs 161 within the distal openings 124, 126 and the self-sealing properties of the elastic plugs 161 can prevent loss of inflation pressure within the surgical cavity (e.g., loss of pneumoperitoneum within the abdominal cavity) during use of the suture passer guide 108, such that the surgical cavity does not need to be re-insufflated following use of the suture passer guide 108. The elastic plugs 161 are typically made of silicone or polyphenol ether (PPE). However, other self-sealing materials can alternatively or additionally be used.

As shown in FIGS. 1, 5, and 6, the external surface of the elongate tubular member 114 includes a set of ruler markings 179 that increase in value from the distal end of the elongate tubular member 114 toward the proximal end of the elongate tubular member 114. While the expandable member 116 is expanded and positioned along the lining of the surgical cavity wall, the ruler markings 179 serve to indicate a thickness of the surgical cavity wall, which may be recorded in a patient chart for determining a prognosis or potentially performing statistical analyses.

Referring briefly again to FIGS. 1 and 2, the suture passer guide 108 further includes two opposing round depressions 181 that provide finger gripping surfaces near the proximal end of the elongate tubular member 114. Alternatively, the depressions 181 can have any of various other shapes that enhance gripability. The proximal end region of an elongate tubular member may alternatively or additionally include rings formed on the external surface of the elongate tubular member near the proximal end of the elongate tubular member. The rings may provide the proximal end region of a suture passer guide with added grip to make it easier for the surgeon to grasp the suture passer guide and insert it into the endoscopic port 102. As an alternative to or in addition to rings, a proximal end region of an elongate tubular member can include other types of textured surfaces that improve the ability of the surgeon to grip the suture passer guide. Such textured surfaces can be particularly beneficial when the surgeon's gloves are wet or otherwise lubricated.

The suture passer guide 108, as explained above, has a length that is sufficient to allow the expandable member 116 and the suture positioning member 117 to extend distally beyond the endoscopic port 102 while the proximal end region of the suture passer guide 108 including the button 118 remains proximal to the endoscopic port 102. The suture passer guide 108 typically has a length of about 8.0 inches to about 12.0 inches (e.g., about 8.5 inches). Typically, the suture passer guide 108 (e.g., the elongate member 114 of the suture passer guide 108) has a diameter of about 5 mm to about 15 mm (e.g., about 10 mm). It should be understood, however, that the suture passer guide 108 can have different dimensions, depending on the size of the endoscopic port 102 with which it is to be used.

The various components of the suture passer guide 108, including the elongate tubular member 114, the expandable member 116, the internal shaft 168, and the suture positioning member 117 can be formed of one or more of a variety medical grade materials, including stainless steel, titanium, polycarbonate, Acrylonitrile butadiene styrene (ABS), polypropylene, acrylic, liquid crystal polymer (LCP), polyetheretherketone (PEEK), silicone, and thermoplastic elastomer (TPE). In some embodiments, the elongate tubular member 114 is made of polypropylene. In certain embodiments, the internal shaft 168 is made of stainless steel, polycarbonate, and/or another suitably stiff, strong material.

The endoscopic port 102 typically includes one or more seals, such as o-rings (i.e., elastic, flat washer-shaped rings), that surround the elongate tubular member 114 when the elongate tubular member 114 is disposed within the central lumen 106 of the endoscopic port 102. The seals and the elongate tubular member 114 are configured so that a substantially fluid-tight seal is formed between the inner surfaces of the seals and the outer surface of the elongate tubular member 114. For example, the inner diameter of the seals of the endoscopic port 102, in their undeformed state, will typically be equal to or slightly less than the outer diameter of the elongate tubular member 114. As a result, gases within a surgical cavity can be prevented from escaping through the central lumen 106 while the suture passer guide 108 is disposed within the central lumen 106 of the endoscopic port 102 and the distal end of the endoscopic port 102 is positioned in the surgical cavity.

Figure 8:
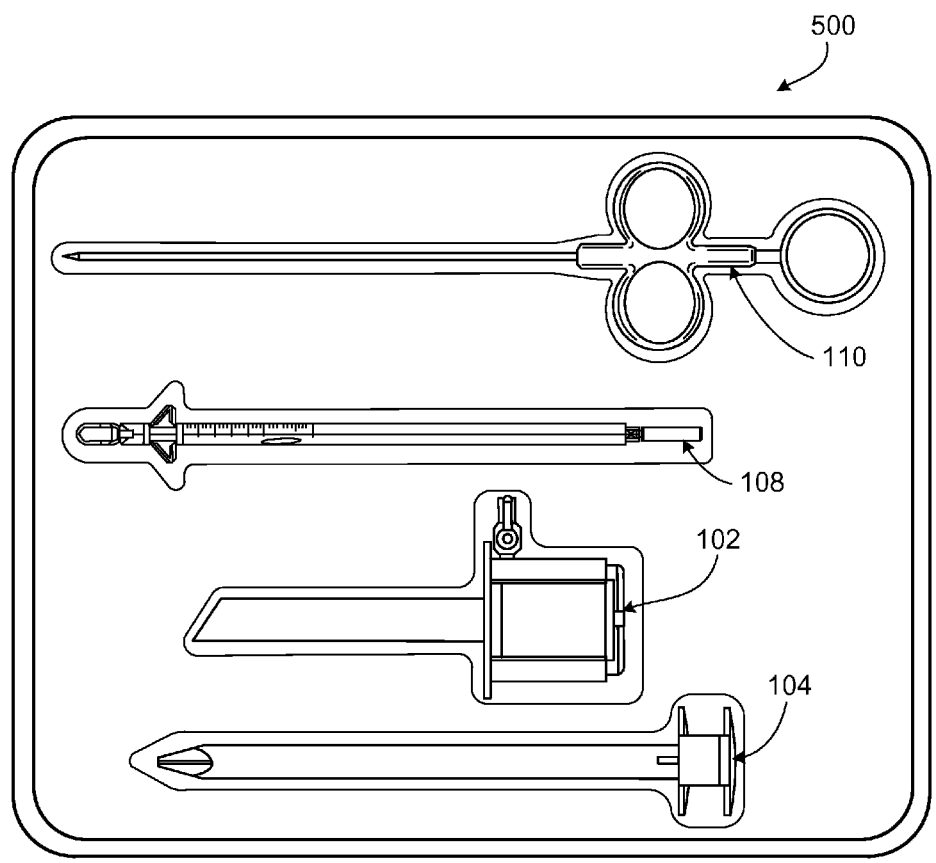
FIG. 8 illustrates an endoscopic surgical kit that includes an obturator, a suture passer, and the endoscopic port and suture passer guide of FIG. 1.

FIG. 8 illustrates an endoscopic surgical kit 500 that includes the endoscopic port 102, the suture passer guide 108, an obturator 104, and a suture passer 110. The kit 500 can be used to perform various types of endoscopic surgical procedures.

FIGS. 9A-9J schematically illustrate a method of using the endoscopic surgical kit 500 to perform a laparoscopic surgical procedure in an abdominal cavity 180 of a patient and to subsequently repair an endoscopic port wound 183 used to access the patient's abdominal cavity 180. As shown in FIG.

9A, to perform the laparoscopic surgical procedure, the obturator 104 is positioned within the central lumen 106 of the endoscopic port 102 such that a sharp piercing tip 112 of the obturator 104 extends beyond a distal end of the endoscopic port 102. The endoscopic port 102 and the obturator 104 (often referred to in combination as a trocar) are then pushed through the abdominal wall of the patient, which includes an external skin layer 184, a relatively thick fatty layer 182, a fascia layer 194, and a peritoneum 186, until the tip 112 of the obturator 104 and the distal end of the endoscopic port 102 are positioned within the abdominal cavity 180 of the patient, thereby creating the port site wound 183 within the abdominal wall of the patient.

The obturator 104 is subsequently removed from the central lumen 106 of the endoscopic port 102, leaving the endoscopic port 102 positioned within the port site wound 183 and protruding into the abdominal cavity 180. Cameras and other surgical instruments are then inserted through the central lumen 106 for viewing internal organs and carrying out the surgical procedure within the abdominal cavity 180. The endoscopic port 102 includes seals that substantially prevent gases from escaping from the abdominal cavity 180 via the central lumen 106 of the endoscopic port 102 during the procedure. As a result, the inflation pressure (i.e., pneumoperitoneum) of the abdominal cavity 180 can be maintained while the endoscopic port 102 is positioned in the port site wound.

Figure 9A:
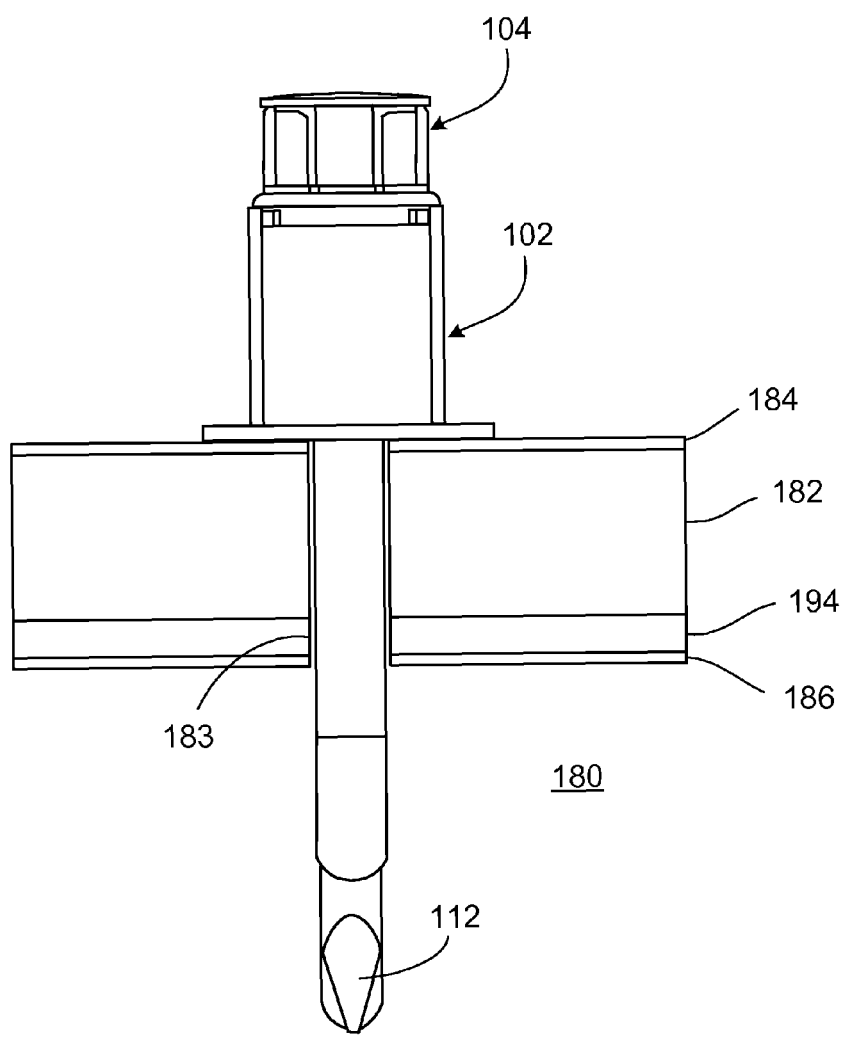
FIGS. 9A-9J schematically illustrate a method of performing a laparoscopic surgery and using the suture passer guide of FIG. 1 to repair an endoscopic port site wound.
Figure 9B:
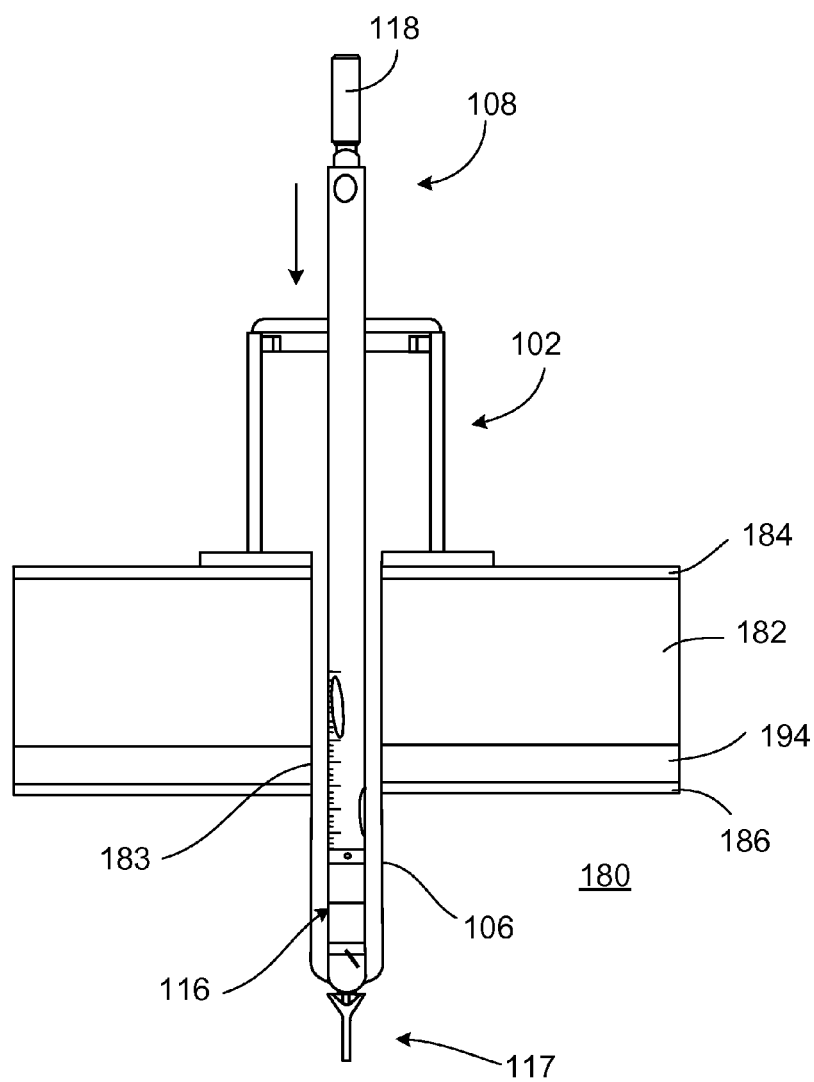

After completing the surgical procedure within the abdominal cavity 180, the suture passer guide 108 is inserted through the central lumen 106 of the endoscopic port 102 and into the abdominal cavity 180 in order to facilitate repair of the port site wound 183, as shown in FIG. 9B. To insert the suture passer guide 108 through the central lumen 106 of the endoscopic port 102, the button 118 is first depressed to collapse the expandable member 116. The suture passer guide 108 is then inserted into the central lumen 106 of the endoscopic port 102. Once the collapsed expandable member 116 is positioned within the central lumen 106 of the endoscopic port 102, the button 118 can be released as the user continues to pass the suture passer guide 108 distally through the lumen 106 toward the abdominal cavity 180 of the patient. The sidewalls of the obturator 102 retain the expandable member 116 in the collapsed configuration as the suture passer guide 108 is passed through the lumen 106. Because the endoscopic port 102 is not vacated from the port site wound prior to positioning the suture passer guide 108 in the port site wound 183 and the abdominal cavity 180, the port site wound 183 is not left open in a manner that would allow it to freely release large volumes of insufflation gases from the abdominal cavity 180.

Figure 9C:
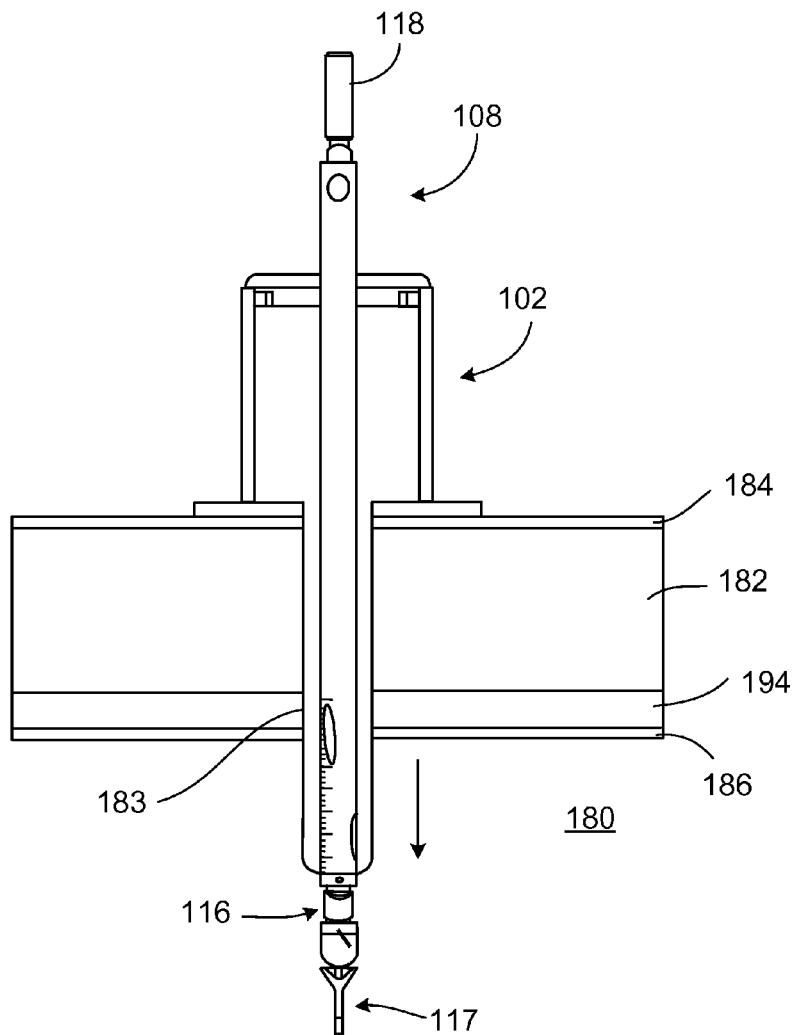

Referring to FIG. 9C, when the expandable member 116 is passed distally beyond the distal end of the endoscopic port 102, the expandable member 116 automatically expands. In this expanded configuration, the expandable member 116 has a diameter that exceeds the diameter of the endoscopic port 102 and the port site wound 183. It will be understood that the collapsible arms 154 of the expandable member 116 extend radially into and out of the plane of the paper in the view shown in FIG. 9C.

Figure 9D:
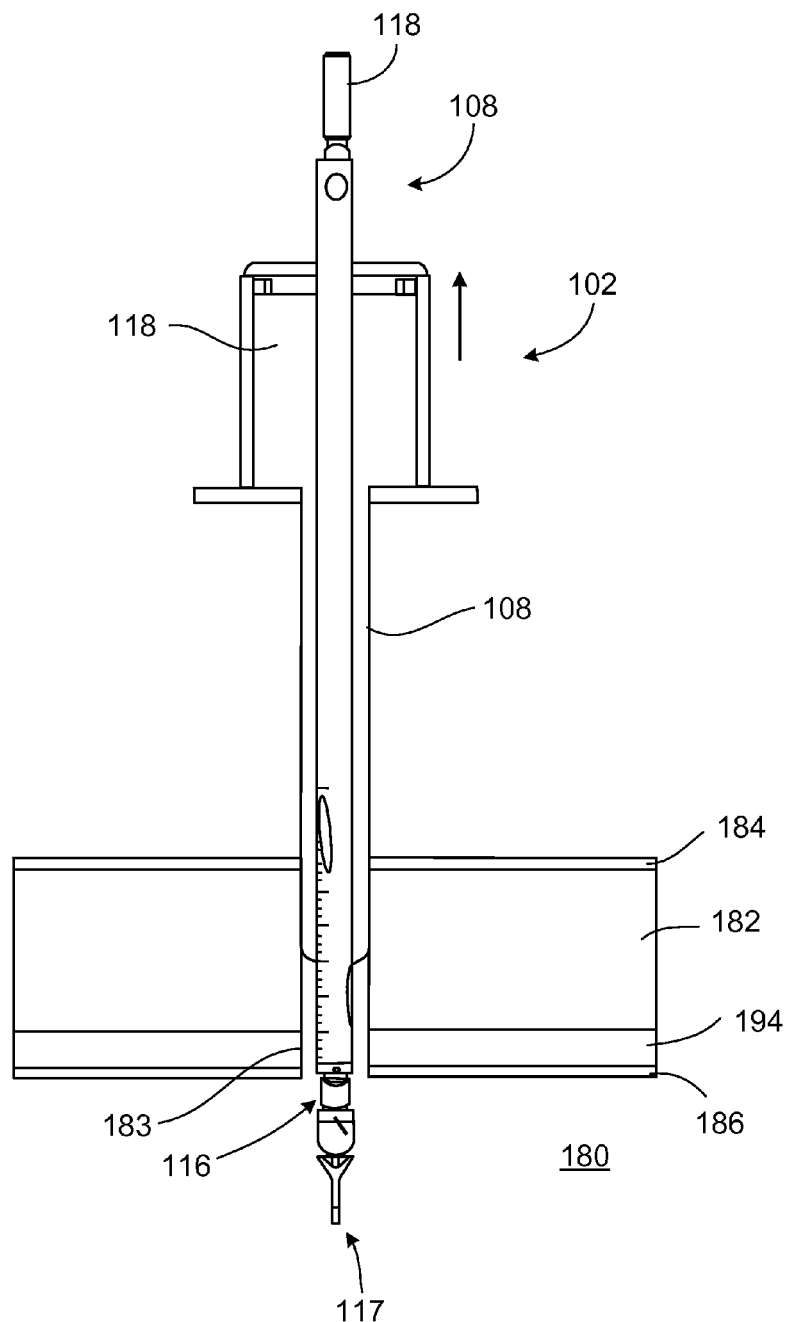

With the expandable member 116 in its expanded configuration, the endoscopic port 102 is then removed from the wound by pulling proximally on the proximal end region of the endoscopic port 102, as shown in FIG. 9D. As the endoscopic port 102 is removed from the port site wound, the expanded expandable member 116 contacts the inner lining of the patient's abdominal cavity (i.e., the patient's peritoneum 186), thereby preventing the suture passer guide 108 from being pulled out of the port site wound 183 along with the endoscopic port 102. Because the collapsible arms 154 of the expandable member 116 extend radially into and out of the plane of the paper in the view shown in FIG. 9D and the tissue of the patient is shown in cross-section, the contact between the expandable member 116 and the peritoneum 186 cannot be seen in FIG. 9D. However, it will be readily understood that the upper surfaces of the proximal segments 155A of the collapsible arms 154 of the expandable member 116 (shown in FIG. 5) are in contact with the peritoneum in the configuration illustrated in FIG. 9D.

After the endoscopic port 102 has been removed from the port site wound 183, the tissue surrounding the wound 183 collapses against the outer surface of the suture passer guide 108, creating a partial seal that inhibits insufflation gases (e.g., $CO_2$) within the abdominal cavity 180 from escaping through the port site wound such that the inflation pressure within the abdominal cavity 180 (i.e., the pneumoperitoneum within the abdominal cavity) is substantially maintained.

Figure 9E:
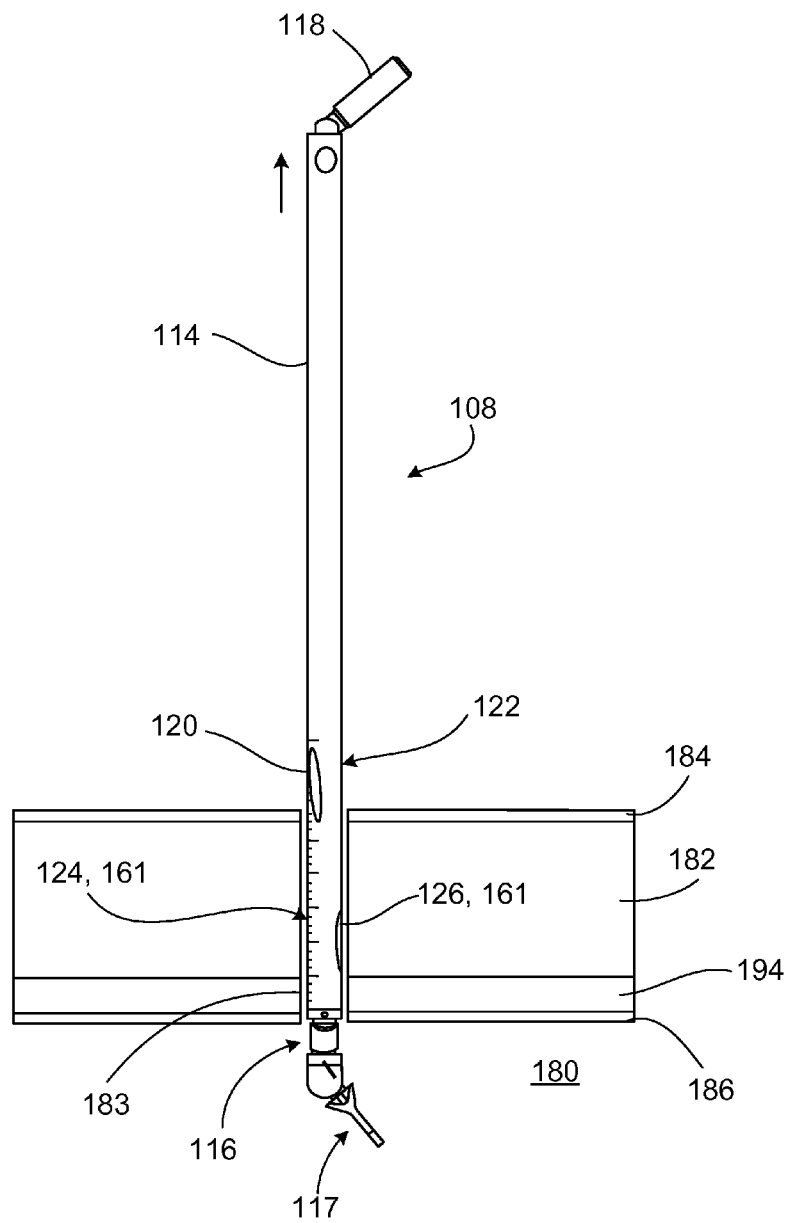

Referring to FIG. 9E, prior to inserting the suture passer 110 through the suture passer guide 108 to suture the port site wound 183, the user applies a proximal force to the suture passer guide 108 (i.e., by pulling upward on the elongate tubular member 114 in the view shown in FIG. 9E) to ensure that the expanded expandable member 116 is in contact with the peritoneum 186. In this position, the distal openings 124, 126 of the guide passages 136, 138 are located at known distances from the peritoneum 186. Accordingly, positioning the expandable member 116 against the peritoneum 186 helps to position the suture passer guide 108 in the desired location within the wound 183 for optimal passage of the suture passer 110. In addition to ensuring that the distal openings 124, 126 are located in the desired positions, the application of the proximal force to the suture passer guide 108 can also help to maintain the pneumoperitoneum within the abdominal cavity 180. In particular, the film 160 (shown in FIGS. 5 and 6) surrounding the expandable member 116 is pulled against the peritoneum 186, which can create a partial seal that helps to prevent $CO_2$ and other gases within the abdominal cavity 180 from escaping through the port site wound.

Prior to inserting the suture passer 110 through the suture passer guide 108, the button 118 is rotated to the right side of the suture passer guide 108 causing the suture positioning member 117 to also rotate to the right side of the suture passer guide 108. Typically, the button 118 and the suture positioning member 117 are rotated about 45° to about 100° (e.g., about 45°) relative to the longitudinal axis 144 of the elongate tubular member 114. In the rotated position, the aperture 115 of the suture positioning member 117 can receive the suture passer 110 as it passes into the abdominal cavity 180 to the right side of the suture passer guide 108.

Figure 9F:
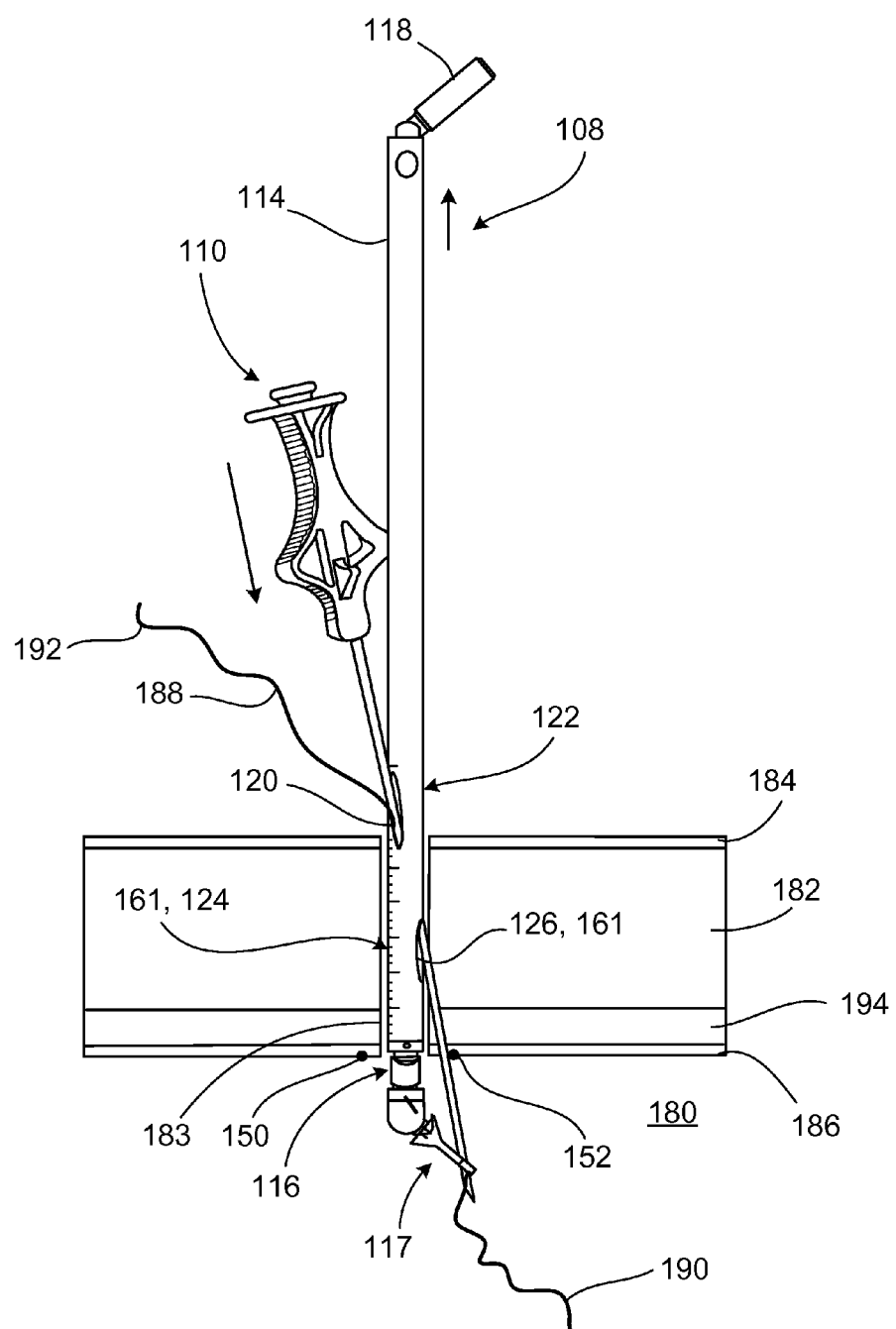

Referring now to FIG. 9F, the suture passer 110 is then loaded with a suture 188 such that a first end 190 of the suture 188 extending from a distal end region of the suture passer 110 has a length sufficient to accommodate placement of the first end 190 of the suture 188 within the aperture 115 of the suture positioning member 117 while the suture positioning member 117 is rotated to one side of the suture passer guide 108, as well as to accommodate repositioning of the first end 190 of the suture 188 upon rotating the suture positioning member 117 to the opposite side of the suture passer guide while the suture 188 is disposed within the aperture 115 of the suture positioning member 117. Typically, the length of the suture 188 extending from the suture passer 110 is about 1 inch to about 3 inches. The suture passer 110 is then inserted into the left proximal opening 120, through the guide passage 136, and out of the right distal opening 126 such that the suture passer 110 punctures the peritoneum 186 at the right puncture point 152, which is laterally spaced from the expanded expandable member 116 (i.e., spaced from the expanded expandable member 116 in a direction that is perpendicular to the longitudinal axis of 144 of the elongate member 114). In this manner, the first end 190 of the suture 188 is carried into the abdominal cavity 180 along with the distal end of the suture passer 110. Due to the geometry of the guide passage 136 and the configuration of the expandable member 116, the suture passer 110 remains laterally spaced from the expanded expandable member 116 as the suture passer 110 passes along the length of the expanded expandable member 116. As a result, interference between the suture passer 110 and the expanded expandable member 116 is avoided. The distal end of the suture passer 110 and the grasped suture 188 are then advanced through the aperture 115 of the suture positioning member 117.

As the suture passer 110 is delivered through the suture passer guide 108 and into the abdominal cavity 180, the surgeon applies a proximal force to the suture passer guide 108, which causes the expanded expandable member 116 to apply an outward force to the peritoneum 186. This outward force on the peritoneum 186 can make it easier to pass the tip of the suture passer 110 through the peritoneum 186 in a smooth manner. The self-sealing plug 161 disposed within the distal opening 126 forms a fluid-tight seal with the suture passer 110 and thus prevents any gases that might have entered the wound 183 from escaping to atmosphere via the guide passage 136. The suture 188 is sufficiently long that a second end 192 of the suture 188 remains external to the abdominal cavity 180. After depositing the first end 190 of the suture 188 in the abdominal cavity 180, the suture 188 is released, and the suture passer 110 is removed from the guide passage 136. Due to the resilience of the self-sealing plug 161 disposed within the distal opening 126, a fluid-tight seal is maintained once the suture passer 110 has been removed from the plug 161. Thus, any gases that might have entered the wound 183 may still prevented from escaping to atmosphere via the guide passage 136 by the plug 161. Insertion of the suture 188 into the abdominal cavity 180 in this manner is typically viewed via video generated by a camera inserted into the abdominal cavity 180 through another endoscopic port positioned within the abdominal wall. However, due to the alignment of the guide passage 136 with the aperture 115 of the suture positioning member 117, there is typically no need to use a camera (e.g., an endoscope) to achieve properly alignment of the suture passer 110 with the aperture 115 of the suture positioning member 117.

Figure 9G:
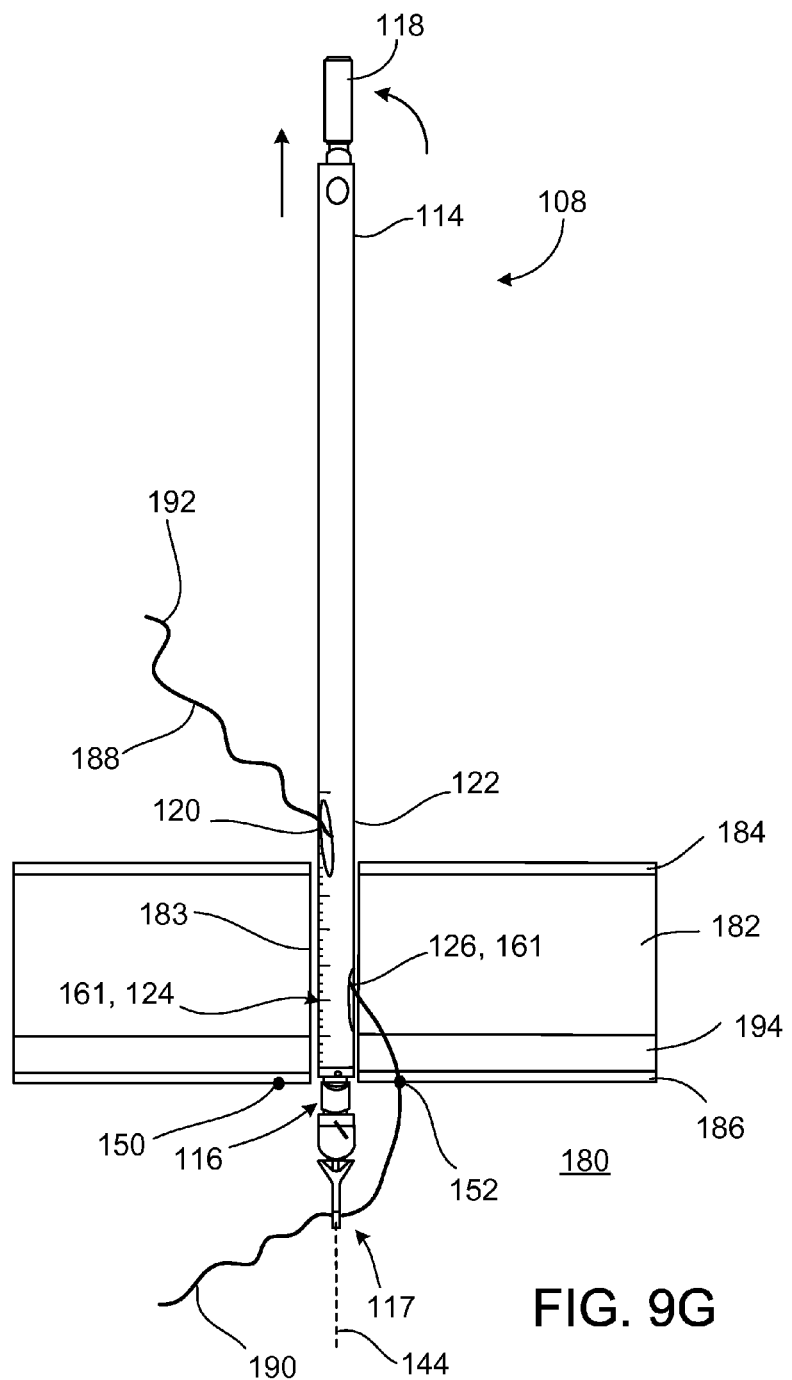
Figure 9H:
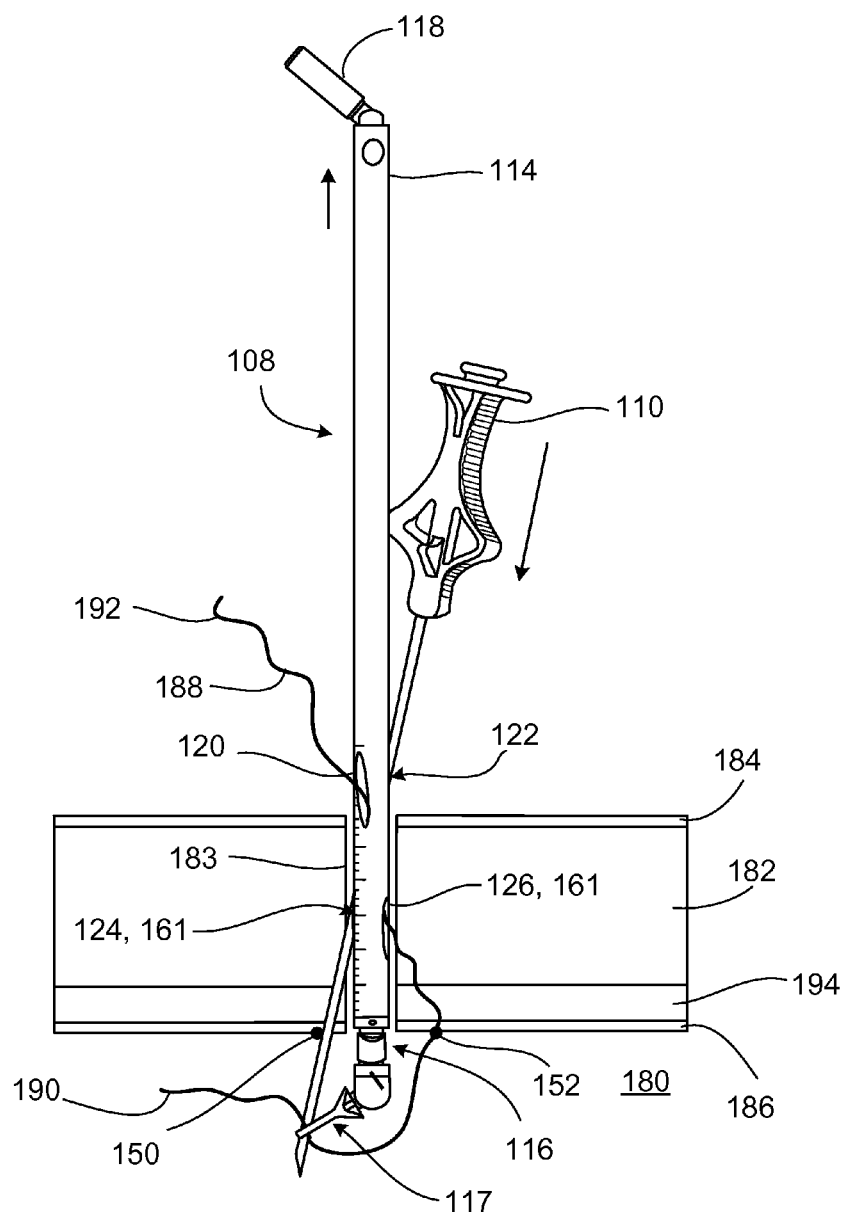

Referring to FIG. 9G, after the suture 188 has been deposited within the aperture 115 of the suture positioning member 117, the button 118 is rotated from the right side of the suture passer guide 108 to a neutral position in which the button 118 is oriented in line with the longitudinal axis 144 of the elongate tubular member 114, thereby causing the suture positioning member 117 to rotate to a position in line with the longitudinal axis 144 of the elongate tubular member 114. The button 118 is further rotated from the neutral position to the left side of the suture passer guide 108, as shown in FIG. 9H, such that the suture positioning member 117 is rotated from the neutral position to the left side of the suture passer guide 108. Typically, the button 118 and the suture positioning member 117 are rotated through an angle of about 90° to about 200° (e.g., about 90°) from the right side of the suture passer guide 108 to the left side of the suture passer guide. In this manner, the first end 190 of the suture 188 is carried within the aperture 115 of the suture positioning member 117 to the left side of the suture passer guide 108 and in proximity to the left distal opening 124.

Still referring to FIG. 9H, the suture passer 110 is then inserted into the right proximal opening 122, through the guide passage 138, and out of the left distal opening 124 such that the suture passer 110 punctures the peritoneum 186 at the left puncture point 150. The suture passer 110 is advanced into the aperture 115 of the suture positioning member, and the suture 188 is then grasped with the suture passer 110.

While the suture positioning member 117 has been described as being rotated to the left side of the suture passer guide 108 prior to inserting the suture passer guide 110 through the second guide passage 138 and into the surgical cavity, in some examples, the suture passer 110 is inserted through the second guide passage 138 prior to rotating the suture positioning member 117 from the right side of the suture passer guide 108 to the left side of the suture passer guide 108.

Suture passer guides that do not include suture positioning members at their distal ends may not have the capability of easily positioning a suture in proximity to a distal opening of a guide passage. As a result, such suture passer guides may need to be significantly tilted within a wound in order to more accurately guide a distal end of a suture passer to a location within grasping proximity of the suture, and a user may need to probe the surgical cavity with the distal end of the suture passer in order to grasp the suture. In contrast, use of the suture passer guide 108 can prevent or significantly reduce the need to tilt the suture passer guide 108 within the wound 183 for the suture passer 110 to easily grasp the first end 190 of the suture 188. Further, the arrangement of the expandable member 116 (i.e., the large circumferential gaps 137 between the collapsible arms 154) improves the ease with which the suture passer guide 108 can be tilted if necessary. As a result, any tissue damage that might otherwise result from significantly tilting a suture passer guide within a wound and using a suture passer to probe a surgical cavity for a suture can be substantially avoided or minimized.

Figure 9I:
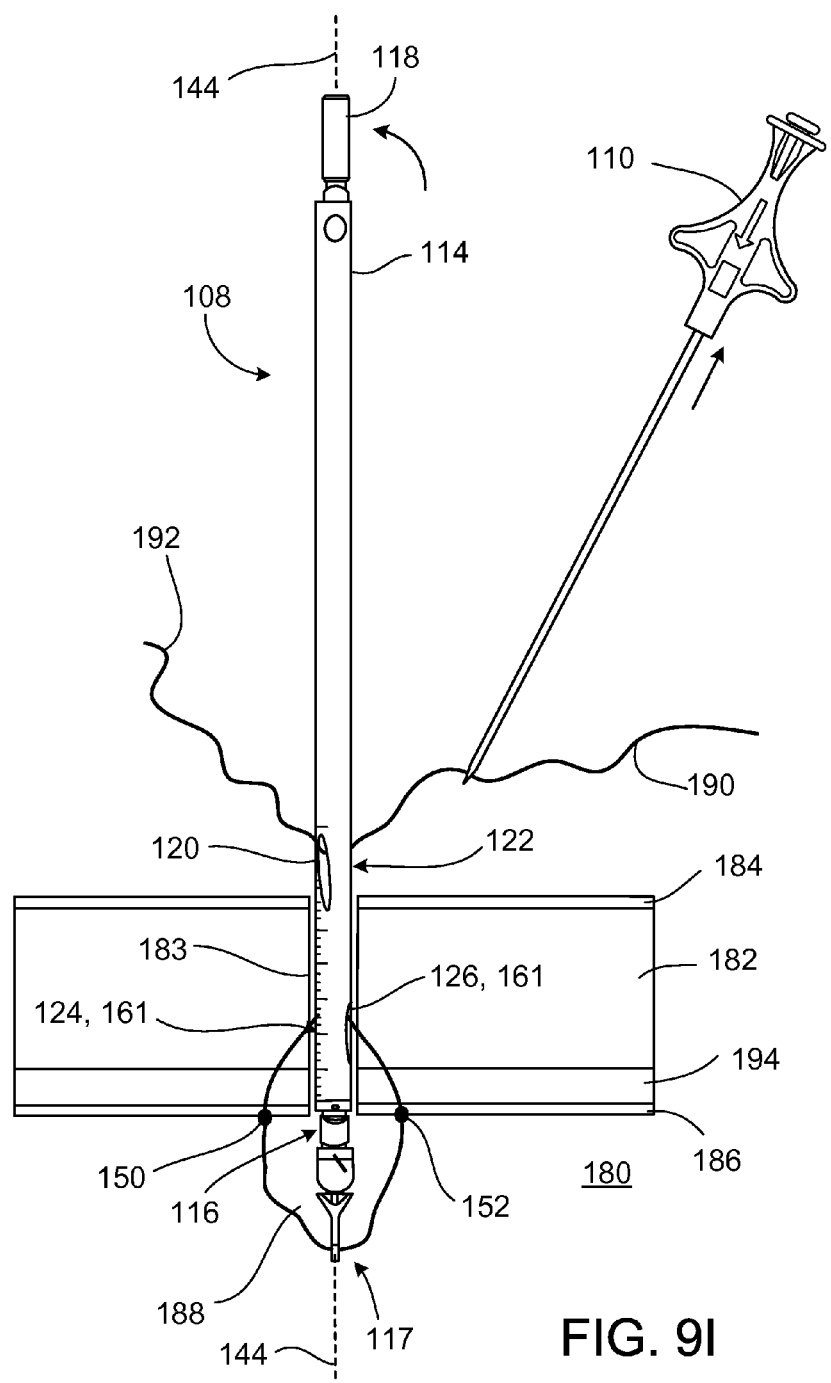

As shown in FIG. 9I, with the suture 188 in its grasp, the suture passer 110 is then removed from the guide passage 138, while the suture 188 remains disposed within the aperture 115 of the suture positioning member 117. The first end 190 of the suture 188 is pulled through the various tissue layers 186, 194, 182, 184 of the abdominal wall and outside of the patient. At this point, the first and second ends 190, 192 of the suture 188 are both positioned outside of the patient.

Figure 9J:
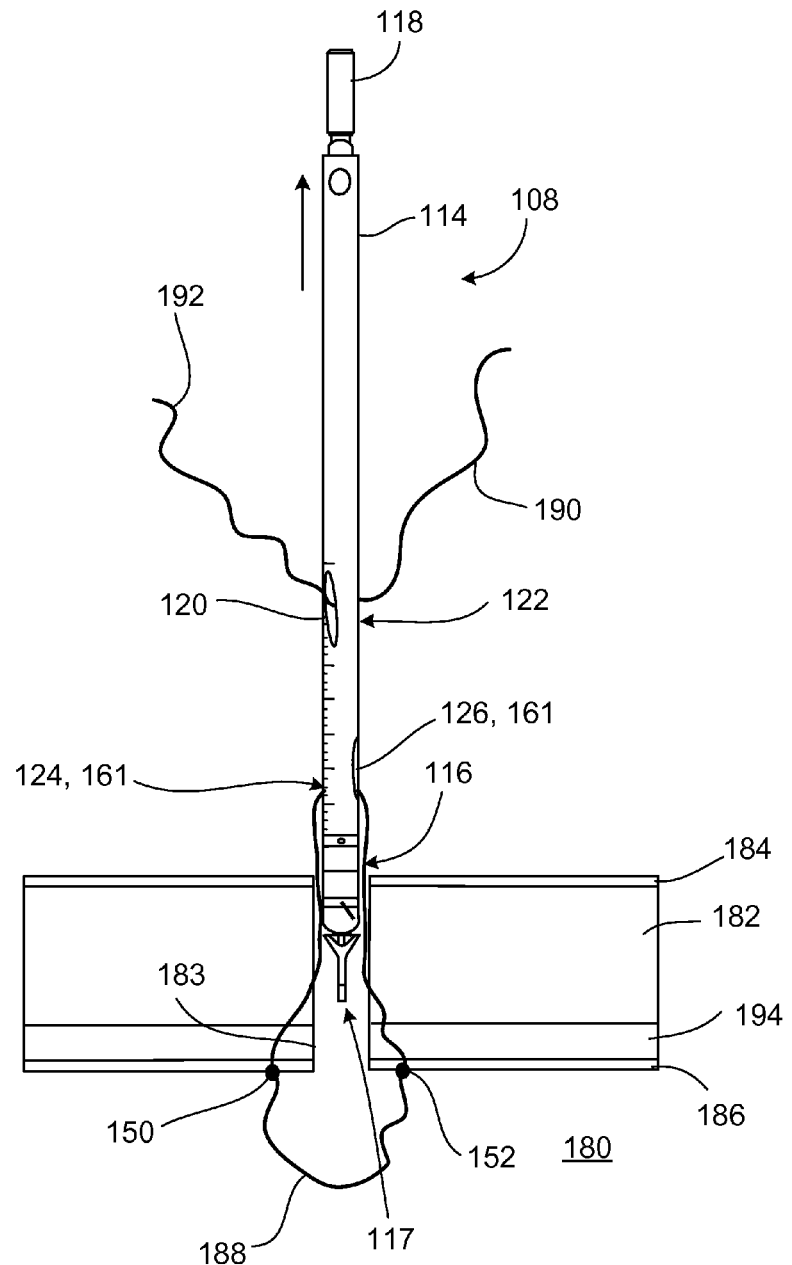

Referring to FIG. 9J, with the suture 188 positioned within the tissue in this manner and the button 118 and suture positioning member 117 in their neutral positions, the button 118 is depressed to collapse the expandable member 116, and the suture passer guide 108 is pulled out of the port site wound 183. As the suture passer guide 108 is pulled out of the port side wound 183, a portion of the suture 188 disposed within the aperture 115 of the suture positioning member 117 contacts and applies a force to the proximal tip 105 of the aperture 115, causing the flexible arms 101, 103 to open at the proximal tip 105 and thus allow the suture 188 to pass through the opening and remain in the abdominal cavity 180. The flexible arms 101, 103 snap shut at the proximal tip 105 of the aperture 115 after the suture 188 passes through the opening. The smooth outer surfaces of the elongate tubular member 114, the collapsed expandable member 116, and the neutrally positioned suture positioning member 117 help to ensure that the tissue adjacent the port site wound 183 is not torn or otherwise damaged as the suture passer guide 108 is removed from the port site wound 183.

After removing the suture passer guide 108 from the port site wound 183, the first and second ends 190, 192 of the suture 188 are tied to form a knot. The knot is positioned at a location proximal to the fascia 194, such that the fascia 194 and peritoneum 186 are substantially closed. Due to the controlled placement of the suture 188 within the patient's tissue (e.g., the controlled suture bite) afforded by the use of the suture passer guide 108, the fascia 194 and peritoneum 186 are encompassed in a relatively smooth mass closure underneath the external skin layer 184 to produce a high quality port site wound repair.

Surgical procedures including the wound closure procedure described above can typically be carried out in less time than those that require the endoscopic port 102 to be removed before inserting a suture passer guide. For example, repositioning the first end 190 of the suture 188 within the abdominal cavity 180 for easy retrieval using the suture positioning member 117 can substantially eliminate or reduce the time that would otherwise be required to significantly tilt a suture passer guide for guidance of the distal end of the suture passer 110 to a position within proximity to the first end 190 of the suture 188 or to use the suture passer 110 to probe the abdominal cavity 180 for the first end 190 of the suture 188. In addition, inserting the suture passer guide 108 through the endoscopic port 102 inhibits the loss of pneumoperitoneum and thus eliminates the time that might otherwise be required to re-insufflate the abdominal cavity following removal of the endoscopic port 102. Furthermore, inserting the suture passer guide 108 through the endoscopic port 102 removes the need to relocate the port site wound following removal of the endoscopic port 102, which is required when using a type of suture passer guide that is inserted directly into the port site wound and can be quite time consuming. In addition, by inserting the suture passer guide 108 through the endoscopic port 102, additional tissue damage that might otherwise result from inserting a suture passer guide directly into the wound can be avoided.

While the suture passer guide 108 has been described as including the suture positioning member 117 that forms the aperture 115 for receiving and repositioning a suture, in some embodiments, a suture passer guide alternatively includes a suture positioning member that has a set of resilient fingers (e.g., jaws). In such embodiments, the fingers of the suture positioning member are configured to grasp the suture upon the suture being delivered into a surgical cavity by a suture passer. Upon grasping the suture, the fingers can be pivoted to reposition the suture for retrieval from the surgical cavity by the suture passer. The fingers may be made of one or more medical grade materials, such as polycarbonate, polypropylene, or another suitable medical grade plastic.

While the suture passer guide 108 has been described as having an actuator that includes a plunger assembly 121 having a button 118 adapted to rotate or pivot about the pivot axis 149 (shown in FIG. 4), which is substantially perpendicular to the longitudinal axis 144 of the elongate tubular member 114, in some embodiments, the suture passer guide includes an actuator having a plunger assembly with a knob that is rotatable about the longitudinal axis of the elongate tubular member. In some such embodiments, the knob is adapted to move axially within the elongate tubular member of the suture passer guide (as does the button 118) and adapted to rotate about the longitudinal axis of the elongate tubular member. In such embodiments, rotating the knob about the longitudinal axis of the elongate tubular member may accordingly cause rotation of the suture positioning member 117 about the pivot axis 157 (shown in FIG. 7). For example, a set of proximal gears may couple the rotatable knob to the flexible elongate members 125, and a set of distal gears may couple the flexible elongate members 125 to the suture positioning member 117. Such a configuration of the proximal and distal gears can allow rotation of the knob to cause rotation of the suture positioning member 117. In some embodiments, a graphic may be disposed on a surface of the knob to indicate a position of the suture positioning member 117 or to indicate the direction in which the knob should be turned in order to rotate the suture positioning member 117 to a particular position.

While the suture passer guide 108 has been described as including the flexible elongate members 125 to couple the plunger assembly 121 to the suture positioning member 117, in some embodiments, a suture passer guide may alternatively include one or more rigid elongate members (e.g., geared rigid rods) that couple a plunger assembly to a suture positioning member. In such embodiments, for example, a set of proximal gears may couple the plunger assembly to a geared rigid rod, and a set of distal gears may couple the geared rigid rod to a suture positioning member. Such a configuration of the proximal and distal gears can allow rotation of the plunger assembly to cause rotation of the suture positioning member.

While the suture passer guide 108 has been described as including both the expandable member 116 and the suture positioning member 117, in some embodiments, the suture passer guide has a suture positioning member (e.g., the suture positioning member 117), but no expandable member. Such a suture passer guide can be used in the same general manner as the suture passer guide 108, with the exception that no proximal force is applied to the inner lining of the surgical cavity.

While the suture passer guide 108 has been described as including one set of non-intersecting guide passages, in some embodiments, a suture passer guide includes more than one set (for example, two, three, or four sets) of non-intersecting guide passages positioned along a length of an elongate tubular member of the suture passer guide. Suture passer guides having more than one set of non-intersecting guide passages may be adapted to suture surgical cavity walls having a thickness of less than 1.5 cm or more than 6.0 cm. In some examples, such suture passers may be adapted to suture surgical cavity walls having a thickness of up to 12.0 cm.

In some embodiments, suture passer guides having more than one set of non-intersecting guide passages include a colored band disposed on the external surface of the elongate tubular member and surrounding proximal holes of each set of non-intersecting guide passages to indicate a range of abdominal wall thicknesses that may be sutured by using the respective guide passages and to aid a surgeon in selecting an appropriate set of guide passages from among the multiple sets of guide passages. For example, in such embodiments, the surgeon could simply insert the suture passer 110 into the proximal opening that is associated with a colored band that lies along the outer surface of a patient's surgical wall. In some embodiments, such suture passer guides can alternatively or additionally have any of various other markings (e.g., letters, numbers, symbols, etc.) that can be used in a similar manner to that of the colored bands. Alternatively, such suture passer guides can include no markings at all. In such cases, the surgeon can simply rely on the positions of the guide passages to determine which of those guide passages to use for a particular procedure.

While the expandable member 116 has been described as including the proximal coupling member 151 and the distal coupling member 153, in some embodiments, an expandable member may not include proximal and distal coupling members. For example, an expandable member may alternatively include collapsible arms having proximal and distal arm segments that are integrally molded with an elongate tubular member of a suture passer guide.

While the expandable member 116 has been described as being biased to its expanded configuration, it should be appreciated that expandable members of the various suture passer guides described herein can alternatively be biased to their collapsed configuration. With such a configuration, for example, the user could push or release a button to move the expandable member from its collapsed configuration to its expanded configuration.

While the suture passer guide 108 has been described as including an elastic film 160 (see FIGS. 5 and 6) that is stretched over the expandable member 116 to reduce the risk of damage to the peritoneum 186 and/or to prevent loss of inflation pressure during use of the suture passer guide 108, in certain embodiments, the suture passer guide includes a heat shrink tube disposed to cover the expandable member 116 instead of the elastic film 160. In such embodiments, the heat shrink tube is similarly sealed to the proximal and distal coupling members 151, 153 of the expandable member 116 in a substantially fluid-tight manner. This arrangement can help to prevent gases within the surgical cavity from escaping through open spaces within the expandable member 116 and into the port site wound 183 during use of the suture passer guide 108. Examples of materials from which the heat shrink tube can be formed include polyethylene terephthalate (PET), polytetrafluoroethylene (PTFE), polyetheretherketone (PEEK), polypropylene, and polyethylene.

While the suture passers described above include a film or heat shrink tube that covers the expandable member, in certain embodiments, no such film or heat shrink tube is used. In such embodiments, the openings between the arms of the expandable member are uncovered.

Figure 10:
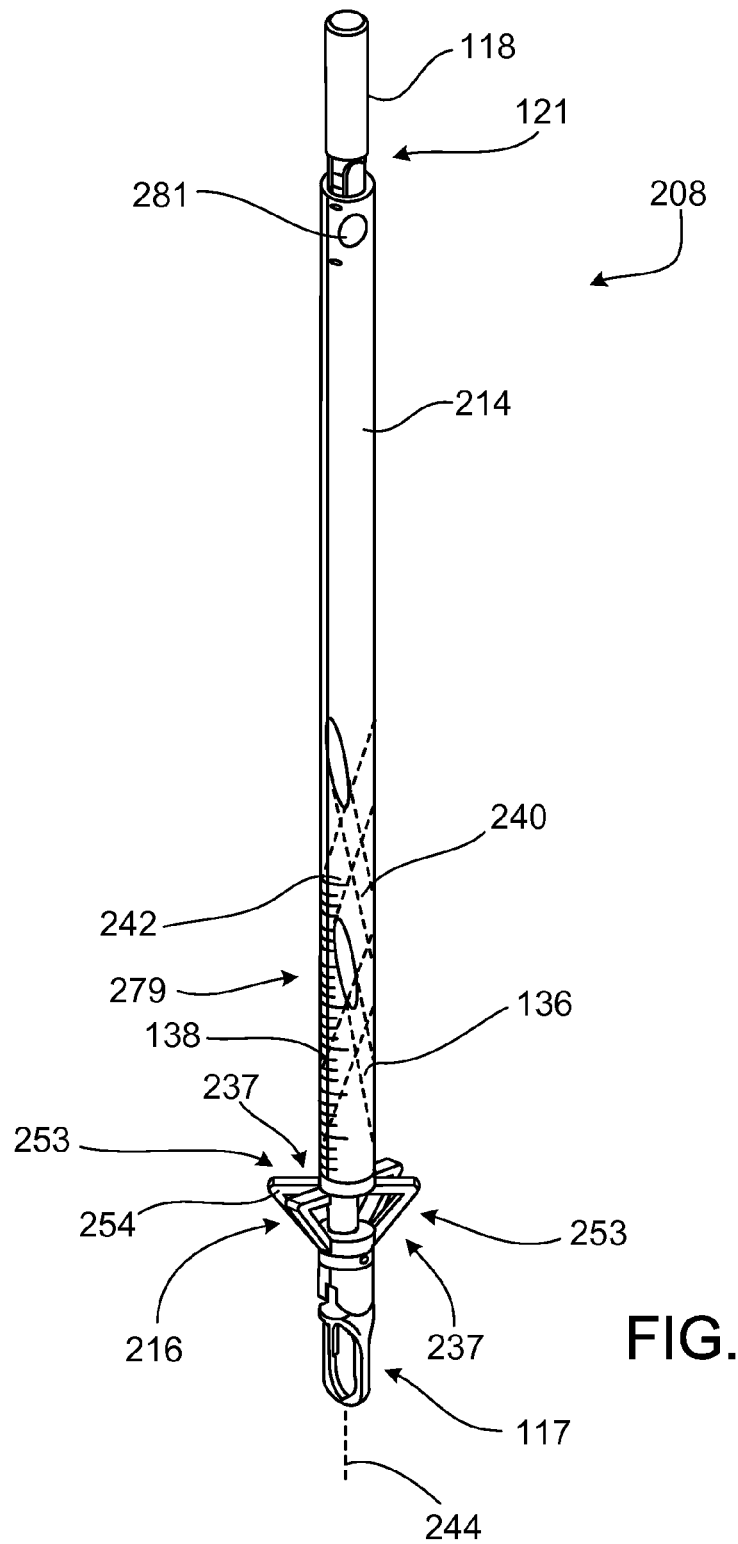
FIG. 10 is a perspective view of a suture passer guide that is generally similar to the suture passer guide of FIG. 1 but that includes two sets of guide passages and an expandable member having two groups of two collapsible arms.

While the suture passer guide 108 has been described as including the expandable member 116 having two collapsible arms 154 that are positioned opposite one another, in some embodiments, a suture passer guide includes an expandable member having multiple groups of collapsible arms that are circumferentially spaced from one another. In such embodiments, the groups of collapsible arms are typically circumferentially spaced from one another by a greater distance than the adjacent collapsible arms are spaced from one another within those groups. Such an arrangement can increase the tiltability of the suture passer guide within a surgical cavity. As shown in FIG. 10, one such suture passer guide 208 includes an expandable member 216 having four collapsible arms 254 (i.e., two groups 253 that each include two collapsible arms 254) that are coupled to proximal and distal coupling members 251, 253 of the expandable member 216. The collapsible arms 254 are similar in construction and function to the collapsible arms 154 of the expandable member 116 described above, with the exception that the collapsible arms 254 have a different width than the collapsible arms 154. The proximal and distal coupling members 251, 253 are similar in construction and function to the proximal and distal coupling members 151, 153 of the expandable member 116 described above, with the exception that the proximal and distal coupling members 251, 253 are integrated with a greater number of living hinges 159 than are the proximal and distal coupling members 151, 153 of the expandable member 116.

The groups 253 of the collapsible arms 254 are spaced approximately 180 degrees apart from each other (as measured from a vertical plane that is centered between the two collapsible arms 254 of each group 253). Circumferential gaps 237 between the groups 253 extend about 90° to about 150° around the circumference of the expandable member 216. The circumferential gaps 237 are larger than (e.g., about 60° to about 100° larger than) the gaps formed between the adjacent collapsible arms 254 within the groups 253. The gaps between the adjacent collapsible arms 254 within the groups 253, for example, typically extend about 30° to about 60° around the circumference of the expandable member 216. Each collapsible arm 254 typically has a width of about 0.2 cm to about 0.5 cm.

Due to the increased number of collapsible arms 254 provided around the expandable member 216 (as compared to the number of collapsible arms 154 situated around the expandable member 116 described above), the circumferential gaps 237 in the expandable member 216 are smaller than the circumferential gaps 137 in the expandable member 116. As a result, the user will encounter greater resistance to tilting the suture passer guide 208 as compared to tilting the suture passer guide 108. However, the two additional collapsible arms 254 of the expandable member 216 (as compared to the expandable member 116) provide additional surface area upon which the traction force between the expandable member 216 and the inner lining of the surgical cavity can be distributed during use of the suture passer guide 208. The increased distribution of the traction force improves the stability of the suture passer guide 208 while the suture passer guide 208 is held against the inner lining of the surgical cavity and, due to the more evenly distributed forces acting on the inner lining of the surgical cavity, further reduces the probability that any collapsible arm 254 will tear or otherwise damage the inner lining of the surgical cavity while the suture passer guide 208 is held against the inner lining of the surgical cavity.

The expandable member 216 can be retracted and expanded by pressing and releasing the button 118 located at the proximal end region of the elongate tubular member 214. In the manner described above with respect to the suture passer guide 108, the button 118 is coupled to the expandable member 216 via the internal shaft 168 and the spring 164 (shown in FIG. 4) in order to operate the expandable member 216 in this way. Additionally, in the manner described above with respect to the suture passer guide 108, the button 118 is further coupled to the suture positioning member 117 via the flexible elongate members 125 (shown in FIGS. 4 and 7) in order to rotate the suture positioning member 117 from one side of the suture passer guide 208 to the other side of the suture passer guide 208.

The elongate tubular member 214 is similar in construction and function to the elongate tubular member 114 of the suture passer guide 108 described above, with the exception that the elongate tubular member 214 includes a greater number of guide passages than the elongate tubular member 114. That is, the suture passer guide 208 includes the guide passages 136, 138 (i.e., distal guide passages), as well as third and fourth proximal guide passages 240, 242. The proximal guide passages 240, 242 are substantially similar in construction and function to the distal guide passages 136, 138, with the exception that the proximal guide passages 240, 242 may extend at an angle different than that of the distal guide passages 136, 138 and are disposed at a different position (i.e., proximal to the guide passages 136, 138) along the elongate tubular member 214 to allow for suturing of a surgical wall having a thickness different than that which can be sutured using the distal guide passages 136, 138. The distal guide passages 136, 138 and proximal guide passages 240, 242 extend at angles of about 14° and about 16°, respectively, relative to a longitudinal axis 244 of the elongate tubular member 214. The proximal guide passages 240, 242 may be used to suture a surgical wall having a thickness of about 6.0 cm to about 12.0 cm.

Using the suture passer guide 208 can be advantageous relative to using alternative suture passer guides having multiple sets of intersecting guide passages, where distal openings of a proximal set of guide passages may overlap proximal openings of a distal set of guide passages. During use of such suture passer guides, care must be taken to prevent the distal end of the suture passer from exiting the wrong set of guide passage openings (i.e., when the suture passer guide is passed through a proximal guide passage, care must be taken to prevent the suture passer 110 from exiting the suture passer guide through a proximal opening of a distal guide passage as opposed to a distal opening of the proximal guide passage) and therefore passing through the peritoneum at an undesired puncture point. The circumferential offset of the non-intersecting guide passages of the suture passer guide 208 prevents such a complication since distal openings of the proximal guide passages 240, 242 will not overlap the proximal openings 120, 122 of the distal guide passages 136, 138. Furthermore, the non-overlapping feature of the guide passage openings results in maximal guide passage surface areas that can optimally guide a suture passer through the suture passer guide 208.

The suture passer guide 208 further includes the self-sealing elastic plugs 161 in the distal openings 124, 126 of the guide passages 136, 138, as well as other self-sealing elastic plugs sized to fit within distal openings of the guide passages 240, 242.

The suture passer guide 208 additionally includes a set of ruler markings 279 on the external surface of the elongate tubular member 214 that increase in value from the distal end of the elongate tubular member 214 toward the proximal end of the elongate tubular member 214 to allow the surgeon to gauge the thickness of tissue in which the suture passer guide 208 is inserted. Additionally, the suture passer guide 208 includes depressions 281 near the proximal end of the elongate tubular member 214. Alternatively or additionally, the proximal end region of the elongate tubular member 214 can include rings formed on the external surface of the elongate tubular member near the proximal end of the elongate tubular member or any other types of textured surfaces that improve the ability of the surgeon to grip the suture passer guide 208.

The various components of the suture passer guide 208, including the elongate tubular member 214, the expandable member 216, the internal shaft 168, and the suture positioning member 117 can be formed of one or more of the medical grade materials discussed above with respect to the corresponding components of the suture passer guide 108.

While the suture passer guides 108, 208 have been described as including expandable members having two collapsible arms and two groups of collapsible arms, respectively, that are spaced by two circumferential gaps, in certain embodiments, a suture passer guide may include more than two groups of collapsible arms. In other embodiments, a suture passer guide may include an expandable member having multiple collapsible arms that are not positioned in groups but that are instead spaced equal distances around a circumference of the expandable member. For such embodiments, the expandable member can be retracted and expanded by pressing and releasing the button 118 located at a proximal end region of an elongate tubular member of the suture passer guide in the manner described above with respect to the suture passer guide 108.

While the suture passer guide 208 has been described as having an actuator that includes the plunger assembly 121, it should be appreciated that any of the various other types of actuators described herein can alternatively be used to actuate the suture positioning member 117 and the expandable member 216.

Figure 11:
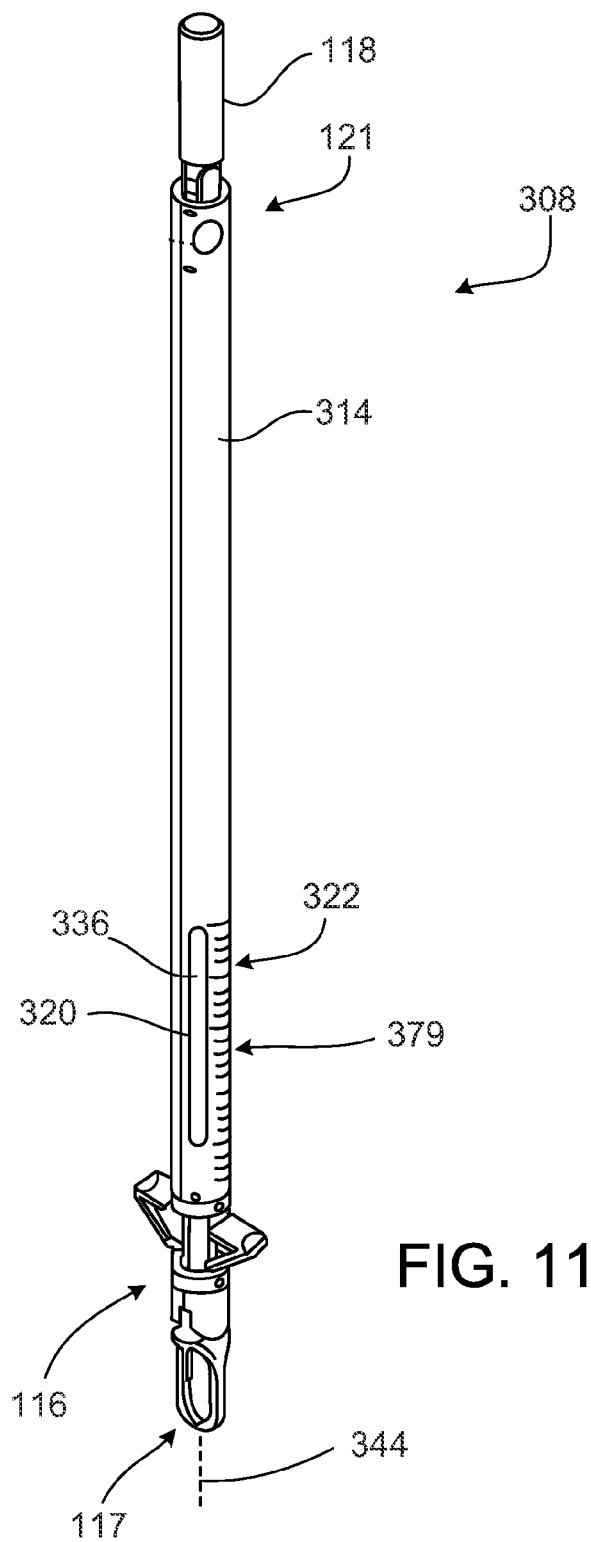
FIG. 11 is a perspective view of a suture passer guide that is generally similar to the suture passer guide of FIG. 1 but that includes a single passage through which a suture passer can be inserted during use.

While the suture passer guides 108, 208 above have been described as including non-intersecting guide passages 136, 138, 240, 242 that extend through a solid core of the elongate tubular member 114, 214, in certain embodiments, the suture passer guide includes a single elongate passage extending from one side of an elongate tubular member to the other side of the elongate tubular member. For example, FIG. 11 illustrates a suture passer guide 308 that includes a single passage 336 extending from a first opening 320 in a sidewall of an elongate tubular member 314 to a second opening 322 in the sidewall of the elongate tubular member 314 that is opposite the first opening 320. The second opening 322 is centrally aligned with the first opening 320 and has the same size and shape as the first opening 320. Thus, the passage 336 has a uniform vertical height across the elongate tubular member 314. The elongate tubular member 314 is similar in construction and function to the elongate tubular members 114, 214 of the suture passer guides 108, 208, with the exception that the openings 320, 322 of the elongate tubular member 314 have different sizes and shapes than the openings of the guide passages 136, 138, 240, 242. Due to the uniform vertical height of the passage 336 across the elongate tubular member 114, the passage 336 allows a surgeon to insert a suture passer (e.g., the suture passer 110) through the passage 336 at any position along a length of the openings 320, 322 and at any appropriate angle so that the surgeon can obtain a suture bite having any desired, appropriate length or any length distribution about the longitudinal axis 344 of the elongate tubular member 314. The openings 320, 322 typically have a width of about 0.07 inch to about 0.2 inch (e.g., about 0.120 inch) and a length of about 4 cm to about 9 cm (e.g., about 5 cm).

The suture passer guide 308 further includes the plunger assembly 121, the expandable member 116, the distal base 156, and the suture positioning member 117 described above in connection with the suture passer guide 108. The expandable member 116 can be retracted and expanded by pressing and releasing the button 118 located at a proximal end region of the elongate tubular member 314. In the manner described above with respect to the suture passer guides 108, 208, the button 118 is coupled to the expandable member 116 via an internal shaft 368 and the spring 164 (both shown in FIG. 12) in order to operate the expandable member 116 in this way. Additionally, in the manner described above with respect to the suture passer guides 108, 208, the button 118 is further coupled to the suture positioning member 117 via the flexible elongate members 125 (shown in FIG. 12) in order to rotate the suture positioning member 117 from one side of the suture passer guide 308 to the other side of the suture passer guide 308.

Figure 12:
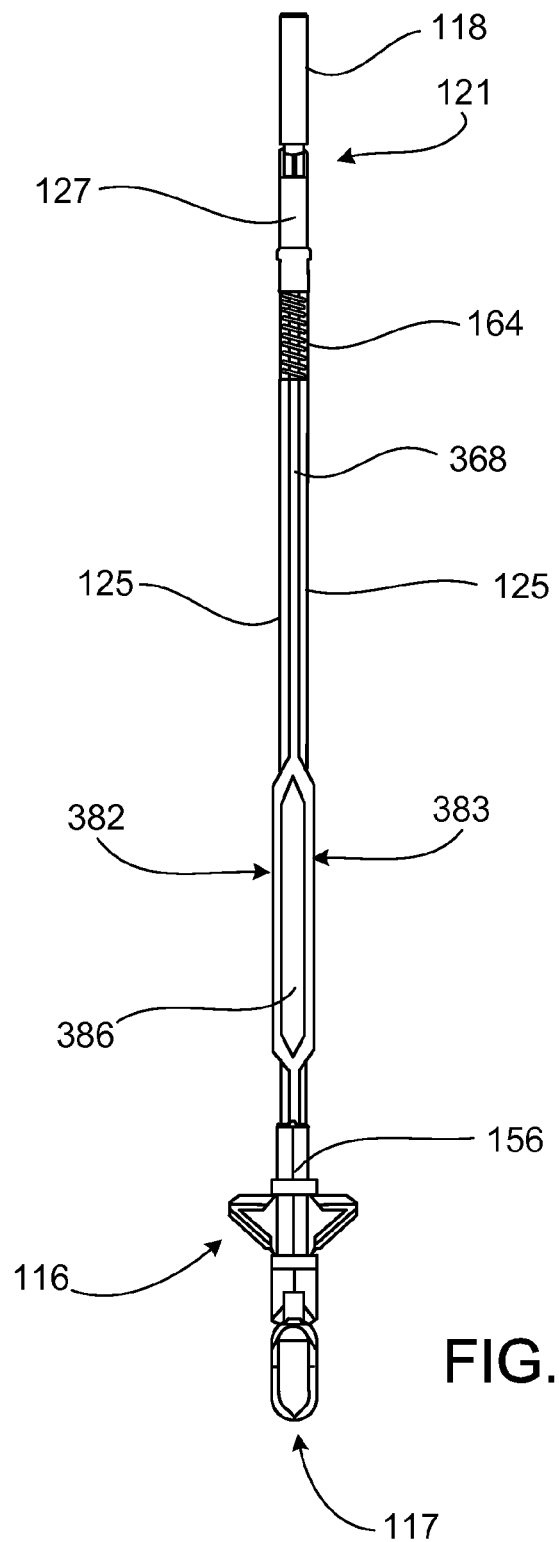
FIG. 12 is a side view of the suture passer guide of FIG. 11, with the elongate tubular member of the suture passer guide removed to show the internal shaft and other internal components of the suture passer guide.

As shown in FIG. 12, the internal shaft 368 includes a channel 386 that forms a portion of the passage 336 and is centrally aligned with the first and second openings 320, 322 of the passage 336. The channel 386 is further oriented substantially co-planar with the suture positioning member 117 so that the channel 386 can guide the suture passer through the aperture 115 of the suture positioning member 117 when the suture positioning member 117 is rotated to the left or right side of the suture passer guide 308. Recesses 382, 383 located around the left and right edges of the channel 386 guide the flexible elongate members 125 along the edges of the channel 386 so that the suture passer does not contact the flexible elongate members 125 as the suture passer is passed through the passage 336. The channel 386 typically has a width of about 0.07 inch to about 0.2 inch (e.g., about 0.120 inch) and a length of about 4 cm to about 9 cm (e.g., about 5 cm).

Referring briefly again to FIG. 11, the suture passer guide 308 further includes depressions 281 near the proximal end of the elongate tubular member 314. The proximal end region of the elongate tubular member 314 can alternatively or additionally include rings formed on the external surface of the elongate tubular member near the proximal end of the elongate tubular member or any other types of textured surfaces that improve the ability of the surgeon to grip the suture passer guide 308.

The suture passer guide 308 additionally includes a set of ruler markings 379 on the external surface of the elongate tubular member 314 that increase in value from the distal end of the elongate tubular member 314. The suture passer guide 308 may typically be used to suture surgical walls having thicknesses of about 3 cm to about 12 cm.

In some embodiments, the suture passer guide 308 includes self-sealing elastic plugs that are substantially similar in material and function to the self-sealing elastic plugs 161 of the suture passer guide 108 and that are sized to be disposed within the first and second openings 320, 322 of the passage 336.

The various components of the suture passer guide 308, including the elongate tubular member 314, the expandable member 116, the internal shaft 368, and the suture positioning member 117 can be formed of one or more of the medical grade materials described above with respect to the corresponding components of the suture passer guides 108, 208.

While the suture passer guide 308 has been described as including the expandable member 116, it should be appreciated that a suture passer guide including the single passage 336 may alternatively include any of the various other types of expandable members described herein.

While the suture passer guide 308 has been described as having an actuator that includes the plunger assembly 121, it should be appreciated that any of the various other types of actuators described herein can alternatively be used.

Figure 13:
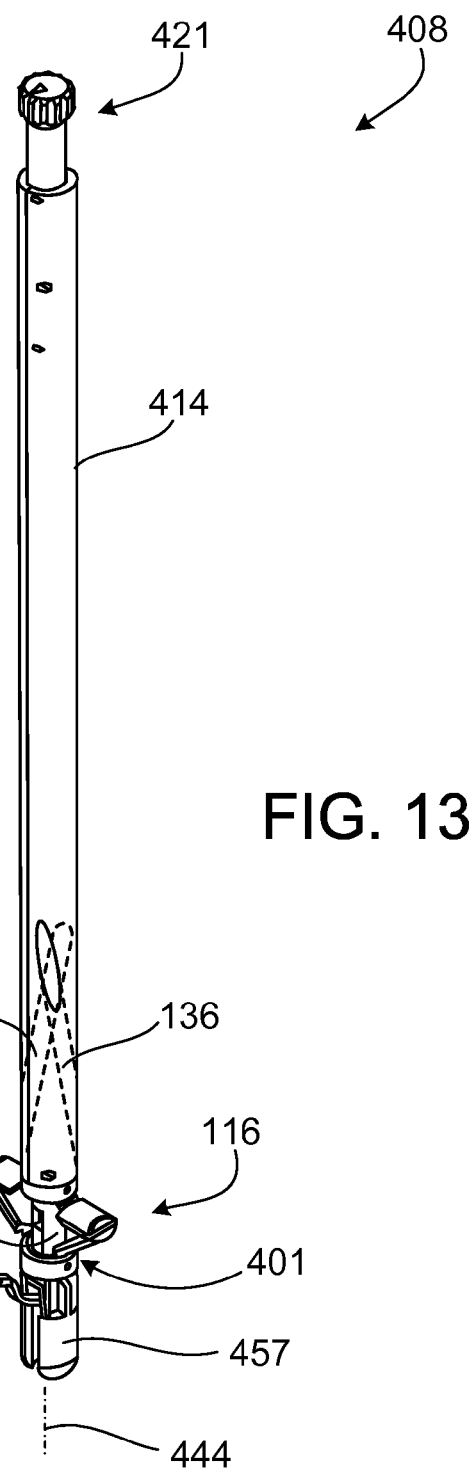
FIG. 13 is a perspective view of a suture passer guide that includes a suture positioning member that is that is rotatable about an axis that is coincident with a longitudinal axis of an elongate tubular member of the suture passer guide to allow a suture to be repositioned from one side area of the elongate tubular member of the suture passer guide to another side area of the elongate tubular member of the suture passer guide.

While each of the suture passer guides 108, 208, 308 discussed above has been described as including the suture positioning member 117, which defines the aperture 115 through which a suture passer and a grasped suture can be inserted, other types of suture positioning members can be used. For example, FIG. 13 illustrates a suture passer guide 408 that includes a suture positioning member 417 operable to rotate about a longitudinal axis 444 of an elongate tubular member 414 such that the suture positioning member 417 can move or sweep a suture from one side of the elongate tubular member 414 to an opposite side of the elongate tubular member 414. The elongate tubular member 414 includes the guide passages 136, 138 and is substantially similar in function to the elongate tubular member 114. The elongate tubular member 414 is secured to a plunger assembly 421 that is located at a proximal end region of the elongate tubular member 414 and a distal support member 456 located at a distal end region of the elongate tubular member 414, as will be described in more detail below. The suture passer guide 408 further includes the expandable member 116 described above.

Figure 14:
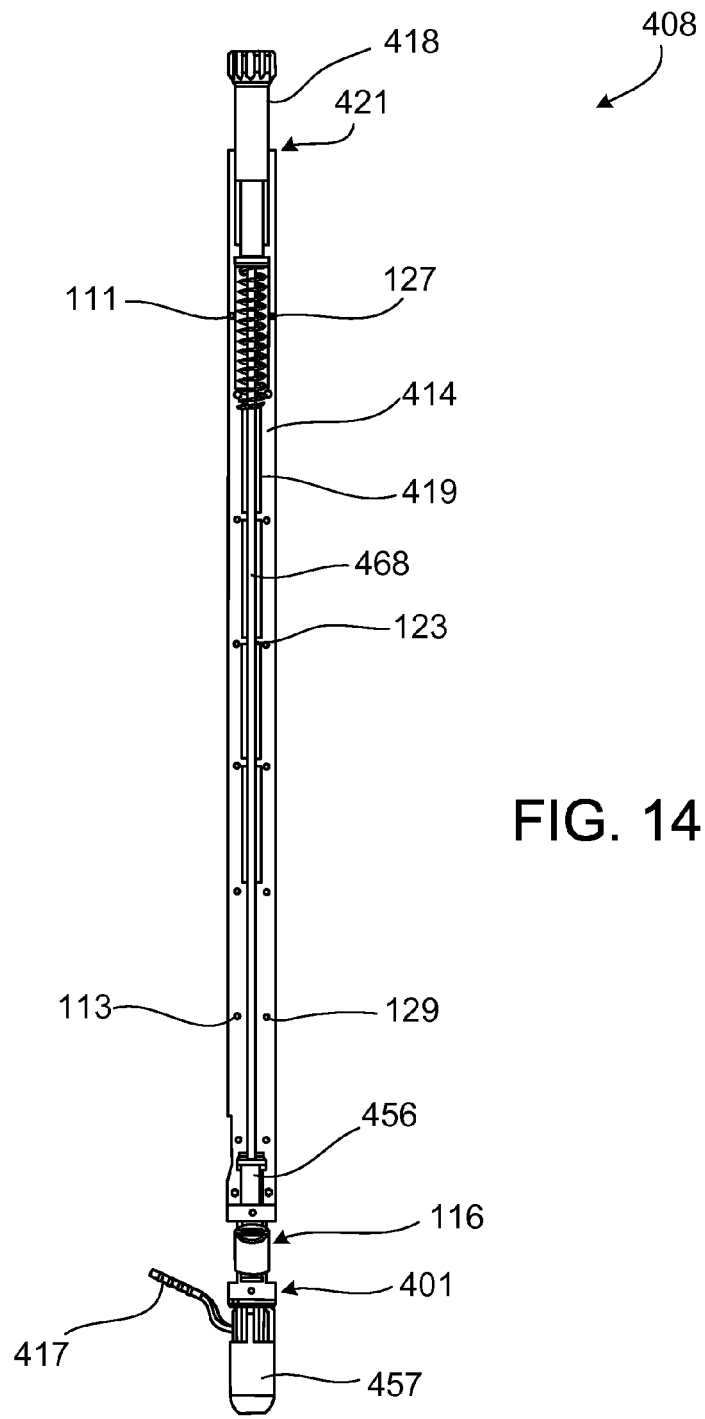
FIG. 14 is a front view of the suture passer guide of FIG. 13, with one half of the elongate tubular member of the suture passer guide removed to show certain internal components of the suture passer guide.

FIG. 14 illustrates a front view of the suture passer guide 408 with one half of the elongate tubular member 414 removed to show certain internal components of the suture passer guide 408. The elongate tubular member 414 includes a central lumen 419. At the proximal end of the elongate tubular member 414, the central lumen 419 is sized to surround a portion of the plunger assembly 421 secured to a proximal end of an internal shaft 468. At the distal end of the elongate tubular member 414, the central lumen 419 is sized to surround a portion of the distal support member 456, which extends through the expandable member 116 and is coupled with the suture positioning member 417, a bearing 401, and a distal base 457. The internal shaft 468 extends from the plunger assembly 421, through the distal support member 456, and to the distal base 457 of the suture passer guide 408 to actuate the suture positioning member 417 and the expandable member 116, as will be discussed in more detail below. The elongate tubular member 414 also includes the support members 123, the pegs 111, 113, and the recesses 127, 129 described above to help ensure that the two halves of the elongate tubular member 414 are properly aligned.

Figure 15:
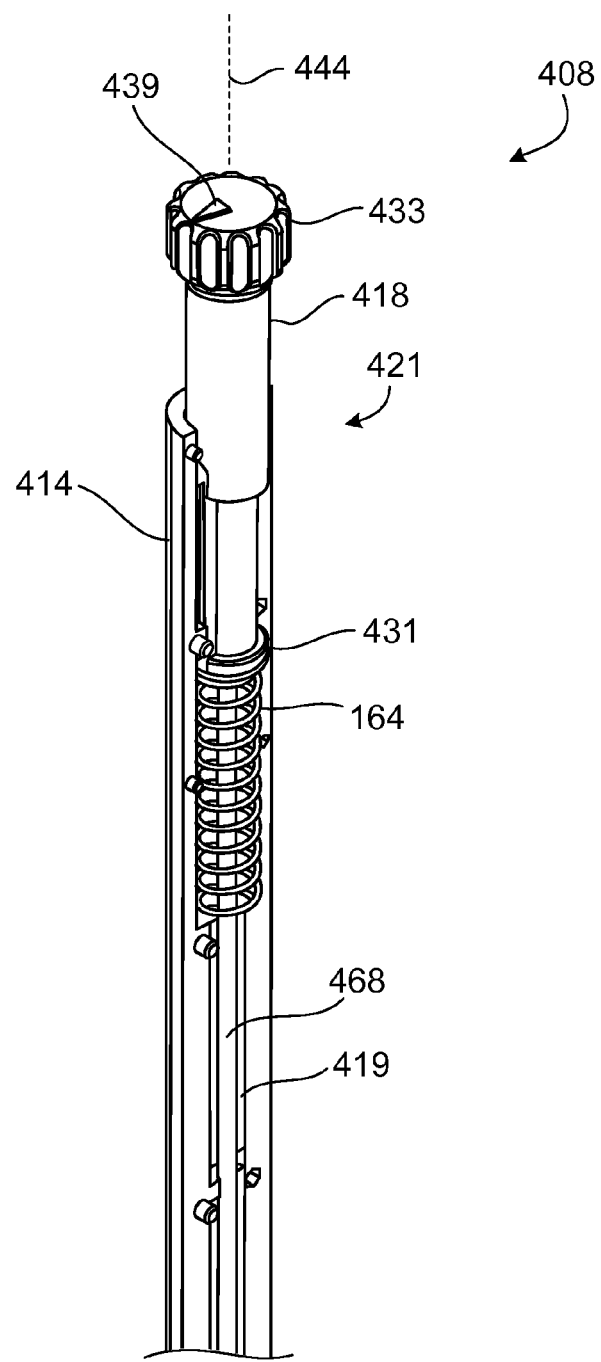
FIG. 15 is an enlarged perspective view of a proximal end region of the suture passer guide of FIG. 13, with one half of the elongate tubular member removed to show a plunger assembly in a proximal position.

FIG. 15 is an enlarged view of the proximal end region of the suture passer guide 408 with one half of the elongate tubular member 414 removed to expose certain internal components of the plunger assembly 421. The plunger assembly 421 includes a button 418 that is rotatable within the central lumen 419 about the longitudinal axis 444 of the elongate tubular member 414 and that is coupled to a proximal end of the internal shaft 468. The plunger assembly 421 further includes a support ring 431 that is fixedly coupled to a distal end of the button 418 and to a proximal end region of the internal shaft 468. The spring 164 is coupled to a distal end of the support ring 431. The internal shaft 468 is rotationally fixed relative to the suture positioning member 417, such that rotating the button 418 causes rotation of the distal base 457 and the suture positioning member 417 about the longitudinal axis 444 of the elongate tubular member 414, as will be discussed in more detail below. A series of knurls 433 and a positional indicator (i.e., an arrow) 439 are formed on a graspable proximal projection or knob of the button 418. The positional indicator 439 indicates a circumferential position of the suture positioning member 417, and the knurls 433 provide a gripping surface so that the button 418 can be easily gripped and rotated by a user of the suture passer guide 408. The button 418 is typically rotatable through about 360° about the longitudinal axis 444 of elongate tubular member 414.

Referring to FIGS. 13-15, axial movement of the button 418 causes axial movement of the internal shaft 468 such that the button 418 can be operated to radially expand and collapse the expandable member 116 and to radially extend and retract the suture positioning member 417. The spring 164 applies an outward (extension) force to the support ring 431 and thus biases the support ring 431 (and accordingly the internal shaft 468) to a proximal position, causing the expandable member 116 and the suture positioning member 417 to be biased to their radially expanded configurations, as shown in FIGS. 13 and 14. When the button 418 is depressed, the internal shaft 468 moves distally within the central lumen 419 of the elongate tubular member 414, causing distal movement of the distal base 457 and the bearing 401. This action causes the expandable member 116 (i.e., the collapsible arms 154 of the expandable member 116) to radially collapse. The suture passer guide 408 has a short stroke length (i.e., a distance that the button 418 is depressed to collapse the expandable member 116 and retract the suture positioning member 417), thereby improving its ease of use. The suture passer guide 408 can, for example, have a stroke length of about 0.375 inch to about 0.625 inch (e.g., about 0.625 inch).

Figure 16:
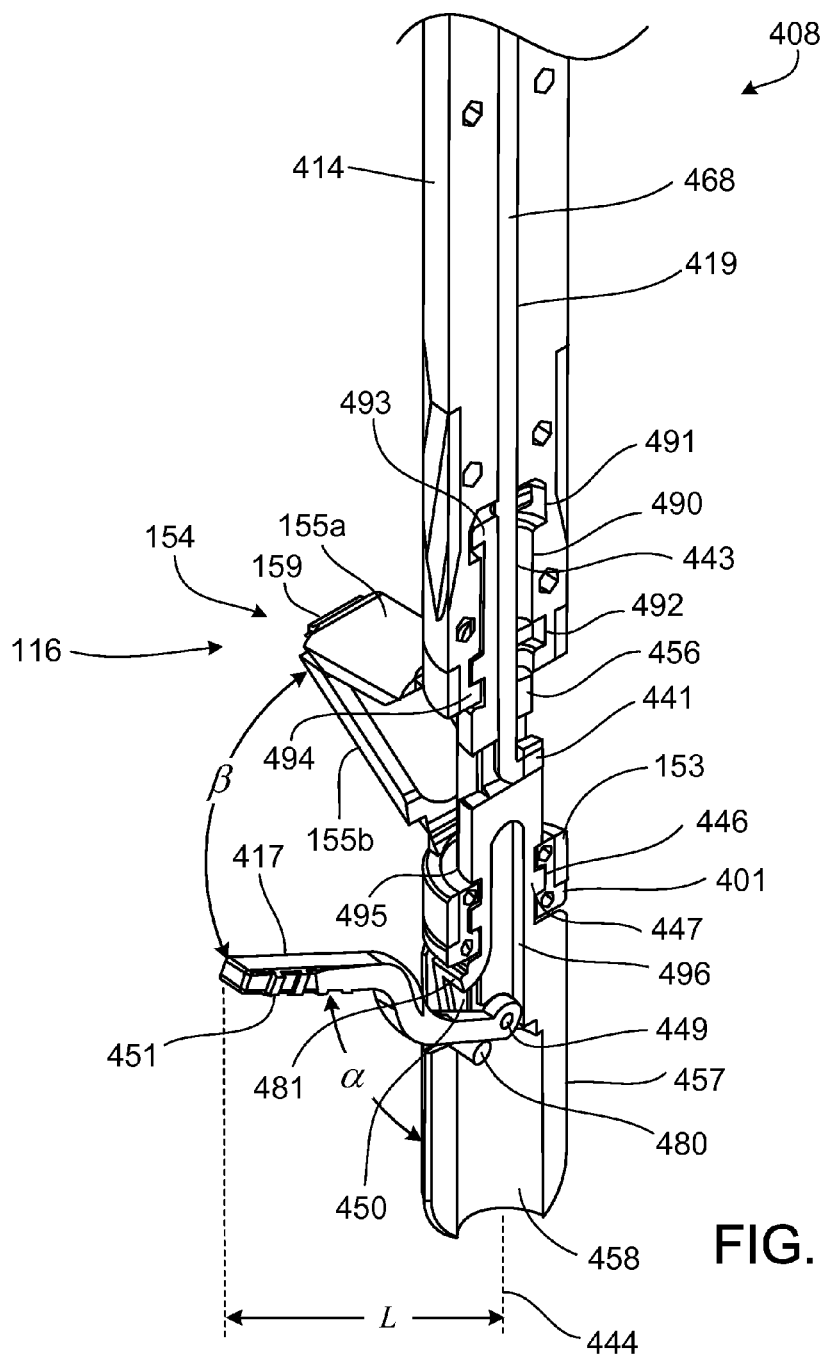
FIG. 16 is an enlarged perspective, cross-sectional view of the distal end region of the suture passer guide of FIG. 13, showing the suture positioning member in a radially extended position and the expandable member in a radially expanded configuration.
Figure 17:
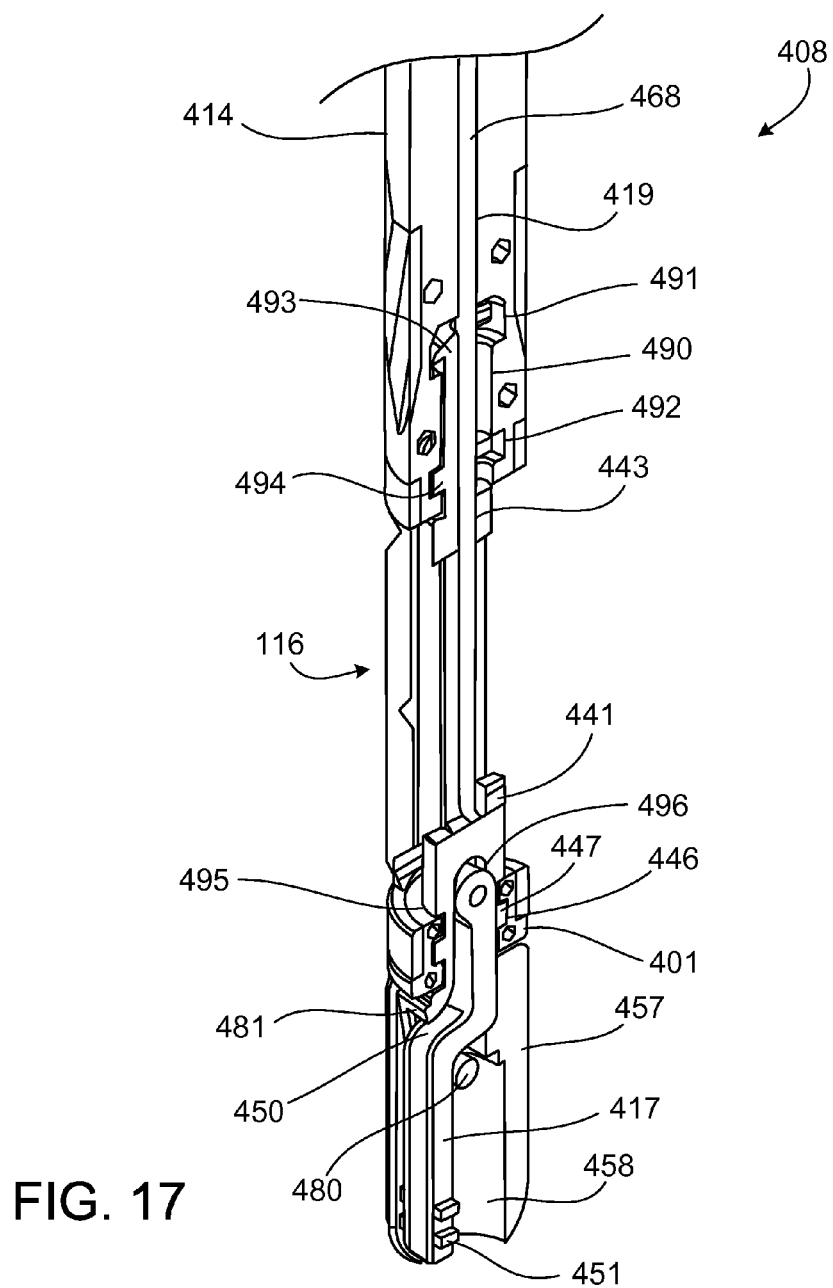
FIG. 17 is an enlarged perspective, cross-sectional view of the distal end region of the suture passer guide of FIG. 13, showing the suture positioning member in a radially retracted position and the expandable member in a radially collapsed configuration.

FIGS. 16 and 17 illustrate enlarged perspective, cross-sectional views of the distal end region of the suture passer guide 408 with the expandable member in its expanded and collapsed positions, respectively, and with the suture positioning member 417 in its extended and retracted positions, respectively. The distal support member 456 extends from the distal end region of the elongate tubular member 414. The distal support member 456 includes proximal and distal projection members 493, 494 that are generally annular in shape. The distal end region of the elongate tubular member 414 defines a notch 490 that extends from the central lumen 419 to the distal end of the elongate tubular member 414 and that includes proximal and distal annular portions 491, 492. The annular portions 491, 492 of the notch 490 retain the proximal and distal projection members 493, 494 of the distal support base 456 such that the distal support member 456 is axially fixed relative to the elongate tubular member 414. The internal shaft 468 extends through and is rotatable within the central lumen 419 of the elongate tubular member 414 and within a central channel 443 of the distal support member 456. The distal end region of the internal shaft 468 is rigidly fixed to a projection 441 extending from a proximal end of the distal base 457. The distal support member 456 extends into a proximal channel 495 of the distal base 457. As a result of this configuration, the distal base 457 is slidable along the distal support member 456, and, rotation of the internal shaft 468 causes rotation of the distal base 457, the suture positioning member 417, and the distal support member 456 about the longitudinal axis 444 of the elongate tubular member 414 while the distal support base 456 remains axially fixed relative to the elongate tubular member 414.

Typically, the distal base 457, suture positioning member 417, and distal support member 456 are rotatable 360° relative to the elongate tubular member 414. In some embodiments, however, rotation of these components relative to the elongate tubular member 414 can be limited. In such embodiments, for example, the distal base 457, suture positioning member 417, and distal support member 456 can be rotatable through an angle of about 160° to about 200° about the longitudinal axis 444 of the elongate tubular member 414, according to the rotation of the button 418. For example, a recessed channel may disposed along a limited portion of an inner surface of the elongate tubular member 414 (i.e., along the central lumen 419 of the elongate tubular member 414) and a complimentary stopping member may extend from a surface of the internal shaft 468 and into the recessed channel, such that the internal shaft 468 is permitted to rotate along a circumference of the recessed channel, but not around an entire circumference of the elongate tubular member 414.

Still referring to FIGS. 16 and 17, the internal shaft 468 is axially slidable within the central channel 443 of the distal support member 456, and axial movement of the internal shaft 468 causes axial movement of the distal base 457. The bearing 401 is rigidly fixed to the distal coupling member 153 of the expandable member 116, such that the bearing 401 is substantially prevented from rotating relative to the expandable member 116 and the elongate tubular member 114. The bearing 401 forms a support surface 446 that engages an annular flange 447 extending from the distal base 457 in a manner such that axial movement of the distal base 457 causes axial movement of the bearing 401 and collapse (see FIG. 17) or expansion (see FIG. 16) of the expandable member 116. The annular flange 447 of the distal base 457 is allowed to slide against the support surface 446 of the bearing 401 as the distal base 457 is rotated such that the distal base 457, when rotated by the internal shaft 468, is allowed to rotate relative to the bearing 401, the expandable member 116, and the elongate tubular member 414.

A pin 449 pivotably couples an internal end of the suture positioning member 417 to a distal end of the support member 456 and is aligned with the longitudinal axis 444 of the elongate tubular member 414. As noted above, the distal support member 456 is axially fixed relative to the elongate tubular member 414. Thus, proximal axial movement of the distal base 457 relative to the suture positioning member 417 causes the suture positioning member 417 to pivot about the pin 449 into a radially extended position, as shown in FIG. 16, while distal axial movement of the distal base 457 causes the suture positioning member 417 to pivot about the pin 449 into a radially retracted position, as shown in FIG. 17. The distal base 457 includes an aperture 450 through which the suture positioning member 417 extends when in the radially extended position. The aperture 450 is defined in part by a proximal edge 481 and a distal support stop 480 that abut the suture positioning member 417 as the distal base 457 is moved distally and proximally, respectively. As the distal base 457 is moved distally from a proximal position, the proximal edge 481 abuts a top surface of the suture positioning arm 417, causing the suture positioning arm 417 to pivot counterclockwise (as viewed from the cross-sections shown in FIGS. 16 and 17) such that the suture position arm 417 is pushed radially inward and is positioned partially within an elongate slot 496 of the distal base 457. As the distal base 457 is moved proximally from a distal position, the distal support stop 480 abuts a bottom surface of the suture positioning arm 417, causing the suture positioning arm 417 to pivot clockwise (as viewed from the cross-sections shown in FIGS. 16 and 17) such that the suture positioning arm 417 is pushed radially outward from the elongate slot 496 of the distal base 457

Still referring to FIGS. 16 and 17, ridges 451 extend from a surface of an external end region of the suture positioning member 417. The ridges are configured to engage a suture such that, as the suture positioning member 417 is rotated, the suture positioning member 417 can move the suture from one side of the elongate tubular member 414 to the other side of the elongate tubular member 414.

In some embodiments, the suture positioning member 417 has a thickness of about 0.05 inch to about 0.10 inch. In some embodiments, the suture positioning member 417 has a width of about 0.0625 inch to about 0.125 inch (e.g., about 0.09 inch). The ridges 451 extend a sufficient distance from the surface of the suture positioning member 417 to capture the suture.

Referring particularly to FIG. 16, when the internal shaft 468 is moved proximally (e.g., due to the expansion of the spring 164 shown in FIG. 15), the distal base 457 moves proximally, the expandable member 116 radially expands, and the suture positioning member 417 pivots about the pin 449 to its radially extended position. In its fully extended configuration, the suture positioning member 417 extends radially through the opening 450 to a distance L (measured perpendicular to the longitudinal axis 144) of about 0.75 inch to about 1.25 inches (e.g., about 0.85 inch) from an outer surface of the distal base 457, and the external end of the suture positioning member 417 forms an angle α of about 90° to about 135° (e.g., about 90°) with the outer surface of the distal base 457 (or with the longitudinal axis 144).

As the internal shaft 468 is moved proximally, expansion of the expandable member 116 and extension of the suture positioning member 417 occur at substantially the same time and due to one axial stroke of the button 418. Such simultaneous actuation of the expandable member 116 and the suture positioning member 417 reduces the time needed to repair a wound using the suture passer guide 408 as compared to suture passer guides that require sequential actuation of an expandable member and a suture positioning member.

Still referring to FIG. 16, the suture positioning member 417 has a curved profile such that, when the expandable member 116 is in the expanded configuration and the suture positioning member 417 is extended, the suture positioning member 417 is positioned in close proximity to an inner lining (e.g., the peritoneum 186) of a surgical cavity (e.g., the abdominal cavity 180) but without interfering with the collapsible arms 154 of the expandable member 116. For example, the free end of the suture positioning member 417 can be positioned about 0.25 inch to about 0.5 inch from the upper surfaces of the proximal segment 155A of the collapsible arms 154 of the expandable member 116, which contact the inner lining of the surgical cavity during a procedure. In this manner, the suture positioning member 116 is configured to position the suture in close proximity to the distal openings 124, 126 of the guide passages 136, 138 without interfering with the expandable member 116. In some embodiments, the suture positioning member 417 forms an angle β of about 0° to about 45° with the distal segments 155b of the collapsible arms 154 of the expandable member 116 and is spaced about 0.25 inch to about 0.5 inch from the collapsible arms 154 (as measured from the external end of the suture positioning member 417 to the upper surfaces of the proximal segments 155a of the collapsible arms 154).

Referring now to FIG. 17, when the internal shaft 468 is moved distally (e.g., by depressing the button 418 shown in FIGS. 13-15), the expandable member 116 collapses, the distal base 457 moves distally, and the suture positioning member 417 pivots about the pin 449 such that a distal end region of the suture positioning member 417 collapses or retracts substantially flush with the outer surface of the distal base 457 and within a recess 458 extending radially inward from the outer surface of the distal base 457. In such a configuration, the suture passer guide 408 can be passed through the central lumen 106 of the endoscopic port 102.

The suture passer guide 408 also includes self-sealing elastic plugs 161 disposed within the distal openings 124, 126 of the suture passer guide 408 (shown in FIGS. 18D-18I).

In certain embodiments, an outer surface of the proximal end region of the elongate tubular member 414 includes gripping features, such as depressions, rings, or any other types of textured surfaces that improve the ability of the surgeon to grip the elongate tubular member 414 of the suture passer guide 408.

As with the suture passer guides 108, 208, 308 described above, the suture passer guide 408 can additionally include a set of ruler markings on the external surface of the distal end region of the elongate tubular member 414 to provide the surgeon with an indication of the thickness of the tissue through which the suture passer guide 408 has been inserted. The suture passer guide 408 can typically be used to suture surgical walls having thicknesses of about 3 cm to about 12 cm.

The various components of the suture passer guide 408 can be formed of any of the various medical grade materials discussed above with respect to corresponding components of the suture passer guides 108, 208, 308.

FIGS. 18A-18I schematically illustrate a method of using an endoscopic surgical kit (e.g., an endoscopic surgical kit that includes the endoscopic port 102, the suture passer guide 408, the obturator 104, and the suture passer 110) to perform a laparoscopic surgical procedure in the abdominal cavity 180 of a patient and to subsequently repair the endoscopic port wound 183 used to access the patient's abdominal cavity 180. To perform the surgical procedure, the endoscopic port 102 is first inserted into the patient's abdominal cavity 180. One or more surgical tools are then inserted through the central lumen 106 of the endoscopic port 102 and into the abdominal cavity 180 to carry out the procedure.

Figure 18A:
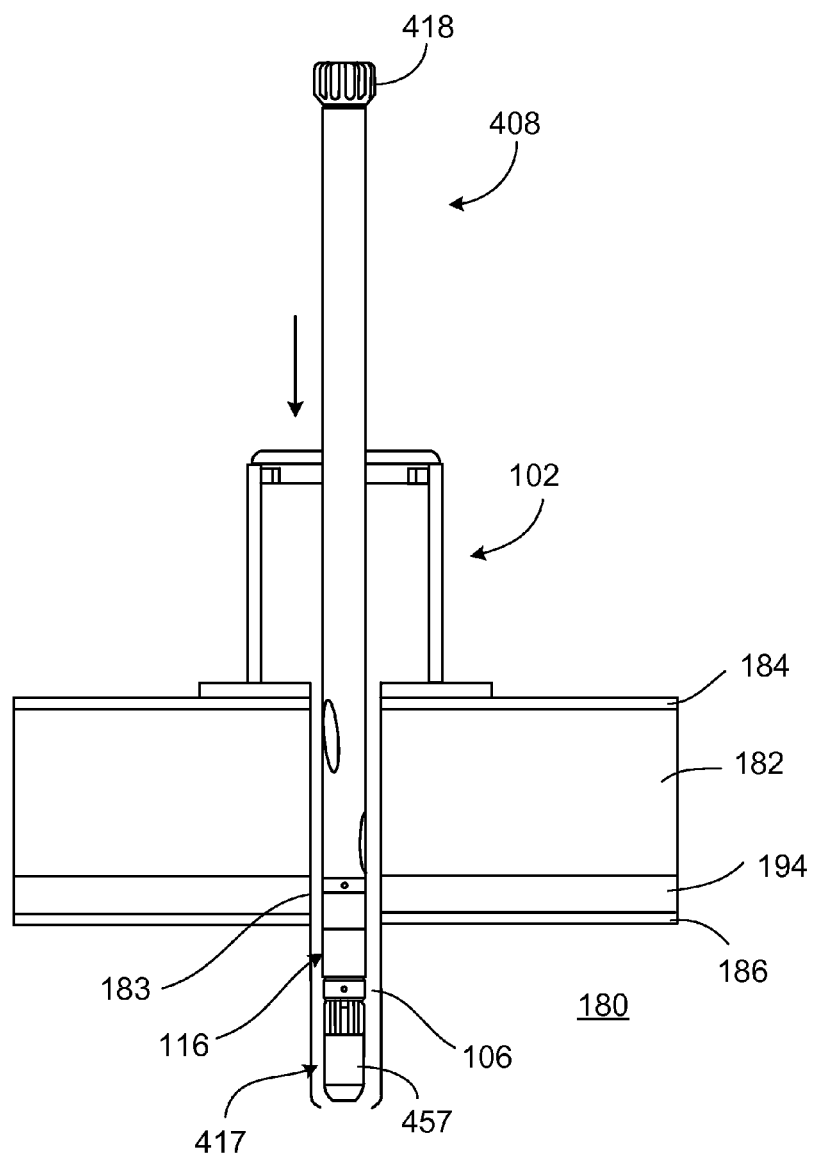
FIGS. 18A-18I schematically illustrate a method of performing a laparoscopic surgery and using the suture passer guide of FIG. 13 to repair an endoscopic port site wound.

After completing the surgical procedure within the abdominal cavity 180, the suture passer guide 408 is inserted through the central lumen 106 of the endoscopic port 102 and into the abdominal cavity 180 in order to facilitate repair of the port site wound 183, as shown in FIG. 18A. To insert the suture passer guide 408 through the central lumen 106 of the endoscopic port 102, the button 418 is first depressed to collapse the expandable member 116 and the suture positioning member 417. The suture passer guide 408 is then inserted into the central lumen 106 of the endoscopic port 102. Once the collapsed expandable member 116 and suture positioning member 417 are positioned within the central lumen 106 of the endoscopic port 102, the button 418 can be released as the user continues to pass the suture passer guide 408 distally through the lumen 106 toward the abdominal cavity 180 of the patient. The sidewalls of the obturator 102 retain the expandable member 116 and the suture positioning member 417 in the collapsed configuration as the suture passer guide 408 is passed through the lumen 106.

Figure 18B:
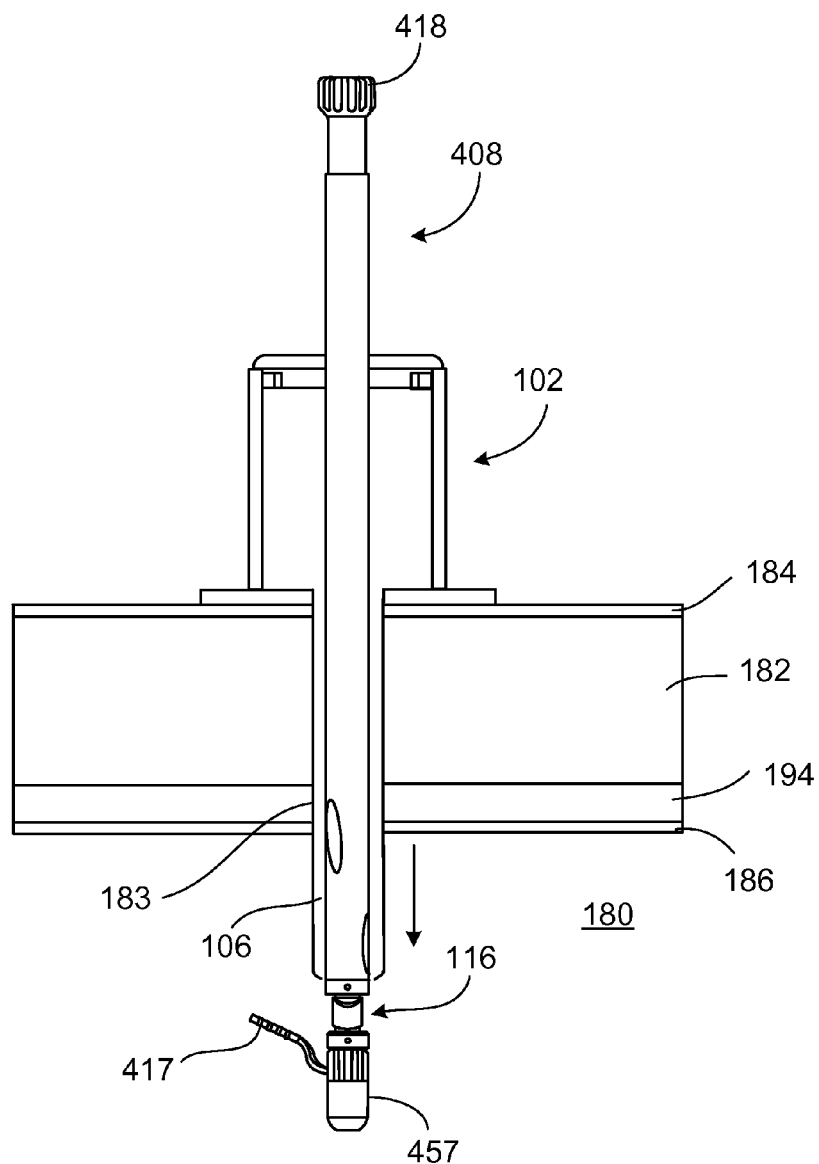

Referring to FIG. 18B, when the expandable member 116 and the suture positioning member 417 are passed distally beyond the distal end of the endoscopic port 102, the expandable member 116 automatically expands, and the suture positioning member 417 automatically extends radially from the distal base 457 of the suture passer guide 408. It will be understood that the collapsible arms 154 of the expandable member 116 extend radially into and out of the plane of the paper in the view shown in FIG. 18B.

Figure 18C:
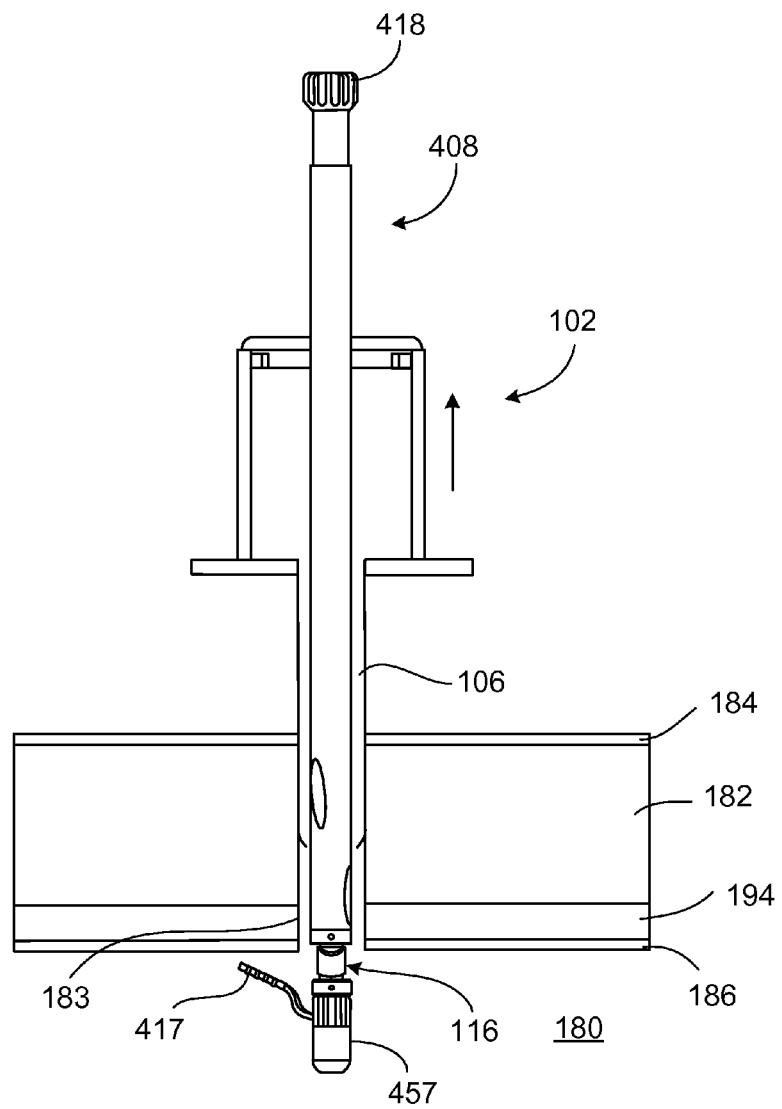

Referring to FIG. 18C, with the expandable member 116 in its expanded configuration and the suture positioning member 417 extended, the endoscopic port 102 is then removed from the wound 183 by pulling proximally on the proximal end region of the endoscopic port 102. As the endoscopic port 102 is removed from the port site wound 183, the expanded expandable member 116 contacts the inner lining of the patient's abdominal cavity (i.e., the patient's peritoneum 186), thereby preventing the suture passer guide 408 from being pulled out of the port site wound 183 along with the endoscopic port 102. Because the collapsible arms 154 of the expandable member 116 extend radially into and out of the plane of the paper in the view shown in FIG. 18C and the tissue of the patient is shown in cross-section, the contact between the expandable member 116 and the peritoneum 186 cannot be seen in FIG. 18C. However, it will be readily understood that the upper surfaces of the proximal segments 155A of the collapsible arms 154 of the expandable member 116 (shown in FIG. 16) are in contact with the peritoneum in the configuration illustrated in FIG. 18C.

Figure 18D:
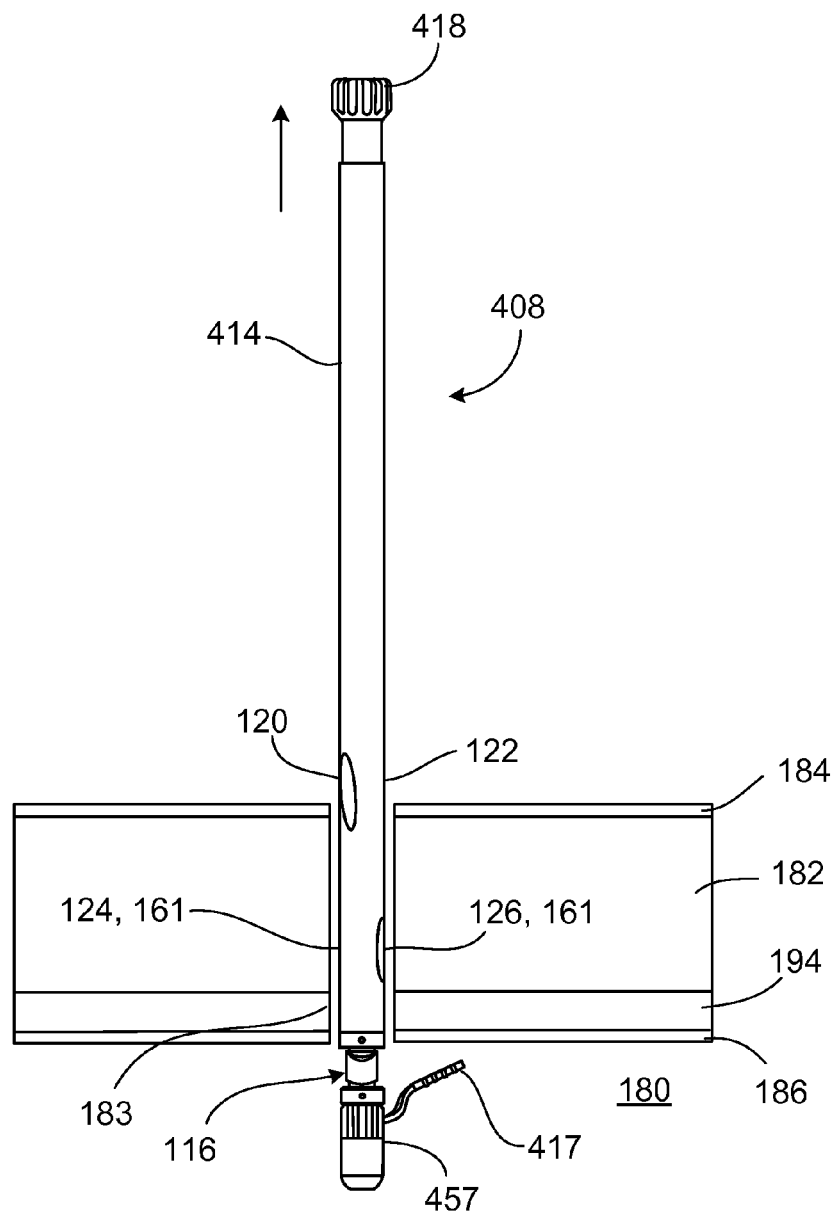

Prior to inserting the suture passer 110 through the suture passer guide 408, the button 418 is rotated, if necessary, to ensure that the suture positioning member 417 is oriented circumferentially offset from the distal opening 126 of the guide passage 136, as shown in FIG. 18D. This will prevent the suture passer 110 from contacting the suture positioning member 417 when the suture passer 110 is passed through the guide passage 136. Although the suture positioning member 417 is shown oriented to the right side of the suture passer guide 408 in FIG. 18D, the suture positioning member 417 may be oriented at any circumferential position about the longitudinal axis 444 of the suture passer guide 408 in which the suture positioning member 417 avoids interfering with the suture passer 110 when it is inserted through the guide passage 136 of the suture passer guide 408. The user then applies a proximal force to the suture passer guide 408 to ensure that the expanded expandable member 116 is in contact with the peritoneum 186.

Figure 18E:
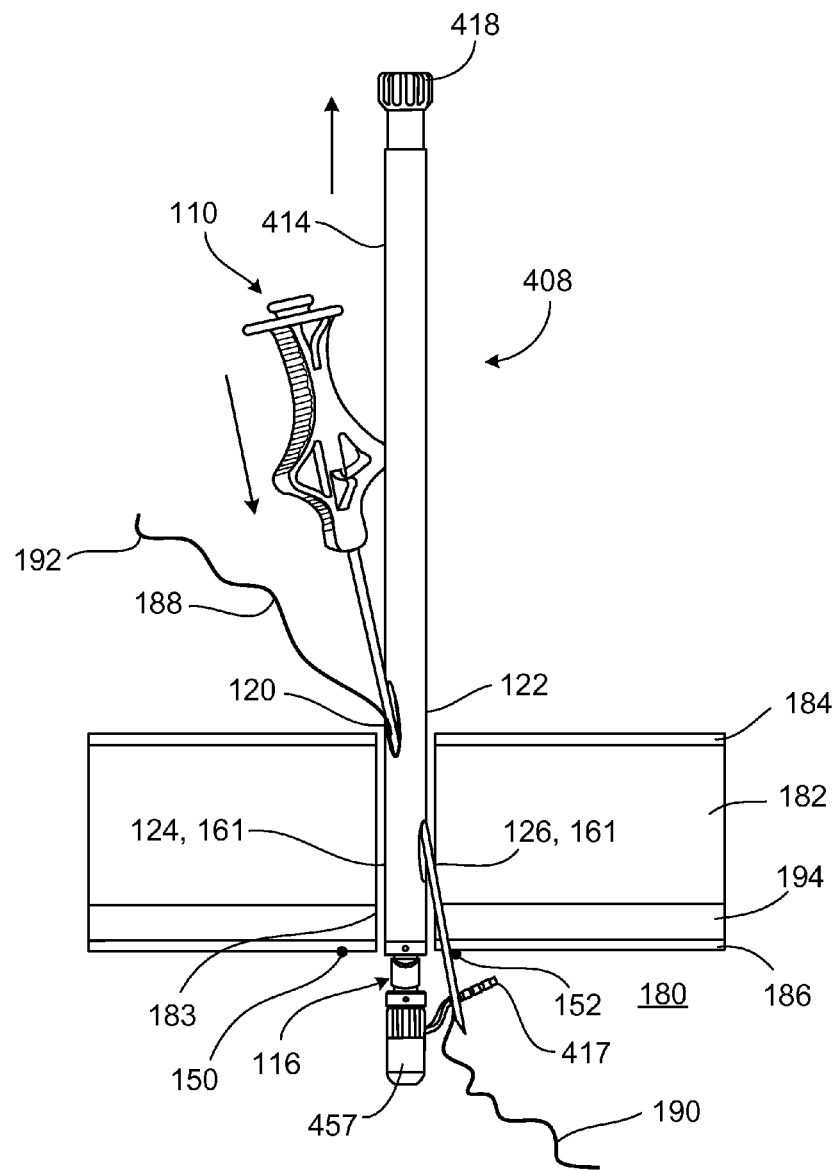

Referring to FIG. 18E, the suture passer 110 is then loaded with the suture 188 such that the first end 190 of the suture 188 extending from a distal end region of the suture passer 110 has a length sufficient to accommodate repositioning of the first end 190 of the suture 188 upon rotating the suture positioning member 417 to the opposite side of the suture passer guide. The suture passer 110 is then passed through the guide passage 136 such that the suture passer 110 punctures the peritoneum 186 at the right puncture point 152. In this manner, the first end 190 of the suture 188 is carried into the abdominal cavity 180 along with the distal end of the suture passer 110.

Figure 18F:
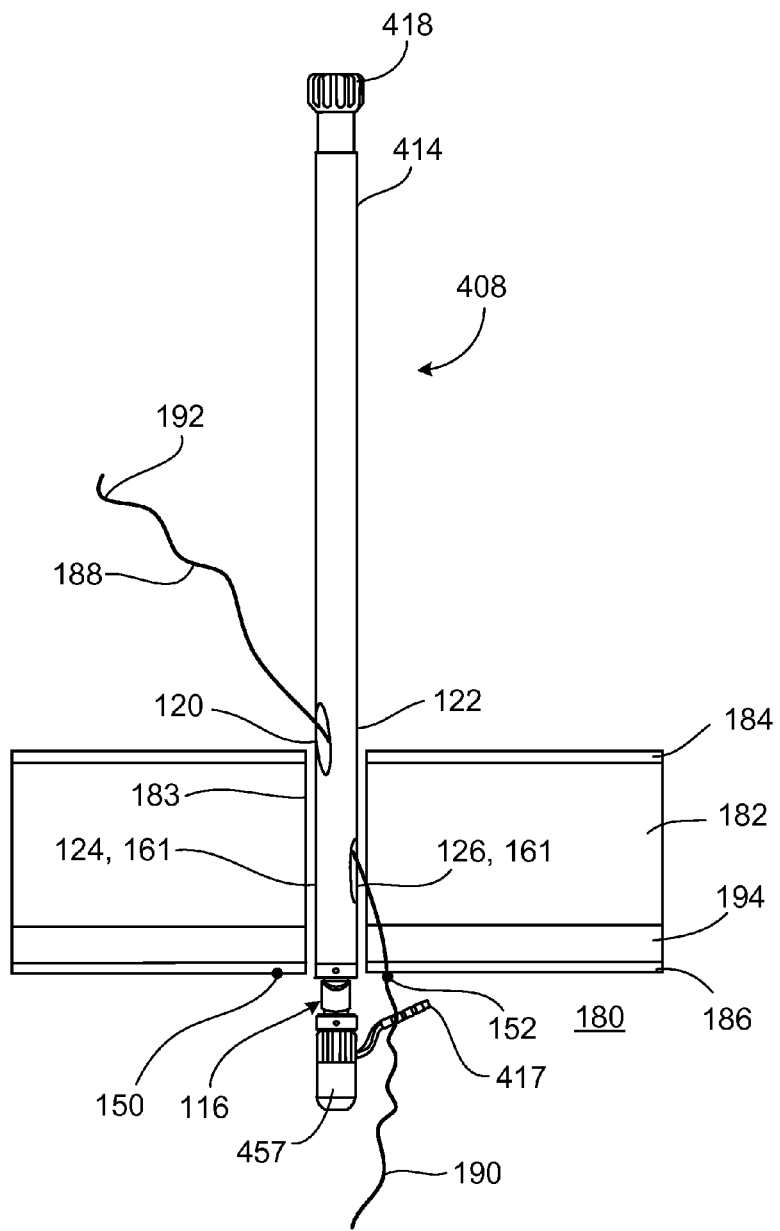

Referring to FIG. 18F, after depositing the first end 190 of the suture 188 in the abdominal cavity 180, the suture 188 is released, and the suture passer 110 is removed from the guide passage 136.

Figure 18G:
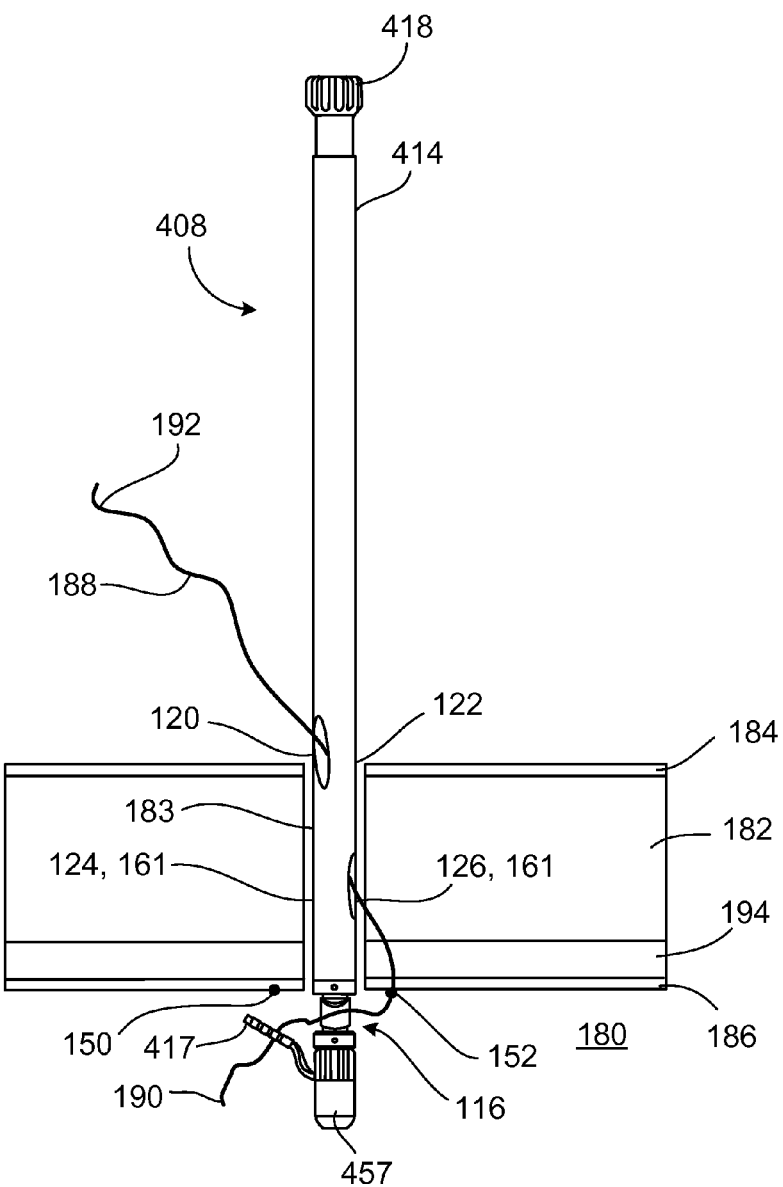

Referring to FIG. 18G, the button 418 is then rotated about the longitudinal axis of the elongate tubular member 414, causing the suture positioning member 417 to rotate to the left side of the suture passer guide. As a result, the suture positioning member 417 pushes the first end 190 of the suture 188 to the left side of the suture passer guide 408 and in proximity to the distal opening 124 of the guide passage 138 so that the first end 190 of the suture 188 can be easily retrieved by the suture passer 110. The button 418 is typically rotated until the suture positioning member 417 is positioned slightly circumferentially offset from the distal opening 124 of the guide passage 138 to prevent the suture passer 110 from contacting the suture positioning member 417 as the suture passer 110 is passed through the guide passage 138 and the peritoneum 186. The button 418 and the suture positioning member 417 are typically rotated through an angle of about 160° to about 200° from the right side of the suture passer guide 408 to the left side of the suture passer guide 408. Because the suture positioning member 417 is able to rotate around a significant portion of the circumference of the elongate tubular member 414 (e.g., 360 degrees around the elongate tubular member 414), the first end 190 of the suture 188 need not typically be precisely placed within the abdominal cavity in order to ensure that the suture positioning member 417 is able to engage the first end 190 of the suture 188 to reposition the suture 188.

Figure 18H:
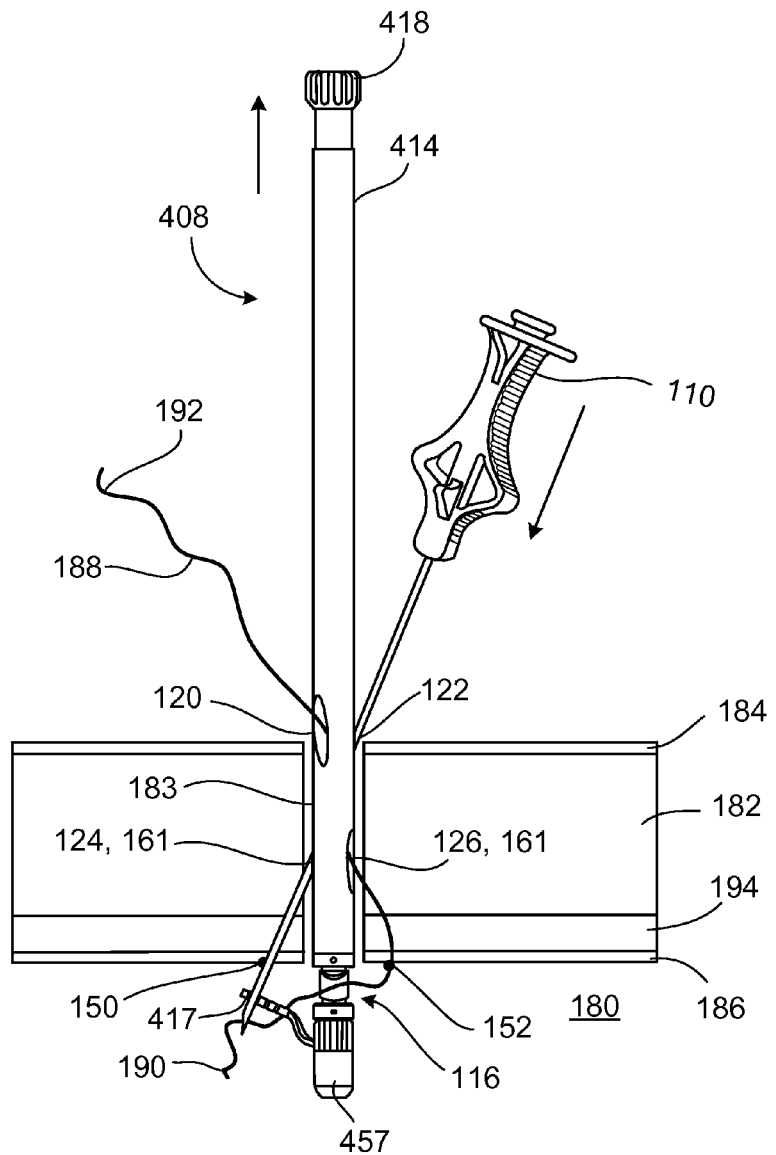

Referring to FIG. 18H, with the suture passer guide 408 being pulled proximally, the suture passer 110 is then inserted through the guide passage 138 such that the suture passer 110 punctures the peritoneum 186 at the left puncture point 150. The suture 188 is then grasped with the suture passer 110.

Although the suture passer 110 has been described as being inserted through the guide passage 138 after rotating the suture positioning member 417 to the left side of the suture passer guide, it should be understood that the suture passer 110 can alternatively be inserted through the second guide passage 138 prior to rotating the suture positioning member 417 from the right side of the suture passer guide 408 to the left side of the suture passer guide 408.

Figure 18I:
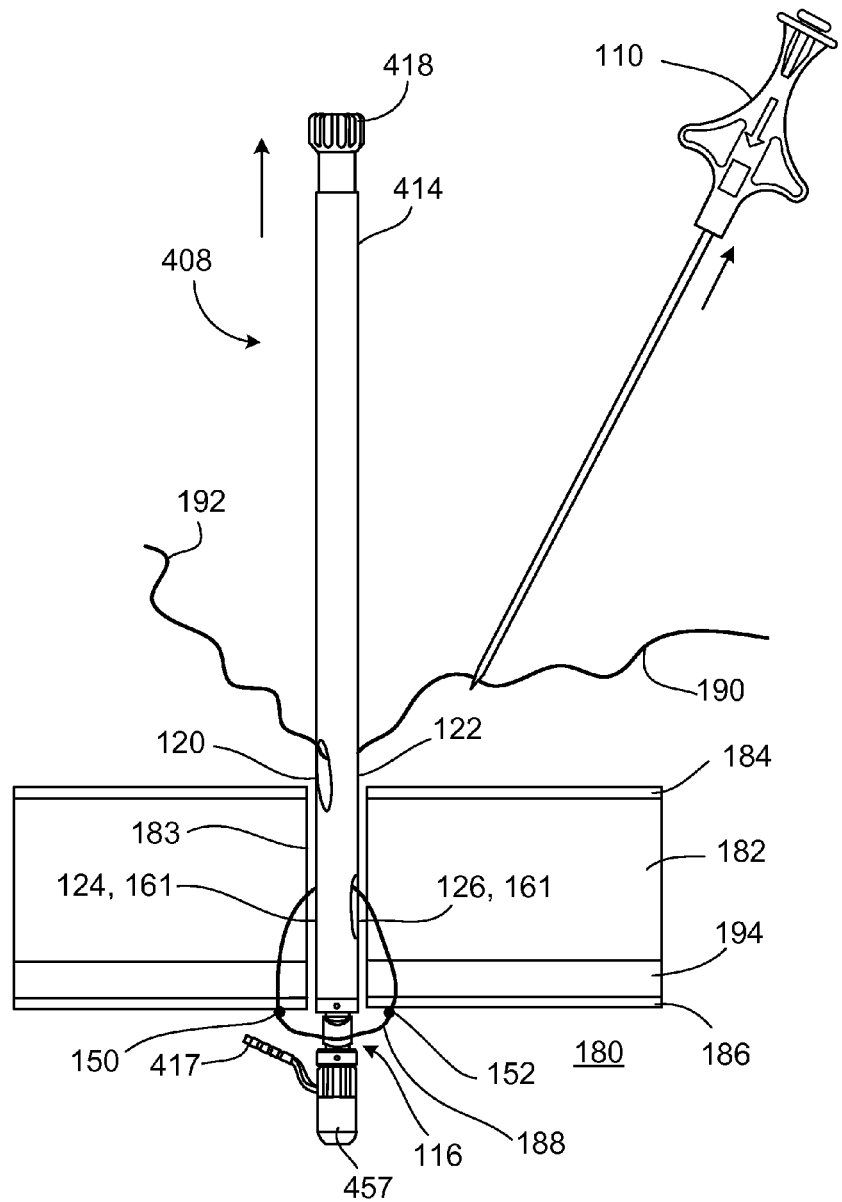

As shown in FIG. 18I, with the suture 188 in its grasp, the suture passer 110 is then removed from the guide passage 138. In doing so, the first end 190 of the suture 188 is pulled through the various tissue layers 186, 194, 182, 184 of the abdominal wall and outside of the patient. At this point, the first and second ends 190, 192 of the suture 188 are both positioned outside of the patient. The button 418 is then depressed to collapse the expandable member 116 and the suture positioning member 417, and the suture passer 408 is removed from the port site wound 183. The first and second ends 190, 192 of the suture 188 are tied to form a knot, which is positioned at a location proximal to the fascia 194, such that the fascia 194 and peritoneum 186 are substantially closed.

Surgical procedures including the wound closure procedure described above can typically be carried out in less time than those that require the endoscopic port 102 to be removed before inserting a suture passer guide or those that include a suture positioning member (e.g., the suture positioning member 117) having an aperture (e.g., the aperture 115) through which the suture 188 needs to be passed in order to reposition the suture 188. In addition, inserting the suture passer guide 408 through the endoscopic port 102 inhibits the loss of pneumoperitoneum and thus eliminates the time that might otherwise be required to re-insufflate the abdominal cavity following removal of the endoscopic port 102. Furthermore, inserting the suture passer guide 408 through the endoscopic port 102 removes the need to relocate the port site wound 183 following removal of the endoscopic port 102, which is required when using a type of suture passer guide that is inserted directly into the port site wound 183. This also contributes to the reduced time required for such a procedure. In addition, by inserting the suture passer guide 408 through the endoscopic port 102, additional tissue damage that might otherwise result from inserting a suture passer guide directly into the wound 183 can be avoided.

While the pin 449 has been described as being positioned along the longitudinal axis 144 of the elongate tubular member 414, in certain embodiments, the pin 449 is spaced apart from the longitudinal axis 444 of the elongate tubular member 414, such that the suture positioning member 417 pivots about an axis that is parallel to the longitudinal axis 444 of the elongate tubular member 414.

While the suture passer guide 408 has been described as including the expandable member 116, it should be appreciated that a suture passer guide including the suture positioning member 417 can alternatively include any of the various other expandable members described herein.

Figure 19:
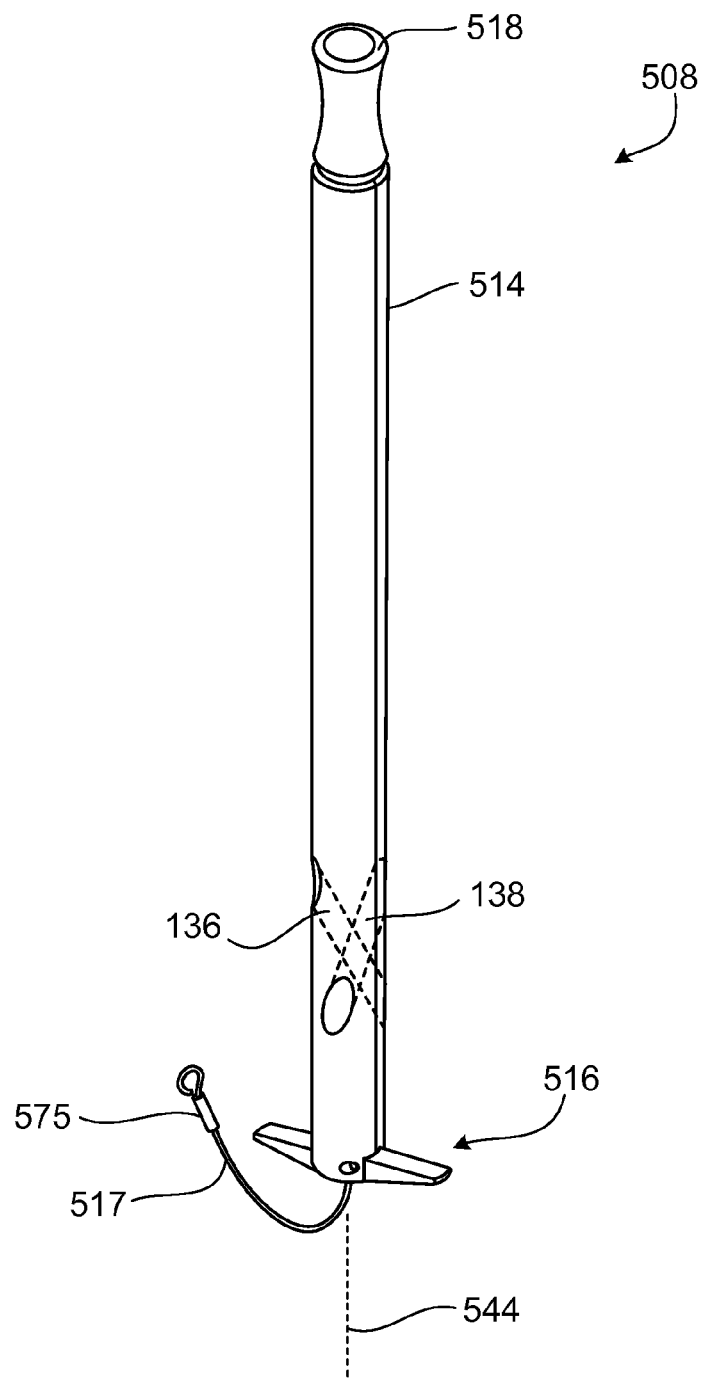
FIG. 19 is a perspective view of a suture passer guide that includes a suture positioning member in the form of a bent or curved wire that that is rotatable about an axis that is coincident with a longitudinal axis of an elongate tubular member of the suture passer guide to allow a suture to be repositioned from one side area of the elongate tubular member of the suture passer guide to another side area of the elongate tubular member of the suture passer guide.

While the suture passer guide 408 has been described as including the suture positioning member 417 that collapses flush with the outer surface of the distal base 457 of the suture passer guide 408, the suture passer guide can alternatively include a suture positioning member that can be disposed internal to the suture passer guide. For example, FIG. 19 illustrates a suture passer guide 508 that includes a suture positioning member (e.g., a wire) 517 that can be retracted into an elongate tubular member 514 of the suture passer guide 508 and that can be extended from a distal end region of the suture passer guide 508 when the suture positioning member 517 is actuated by a button 518 of an actuator. The suture positioning member 517 is operable to pivot or rotate about a longitudinal axis 544 of the elongate tubular member 514 such that the suture positioning member 517 can move a suture from one side of the elongate tubular member 514 to an opposite side of the elongate tubular member 514. The elongate tubular member 514 includes the guide passages 136, 138 and is configured to engage the button 518 located at a proximal end region of the elongate tubular member 514 and a distal base 556 (shown in FIG. 20) located at a distal end region of the elongate tubular member 514. The suture passer guide 508 further includes an expandable member 516 that can be radially expanded and collapsed by the actuator.

Figure 20:
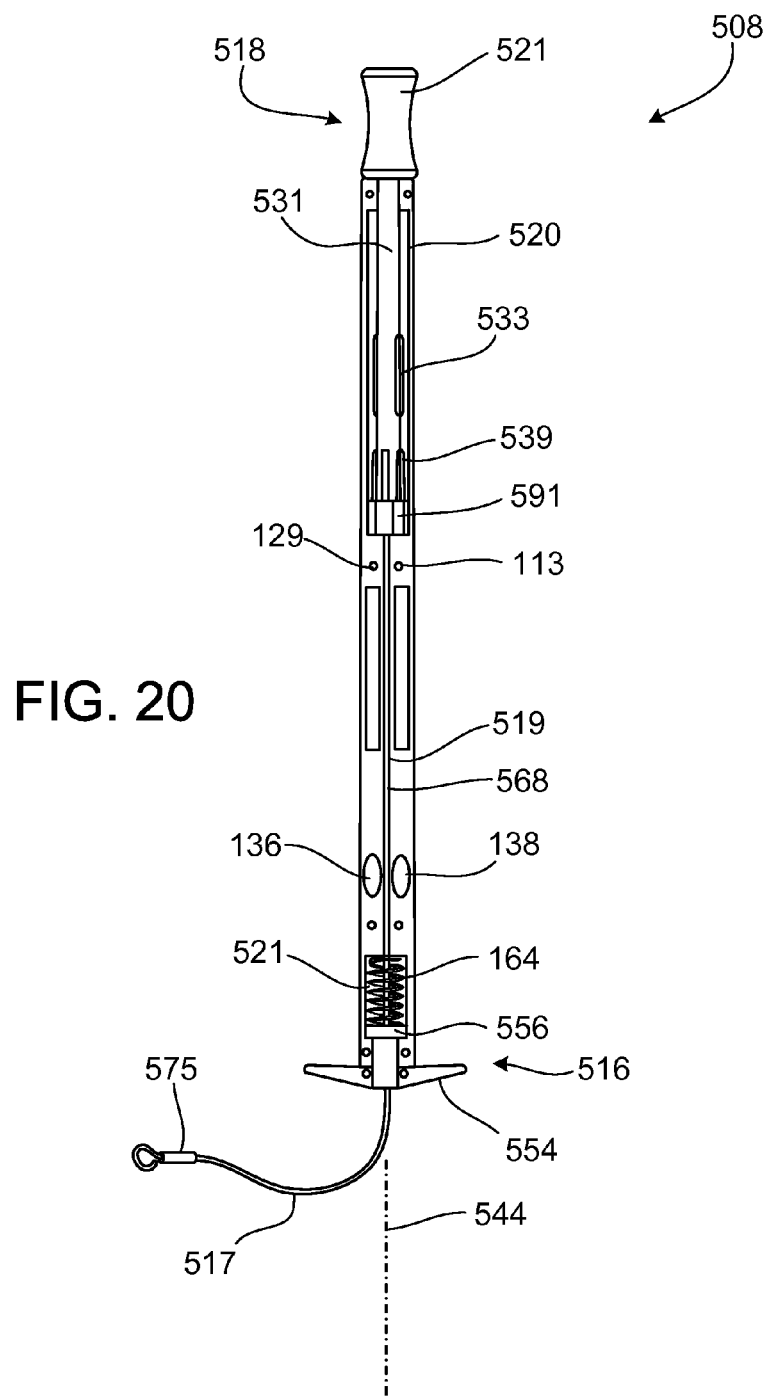
FIG. 20 is a front view of the suture passer guide of FIG. 19, with one half of the elongate tubular member of the suture passer guide removed to show certain internal components of the suture passer guide.

FIG. 20 illustrates a front view of the suture passer guide 508 with one half of the elongate tubular member 514 removed to show certain internal components of the suture passer guide 508. The elongate tubular member 514 includes a proximal lumen 520 sized to surround a portion of the button 518 secured to a proximal end of an internal shaft 568, a central lumen 519 through which the internal shaft 568 passes, and a distal lumen 521 into which the internal shaft 568 extends and that surrounds the spring 164. The elongate tubular member further includes the mating pegs 113 and recesses 129 that serve to align the two halves of the elongate tubular member 514. At the distal end region of the elongate tubular member 514, the internal shaft 568, which can be an integral extension of the suture positioning member 517 or a separate component that is affixed to the suture positioning member 517, extends through the spring 164 and into a central channel 590 (shown in FIGS. 22 and 23) formed in the distal base 556. The suture positioning member 517 extends from the distal end of the internal shaft 568 and is configured to slide within the central channel 590 of the distal base 556. The distal base 556 is sized and shaped to slide within the distal lumen 521. A plug 575 is attached to the distal end region of the suture positioning member 571 and engages the distal base 556 when the button 518 is pulled proximally such that the button 518 can be operated to actuate both the suture positioning member 517 and the expandable member 516, as will be discussed in more detail below.

Figure 21:
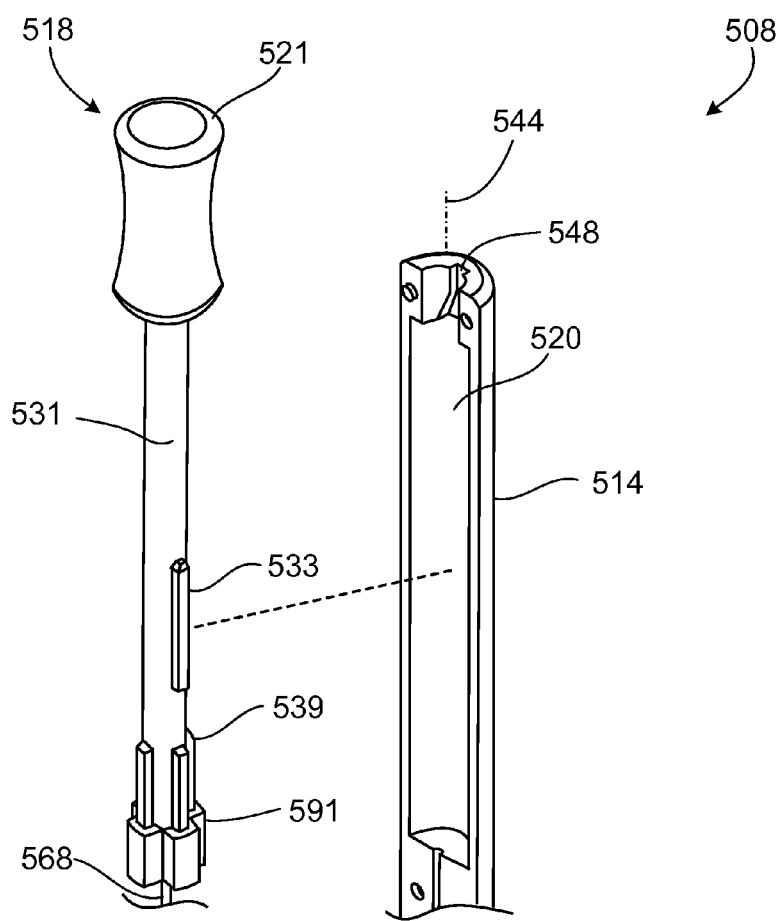
FIG. 21 is an enlarged perspective, exploded view of a proximal end region of the suture passer guide of FIG. 19, with one half of the elongate tubular member removed to show certain internal features of the suture passer guide.

FIG. 21 is an enlarged exploded view of the proximal end region of the suture passer guide 508 with one half of the elongate tubular member 514 removed to expose certain internal features of the suture passer guide 508. The button 518 includes a graspable head 521 and a shaft 531 extending distally from the head 521. Two opposing rotational stops 533 extend radially from a surface of the shaft 531 along a central region of the shaft 531, and four axial stops 539 extend radially from the surface of the shaft 531 along a distal end region of the shaft 531. Two opposing rotational cutouts 548 extend from an internal surface of the elongate tubular member 514 and are sized and shaped to receive the rotational stops 533. When the button 518 is disposed in a proximal position (not shown), the button 518 is oriented such that the rotational stops 533 extend into the rotational cutouts 548, thereby locking a rotational position of the button 518. In such a configuration, the button 518 may be pulled proximally until the axial stops 539 prevent further proximal movement of the button 518, such that the rotational stops 533 are disposed proximal to the rotational cutouts 548. In this manner, the button 518 can be rotated until the rotational stops 533 are offset from the rotational cutouts 548 to prevent the button 518 from sliding distally within the proximal lumen 520 of the elongate tubular member 514. Alternatively, the head 521 may be depressed to an extent that the rotational stops 533 are positioned distal to the rotational cutouts 548 such that the button 518 is rotatable within the proximal lumen 520 about the longitudinal axis 544 of the elongate tubular member 514. The button 518 further includes frictional members 591 that extend radially from the surface of the shaft 531 and distally from the axial stops 539. The frictional members 591 contact a wall of the proximal lumen 520 and provide resistance to rotational motion such that the button 518 can be maintained in a desired rotational position.

Still referring to FIG. 21, the shaft 531 of the button 518 is coupled to the proximal end of the internal shaft 568. The button 518 and the internal shaft 568 are axially slidable within the proximal lumen 520 along the longitudinal axis 544 of the elongate tubular member 514. The distal end of the internal shaft 568 is connected to the suture positioning member 517 (shown in FIGS. 22 and 23), such that rotating or axially moving the button 518 causes respective rotational or axial movement of the suture positioning member 517 about the longitudinal axis 544 of the elongate tubular member 514. The button 518 can be depressed a first distance to move the rotational stops 533 just distally past the rotational cutouts 548 such that the button 518 is positioned in an intermediate axial position. The button 518 can further be depressed an additional second distance until a distal end of the shaft 531 contacts a distal surface of the proximal lumen 520 of the elongate tubular member 514. As will be described below, the button 518 can be moved the first distance to expand the expandable member 516 and can be moved the second distance to subsequently extend the suture positioning member 517 distally and radially from the elongate tubular member 514. In some embodiments, the button 518 may have a total stroke length (i.e., the first distance plus the second distance) of about 0.5 inch to about 2 inches (e.g., about 2 inches).

Figure 22:
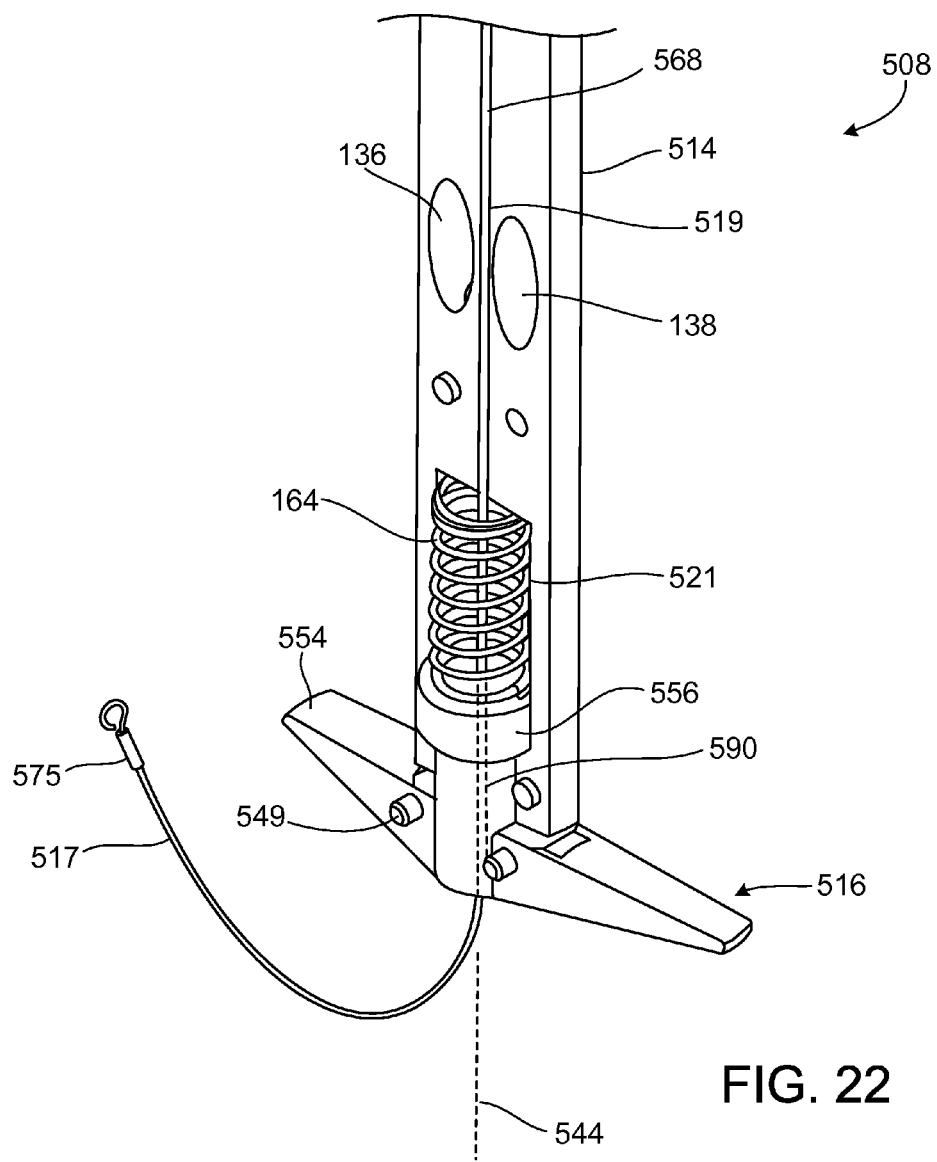
FIG. 22 is an enlarged perspective, view of the distal end region of the suture passer guide of FIG. 19, with one half of the elongate tubular member of the suture passer guide removed and with the suture positioning member shown in a radially extended position and the expandable member shown in a radially expanded configuration.
Figure 23:
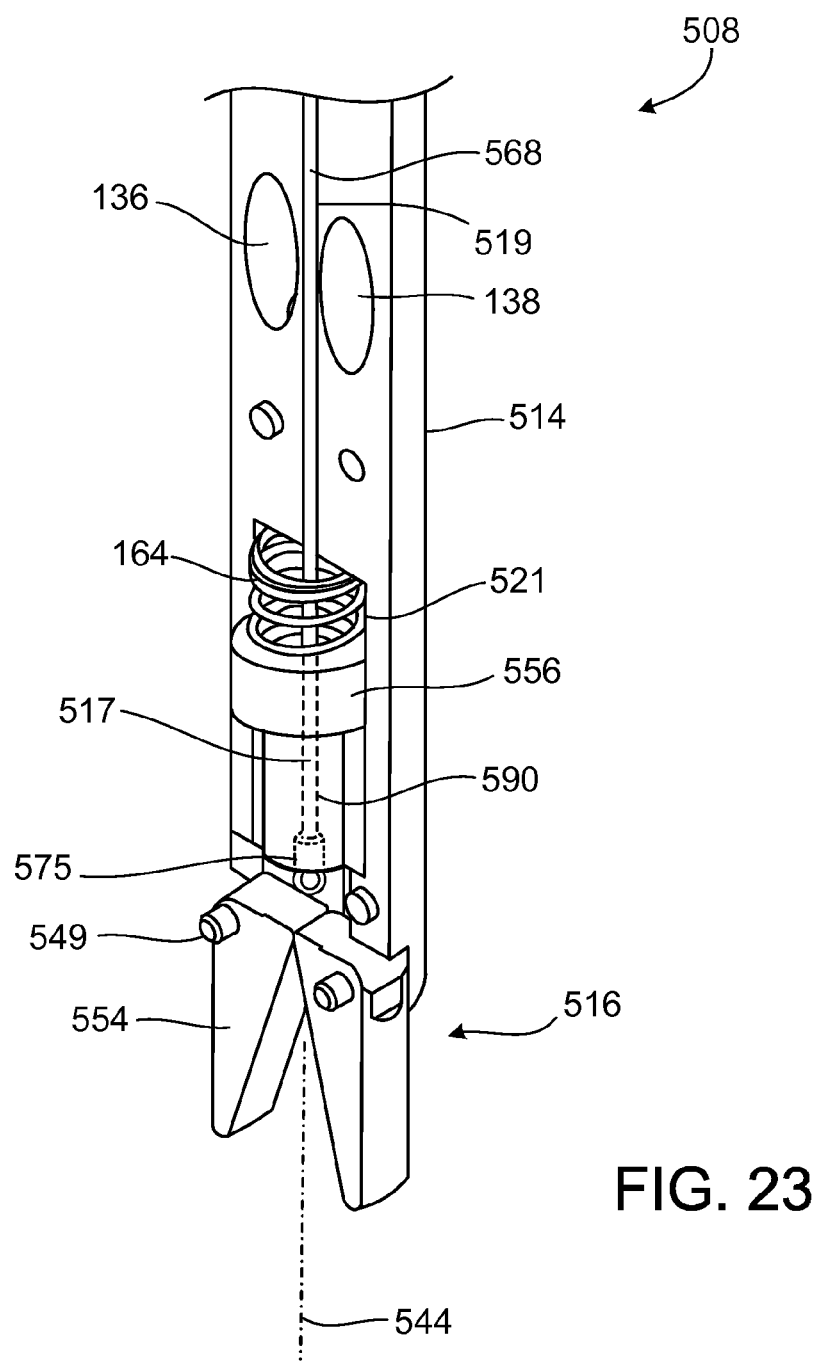
FIG. 23 is an enlarged perspective, view of the distal end region of the suture passer guide of FIG. 19, with one half of the elongate tubular member of the suture passer guide removed and with the suture positioning member shown in a radially retracted position and the expandable member shown in a radially collapsed configuration.

FIGS. 22 and 23 illustrate enlarged perspective views of the distal end region of the suture passer guide 508 with the suture positioning member 517 disposed internal and external, respectively, to the suture passer guide 508. One half of the elongate tubular member 514 has been removed to expose certain internal components of the suture passer guide 508. As discussed above, the distal end of the internal shaft 568 extends within the central channel 590 of the distal base 556, and the suture positioning member 517 extends distally from the distal end of the internal shaft 568. The internal shaft 568 and the suture positioning member 517 are slidable within the central channel 590 of the distal base 556, such that the suture positioning member 517 can be disposed entirely internal to the elongate tubular member 514, as shown in FIG. 23, or can be extended from the distal end region of the elongate tubular member 514, as shown in FIG. 22. The suture positioning member 517 takes on a prescribed curved shape (shown in FIG. 22) when extended from the elongate tubular member 514, but is sufficiently flexible such that the suture positioning member 517 can straighten to be disposed within the central channel 590 of the distal base 556 when moved proximally within the elongate tubular member 514. The plug 575, which is larger in diameter than the suture positioning member 517, is attached to the distal end region of the suture positioning member 517 and is sized to be disposed within the central channel 590 of the distal base 556 when the internal shaft 568 is in a proximal position. As the plug 575 and the suture positioning member 517 are pulled proximally, the proximal surface of the plug 575 contacts a projection or step that extends radially inward within the central channel 590 of the distal base 556 in a manner that prevents further proximal motion of the plug 575 and the suture positioning member 517 relative to the distal base 556. As a result, further proximal movement of the plug 575 and the suture positioning member 517 causes the distal base 556 to move proximally and compress the spring 164.

Still referring to FIGS. 22 and 23, when the button 518 is rotated, the suture positioning member 517 is accordingly rotated about the longitudinal axis 544 of the elongate tubular member 514, such that the suture positioning member 517 may push or sweep a suture from one side of the elongate tubular member 514 to an opposite side of the elongate tubular member 514. In some embodiments, the suture positioning member 517 has a diameter of about 0.015 inch to about 0.035 inch and a length of about 1.5 inches to about 2 inches. The suture positioning member 517 can be made of one or more medical grade materials that have shape-memory properties. In some embodiments, for example, the suture positioning member 517 is a nitinol wire.

The expandable member 516 includes two opposing arms 554 that are biased to positions that are substantially parallel to the longitudinal axis 544 of the elongate tubular member 514. The arms 554 can, for example, be spring-loaded into this configuration. The arms 554 of the expandable member 516 are pivotable about respective hinges 549.

Referring particularly to FIG. 22, the spring 164 applies an outward (extension) force to the distal base 556 such that the distal base 556 extends past the distal end of the elongate tubular member 514. In this manner, the distal base 556 contacts the arms 554 and forces the arms 554 of the expandable member 516 outward from the longitudinal axis 544 of the elongate tubular member 514, such that the arms 554 are oriented substantially perpendicular to the longitudinal axis 544. In some embodiments, the arms 554 have a width of about 0.1 inch to about 0.2 inch.

Referring particularly to FIG. 23, as the button 518 is moved sufficiently proximally (i.e., such that the rotational stops 533 are positioned proximal to the rotational cutouts 548 of the button 518), the suture positioning member 517 slides proximally within the central channel 590 of the distal base 556 until the plug 575 seats within the distal end of the central channel 590. In this manner, the plug 575 pulls the distal base 556 proximally within the distal lumen 521 until the distal base 556 is positioned internal to the distal lumen 521. In such a configuration, the distal base 556 no longer forces the arms 544 of the expandable member 516 radially outward from the longitudinal axis 544 of the elongate tubular member 514, and the arms 554 collapse to their biased positions that are substantially parallel to the longitudinal axis 544 of the elongate tubular member 514.

In some embodiments, the suture passer guide 508 includes an indicator (e.g., an arrow) on a top surface of the head 521 of the button 518 to indicate a circumferential position of the suture positioning member 517. The indicator can, for example, indicate the direction of bend of the wire that forms the suture positioning member 517.

In certain embodiments, the proximal end region of the elongate tubular member 514 of the suture passer guide 508 includes gripping features, such as depressions, rings, or any other types of textured surfaces that improve the ability of the surgeon to grip the suture passer guide 508.

In some embodiments, the distal end region of the suture passer guide 508 includes a set of ruler markings that allow the surgeon to gauge the thickness of the tissue through which the suture passer guide 508 has been inserted. The suture passer guide 508 may typically be used to suture surgical walls having thicknesses of about 3 cm to about 12 cm.

In certain embodiments, the suture passer guide 508 also includes self-sealing elastic plugs disposed within one or more of the guide passage openings to assist in maintaining the pressure of a pressurized surgical cavity throughout a wound repair procedure.

The suture passer guide 508 may be used with components of an endoscopic surgical kit to perform a laparoscopic surgical procedure in a surgical cavity (e.g., an abdominal cavity) of a patient and to subsequently repair an endoscopic port wound used to access the surgical cavity. The suture passer guide 508 may be used in a manner that is similar to the suture passer guide 408 discussed above to carry out such a procedure.

In particular, after completing a surgical procedure within the abdominal cavity of a patient and with the endoscopic port positioned within the abdominal wall tissue of the patient, the suture passer guide 508 is inserted through the central lumen of the endoscopic port and into the abdominal cavity. To insert the suture passer guide 508 through the central lumen of the endoscopic port, the button 518 is first rotated such that the rotational stops 533 extending from the shaft 531 of the button 518 engage the rotational cutouts 548 extending from the internal surface of the elongate tubular member 514, and the button 518 is pulled proximally until the rotational stops 533 are disposed proximal to the elongate tubular member 514. The button 518 is then rotated until the rotational stops 533 are circumferentially offset from the rotational cutouts 548 such that the proximal position of the button 518 is maintained, the suture positioning member 517 is fully retracted within the distal base 556 of the suture passer guide 508, and the expandable member 516 is biased to its collapsed configuration. The suture passer guide 508 is then inserted into the central lumen of the endoscopic port.

When the expandable member 516 is passed distally beyond the distal end of the endoscopic port, the button 518 is rotated until the rotational stops 533 are aligned with the rotational cutouts 548, and the button 518 is depressed until the rotational stops 533 are positioned just distal to a proximal end of the proximal lumen 520 of the elongate tubular member 514. The button 518 is then rotated until the rotational stops 533 are circumferentially offset from the rotational cutouts 548 such that an intermediate position of the button 518 is maintained, and the plug 575 is shifted distally out of the central channel 590 of the distal support base 556, allowing the distal support base 556 to move distally within the distal lumen 521 of the elongate tubular member 514. In this manner, the spring 164 extends to push the distal base 556 distally, thereby causing the arms 554 of expandable member 516 to extend outward from the longitudinal axis 544 of the elongate tubular member 514.

With the expandable member 516 in its expanded configuration, the suture positioning member 517 retracted within the central channel 590 of the distal support base 556, and the plug 575 extending slightly distal to the distal support base 556, the endoscopic port is then removed from the endoscopic port site wound by pulling proximally on the proximal end region of the endoscopic port. As the endoscopic port is removed from the port site wound, the expanded expandable member 516 contacts the inner lining of the patient's peritoneum, thereby preventing the suture passer guide 508 from being pulled out of the port site wound along with the endoscopic port.

The button 518 is then depressed to its distal position, causing the suture positioning member 517 to extend distally out of the central channel 590 of the distal support base 556, and the button 518 is rotated, if necessary, to ensure that the suture positioning member 517 is oriented slightly circumferentially offset from the distal opening 126 of the guide passage 136 to prevent a suture passer from contacting the suture positioning member 517 when the suture passer is passed through the guide passage 136.

A suture passer is then loaded with a suture and passed through the guide passage 136 such that the suture passer punctures the peritoneum and carries the suture into the abdominal cavity of the patient. After depositing the first end of the suture in the abdominal cavity, the suture is released, and the suture passer is removed from the guide passage 136.

The button 518 is then rotated to cause the suture positioning member 517 to rotate from the right side of the suture passer guide 508 to the left side of the suture passer guide 508, pushing the first end of the suture to the left side of the suture passer guide 508 and in proximity to the distal opening 124 of the guide passage 138 so that the first end of the suture can be easily retrieved by the suture passer. The button 518 is rotated until the suture positioning member 517 is positioned slightly circumferentially offset from the distal opening 124 of the guide passage 138 to prevent the suture passer from contacting the suture positioning member 517 as the suture passer is passed through the guide passage 138 and the peritoneum. The button 518 and the suture positioning member 517 are typically rotated through an angle of about 160° to about 200° from the right side of the suture passer guide 508 to the left side of the suture passer guide 508.

The suture passer is then inserted through the guide passage 138 such that the suture passer punctures the peritoneum and travels into the abdominal cavity where the suture passer is used to grasp the repositioned suture. With the suture in its grasp, the suture passer is then removed from the guide passage 138, pulling the first end of the suture through the various tissue layers of the abdominal wall and outside of the patient. At this point, the first and second ends of the suture are positioned outside of the patient. The button 518 is then pulled until the rotational stops 533 contact the proximal end of the proximal lumen 520 of the elongate tubular member 514. The button 518 is then rotated until the rotational stops 533 are aligned with the rotational cutouts 548 of the elongate tubular member 514, and the button 518 is pulled further to its proximal position, thereby pulling the suture positioning member 517 and the plug 575 within the central lumen of the distal base 556 and allowing the arms 554 of the expandable member 516 to collapse. The button 518 is rotated to circumferentially offset the rotational stops 533 from the rotational cutouts 548, and the suture passer guide 508 is then removed from the port site wound. The first and second ends of the suture are then tied to close the wound.

In some examples, the suture passer 110 may alternatively be inserted through the second guide passage 138 prior to rotating the suture positioning member 517 from the right side of the suture passer guide 508 to the left side of the suture passer guide 508.

Figure 24:
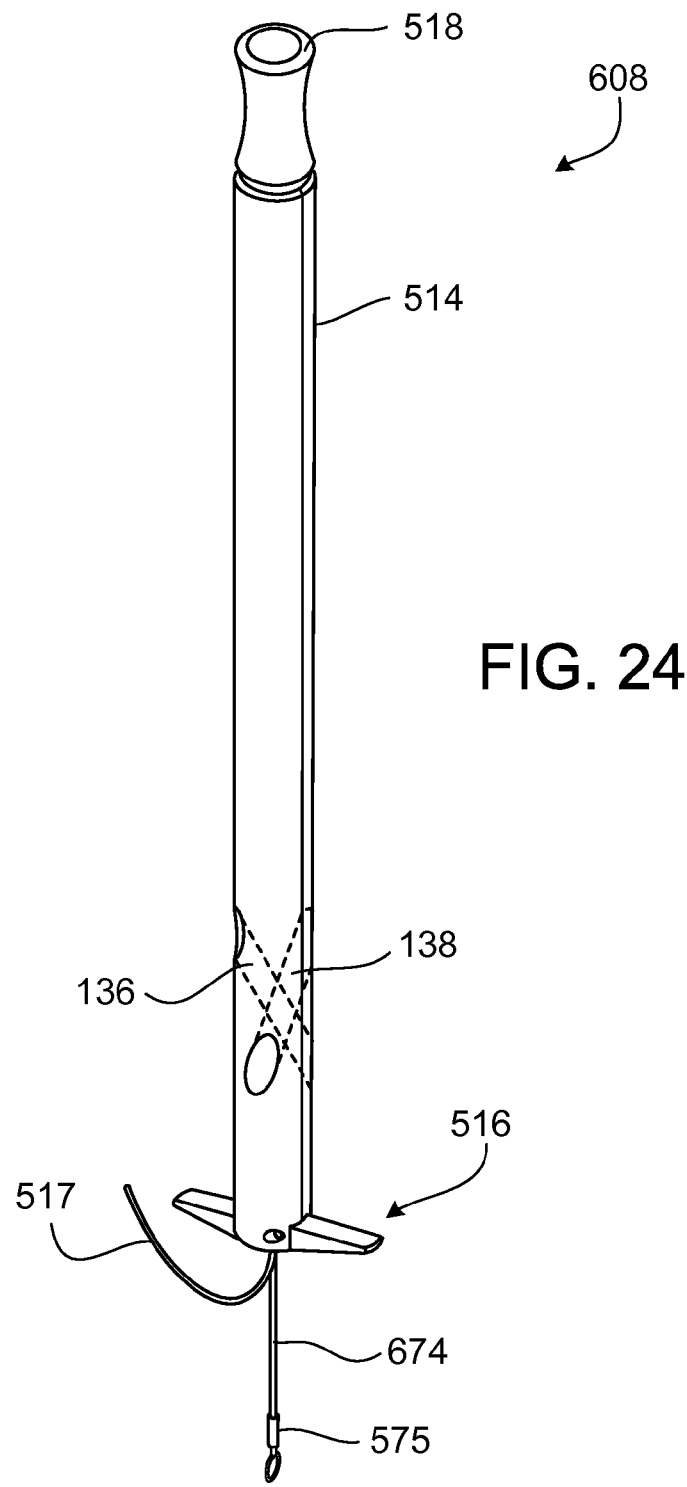
FIG. 24 is a perspective view of a suture passer guide that is generally similar to the suture passer guide of FIG. 19 but that includes, in addition to the suture positioning member, a rod that can be axially displaced in a manner to radially expand and collapse the expandable member of the suture passer guide.

While the suture positioning member 517 of the suture passer guide 508 has been described as having the plug 575 attached to its distal end region, in some embodiments, no such plug is attached to the suture positioning member 517. For example, FIG. 24 illustrates a suture passer guide 608 that includes the suture positioning member 517, a rod 674 sized to be disposed within a central channel of a distal support member, and the plug 575 connected to a distal end of the rod 674. The suture passer guide 608 is substantially similar in construction and function to the suture passer guide 508, with the exception that the suture passer guide 608 includes the rod 674 with the plug 575 attached to the distal end of the rod 674 and a distal support member having a central channel sized to receive surround both the suture positioning member 517 and the rod 674 simultaneously. In certain embodiments, either or both of the suture positioning member 517 and the rod 674 may be made integral with the internal shaft 568.

While the suture passer guides 108, 208, 308, 408, 508, 608 have been described as including self-sealing elastic plugs 161 sized to be disposed within the distal openings of their guide passages, in certain embodiments, the suture passer guide includes self-sealing elastic patches that are sized to cover the distal openings of the guide passages. In this case, the elastic patches include a self-adhesive area disposed along an edge of one surface of the patches, such that the patches can be adhered to the external surface of the elongate tubular member surrounding the distal openings. A thickness of the elastic patches is typically about 0.005 inch to about 0.020 inch.

While some of the suture passer guides described above include plugs or seals positioned within or over, respectively, the distal openings of the guide passages, it should be understood that the plugs or seals can alternatively or additionally be positioned within or over the proximal openings of the guide passages.

While certain suture passer guides described above include seals positioned in or over openings of the guide passages to inhibit gases from escaping from the surgical cavity via the guide passages, in certain embodiments, no such seals are used.

While the endoscopic surgical kits discussed above have been described as including a single endoscopic port 102, obturator 104, suture passer guide 108, 208, 308, 408 508, 608, and suture passer 110, the kit can alternatively include multiple, different endoscopic ports, obturators, suture passer guides, and/or suture passers of varying size for performing endoscopic (e.g., laparoscopic) surgical procedures on patients of various sizes.

While the endoscopic surgical kits discussed above have been described as being used to carry out a laparoscopic surgical procedure, it should be understood that the endoscopic surgical kits can be used to perform any of various other types of endoscopic surgical procedures.

What is claimed is:

1. A suture passer guide comprising:
    an elongate member having a longitudinal axis, the elongate member defining a first opening and a second opening that are substantially aligned with one another such that a suture passer and a suture grasped by the suture passer can be extended through the first and second openings at an acute angle relative to the longitudinal axis of the elongate member;
    a suture positioning member that can be radially extended from a distal end region of the elongate member and rotated through an angle of at least 90° relative to the longitudinal axis of the elongate member from a first side area of the elongate member to a second, opposite side area of the elongate member such that the suture positioning member can move the suture through the angle of at least 90° from the first side area of the elongate member to the second, opposite side area of the elongate member;
    an actuator having a graspable member extending from a proximal end region of the elongate member, wherein the actuator is configured to rotate the suture positioning member relative to the elongate member when the graspable member of the actuator is moved from a first position to a second position, and
    an expandable member that is secured to the elongate member and that can be moved from a radially expanded position to a radially collapsed position,
    wherein the actuator is configured to move the expandable member from the radially expanded position to the radially collapsed position, and wherein the actuator is further configured to radially extend the suture positioning member.

2. The suture passer guide of claim 1, wherein the suture positioning member is configured to rotate about an axis that is substantially parallel to or coincident with the longitudinal axis of the elongate member.

3. The suture passer guide of claim 2, wherein the suture positioning member is pivotably connected to a distal support member that is axially fixed to the elongate member.

4. The suture passer guide of claim 3, further comprising a shaft that extends through the elongate member, the shaft being configured to radially extend or radially retract the suture positioning member when the shaft is moved axially.

5. The suture passer guide of claim 4, further comprising a distal base that is axially fixed relative to the shaft, the distal base defining a cavity configured to receive the suture positioning member when the suture positioning member is in a radially retracted position.

6. The suture passer guide of claim 4, wherein the shaft is further configured to radially expand or radially collapse the expandable member that is secured to the elongate member.

7. The suture passer guide of claim 4, wherein the shaft is configured to rotate the suture positioning member relative to the elongate member when the shaft is rotated relative to the elongate member.

8. The suture passer guide of claim 2, wherein the suture positioning member has a distal end region that is biased to a bent configuration.

9. The suture passer guide of claim 8, wherein the suture positioning member can be placed in a first axial position with respect to the elongate member in which the distal end region of the suture positioning member extends from the elongate member and in a second axial position with respect to the elongate member in which the distal end region of the suture positioning member is disposed within the elongate member, and wherein the distal end region of the suture positioning member assumes the bent configuration when the suture positioning member is in the first axial position and the distal end region of the suture positioning member assumes a substantially straight configuration when the suture positioning member is in the second axial position.

10. The suture passer guide of claim 1, wherein the suture positioning member can be moved from a radially extended position to a radially retracted position in which the suture positioning member extends along an axis that is substantially parallel to or coincident with the longitudinal axis of the elongate member.

11. The suture passer guide of claim 10, further comprising a base coupled to the distal end region of the elongate member, the base defining a cavity that receives the suture positioning member when the suture positioning member is in the radially retracted position.

12. The suture passer guide of claim 11, wherein the suture positioning member is configured such that at least a portion of the suture positioning member is substantially flush with an outer surface of the base when the suture positioning member is in the radially retracted position.

13. The suture passer guide of claim 11, wherein the base comprises an aperture through which the suture positioning member extends when the suture positioning member is in the radially extended position.

14. The suture passer guide of claim 1, wherein the suture positioning member comprises a textured surface configured to contact the suture.

15. The suture passer guide of claim 1, wherein the actuator comprises a shaft that extends through a lumen of the elongate member and is coupled to the suture positioning member, and wherein the shaft is configured to rotate relative to the elongate member.

16. The suture passer guide of claim 15, wherein rotational movement of the shaft relative to the elongate member causes rotational movement of the suture positioning member relative to the elongate member.

17. The suture passer guide of claim 1, wherein a surface of the actuator has an indicator thereon, and wherein the indicator indicates a direction in which the suture positioning member will extend radially from the distal end region of the elongate member upon moving the actuator to radially extend the suture positioning member.

18. The suture passer guide of claim 1, wherein, in the radially expanded position, the expandable member extends radially beyond a circumferential surface of the elongate member.

19. The suture passer guide of claim 1, wherein the actuator is further configured to rotate the suture positioning member from the first side area of the elongate member to the second side area of the elongate member.

20. The suture passer guide of claim 1, wherein the elongate member defines third and fourth openings that are substantially aligned with one another such that the suture passer can be extended through the third and fourth openings at an acute angle relative to the longitudinal axis of the elongate member.

21. The suture passer guide of claim 20, wherein the elongate member defines a first guide passage that extends from the first opening to the second opening and a second guide passage that extends from the third opening to the fourth opening.

22. The suture passer guide of claim 21, wherein an entire length of the first guide passage is laterally offset from the longitudinal axis in a first direction such that the first guide passage does not intersect the longitudinal axis, and an entire length of the second guide passage is laterally offset from the longitudinal axis in a second direction such that the second guide passage does not intersect the longitudinal axis.

23. A suture passer guide comprising:
an elongate member having a longitudinal axis, the elongate member defining a first opening and a second opening that are substantially aligned with one another such that a suture passer and a suture grasped by the suture passer can be extended through the first and second openings at an acute angle relative to the longitudinal axis of the elongate member;
a suture positioning member that can be radially extended from a distal end region of the elongate member and rotated through an angle of at least 90° about an axis that is substantially perpendicular to the longitudinal axis of the elongate member, from a first side area of the elongate member, through the longitudinal axis of the elongate member, and to a second, opposite side area of the elongate member such that the suture positioning member can move the suture through the angle of at least 90° from the first side area of the elongate member to the second, opposite side area of the elongate member
an actuator having a graspable member extending from a proximal end region of the elongate member, wherein the actuator is configured to rotate the suture positioning member relative to the elongate member when the graspable member of the actuator is moved from a first position to a second position; and
an expandable member that is secured to the elongate member and that can be moved from a radially expanded position to a radially collapsed position,
wherein the actuator is configured to move the expandable member from the radially expanded position to the radially collapsed position, and wherein the actuator is further configured to radially extend the suture positioning member.

24. The suture passer guide of claim 23, wherein the suture positioning member defines an aperture sized to receive the suture.

25. The suture passer guide of claim 24, wherein the suture positioning member comprises two arms that define the aperture, and wherein a slit is defined between ends of the arms, the slit being configured to allow the suture to pass therethrough.

* * * * *